United States Patent
Low et al.

(10) Patent No.: US 10,505,118 B2
(45) Date of Patent: Dec. 10, 2019

(54) ORGANIC ELECTROLUMINESCENT DEVICE

(71) Applicants: GUANGDONG AGLAIA OPTOELECTRONIC MATERIALS CO., LTD., Foshan, Guangdong (CN); BEIJING AGLAIA TECHNOLOGY DEVELOPMENT CO., LTD., Beijing (CN)

(72) Inventors: Kam-Hung Low, Foshan (CN); Zhe Li, Foshan (CN); Jinxin Chen, Foshan (CN); Lifei Cai, Beijing (CN)

(73) Assignees: GUANGDONG AGLAIA OPTOELECTRONIC MATERIALS CO., LTD., Foshan (CN); BEIJING AGLAIA TECHNOLOGY DEVELOPMENT CO., LTD., Beijing (CN)

( * ) Notice: Subject to any disclaimer, the term of this patent is extended or adjusted under 35 U.S.C. 154(b) by 172 days.

(21) Appl. No.: 15/557,098

(22) PCT Filed: Sep. 1, 2015

(86) PCT No.: PCT/CN2015/088711
§ 371 (c)(1),
(2) Date: Sep. 11, 2017

(87) PCT Pub. No.: WO2016/014693
PCT Pub. Date: Sep. 15, 2016

(65) Prior Publication Data
US 2018/0047910 A1    Feb. 15, 2018

(30) Foreign Application Priority Data
Mar. 9, 2015    (CN) .......................... 2015 1 0102468

(51) Int. Cl.
*C09K 11/06*    (2006.01)
*H01L 51/00*    (2006.01)
(Continued)

(52) U.S. Cl.
CPC ........ *H01L 51/0058* (2013.01); *C07C 13/573* (2013.01); *C07C 13/72* (2013.01);
(Continued)

(58) Field of Classification Search
None
See application file for complete search history.

(56) References Cited

U.S. PATENT DOCUMENTS

| 7,056,601 B2 | 6/2006 | Cosimbescu et al. |
| 2015/0108448 A1 | 4/2015 | Dai et al. |
| 2015/0144898 A1 | 5/2015 | Dai et al. |

FOREIGN PATENT DOCUMENTS

| CN | 1871324 A | 11/2006 |
| CN | 103450883 A | 12/2013 |

(Continued)

OTHER PUBLICATIONS

Machine translation of JP-2003229273-A.*
Machine translation of KR-20110081698-A.*

*Primary Examiner* — Vu A Nguyen
(74) *Attorney, Agent, or Firm* — Maschoff Brennan

(57) ABSTRACT

This invention relates to an OLED, comprising an anode, a cathode, and an organic layer, the organic layer at least contains one or more layers containing light emitting layer from the hole injection layer, hole transport layer, electron injection layer, electron transport layer, light emitting layer; the light emitting layer is a host guest doping system composed of host materials and guest materials. The light-emitting zone of the light emitting layer is blue 440-490 nm, and the host material or guest material has a structure with the formula (I). The OLED has the advantages of excellent light emitting efficiency, excellent color purity and long lifetime.

(Continued)

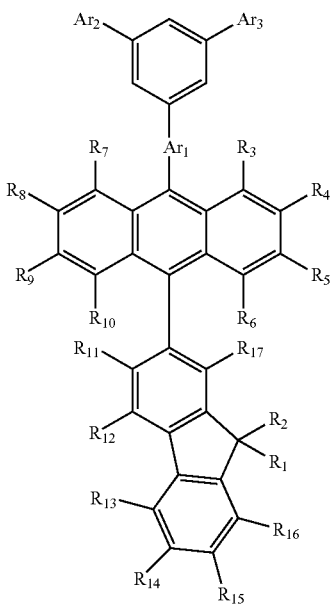

(I)

(51) Int. Cl.
- *H01L 51/50* (2006.01)
- *C07C 13/573* (2006.01)
- *C07C 13/72* (2006.01)
- *C09K 11/02* (2006.01)

(52) U.S. Cl.
CPC ........ C09K 11/025 (2013.01); H01L 51/0056 (2013.01); *C07C 2603/18* (2017.05); *C07C 2603/24* (2017.05); *C07C 2603/97* (2017.05); *H01L 51/5024* (2013.01); *H01L 51/5056* (2013.01); *H01L 51/5072* (2013.01); *H01L 51/5088* (2013.01); *H01L 51/5092* (2013.01)

(56) References Cited

FOREIGN PATENT DOCUMENTS

| | | | |
|---|---|---|---|
| CN | 103456897 A | | 12/2013 |
| JP | 2003229273 A | * | 8/2003 |
| KR | 20110081698 A | * | 7/2011 |

16 Claims, 9 Drawing Sheets

* cited by examiner

Figure 5
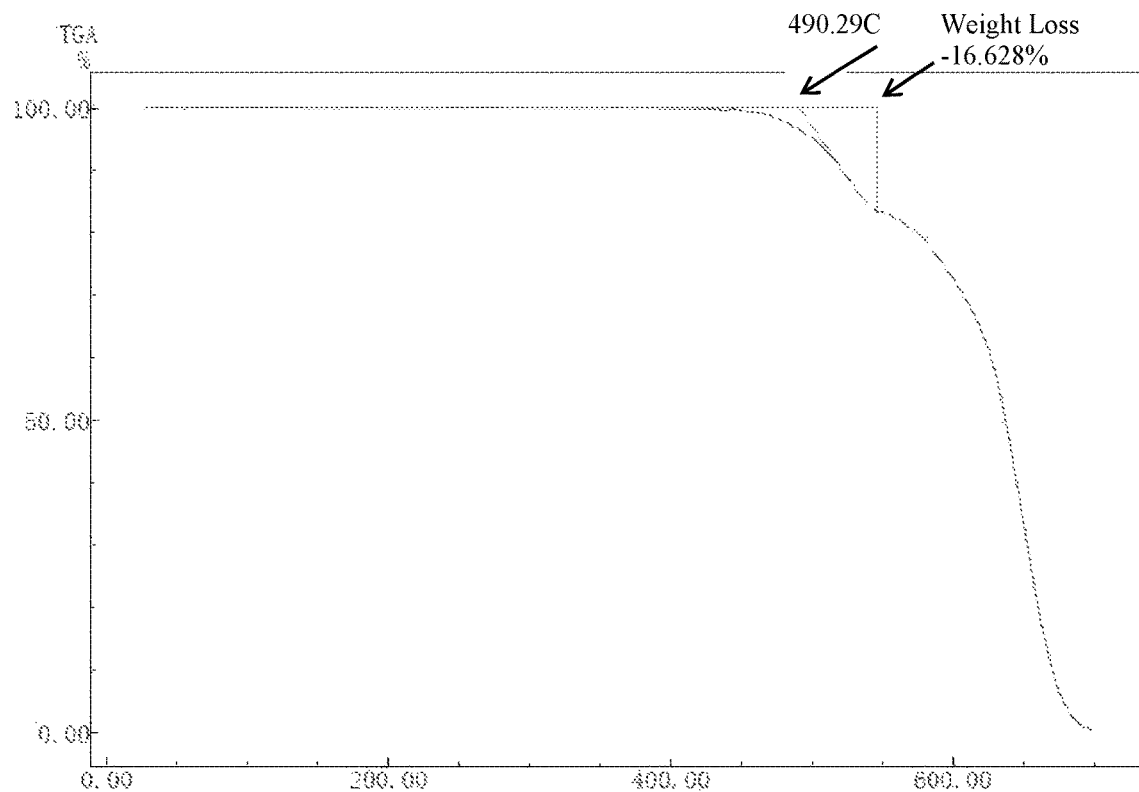
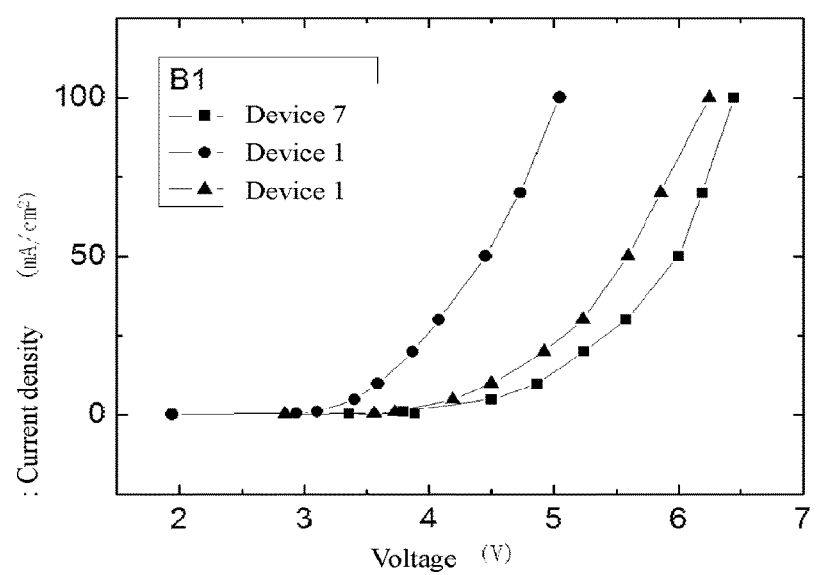
FIG.6

ORGANIC ELECTROLUMINESCENT DEVICE

TECHNICAL FIELD

This invention relates to a new type of Organic Blue-Light Emitting Device made by organic host materials. It belongs to the Organic Light-emitting Device (OLED) display material field.

BACKGROUND ART

OLED, as a new type of display technology, has unique advantages such as self-illumination, wide viewing angle, low power consumption, high efficiency, thin, rich colors, fast response, extensive application temperature, low drive voltage, used to make flexible, bendable and transparent display panel and environmental friendliness, etc. Therefore, OLED technology can be applied to flat panel displays and new generation of lighting, or can be used as backlight of LCD.

OLED is a device made through spin-coating or depositing a layer of organic material between two metal electrodes. A classic three-layer OLED comprises a hole transport layer, a light emitting layer and an electron transport layer. The holes generating from the anode through the hole transport layer and the electrons generating from the cathode through the electron transport layer combine to form excitons in the light emitting layer, emitting light. By changing the material of the light emitting layer, the OLED can emit red light, green light and blue light. Therefore, stable, efficient organic light-emitting materials with pure colors play an important role in the application and promotion of OLEDs. Meanwhile, it is also very urgent for the application and promotion of large area of panel display in OLEDs.

Among three primary colors (red, blue, green), the red and green light materials have made great development although the performance of red and green OLEDs have been dramatically enhanced, which also meet the market demands of the panels, their efficiency and stability need to be improved. Therefore, a research focus is to solve the above problems from the material design and device structure. In the dye-doped OLED, the energy transfer efficiency of the host material to the dopant has a great influence on the efficiency and stability of the device. Frequently used host materials include mCP and 26DCzPPy and their derivatives, all containing nitrogen atoms. Materials containing hydrocarbons only have relatively high relative stability and are suitable for industrial applications and commercialization. There are also a series of commercial materials for the host material of the blue fluorescent dye doping device, of which, the mostly used one early are 9,10-diphenylanthracene (DPA), 9,10-bis (naphthalen-2-yl) anthracene (ADN) and 2-methyl-9,10-bis (naphthalen-2-yl) anthracene (MADN). Devices made of this type of compounds have ordinary efficiency, and due to its easy crystallization produced by symmetry of molecules, the thin film form is easy to change, which reduces the device stability, thus, it cannot be widely used in the OLED industry.

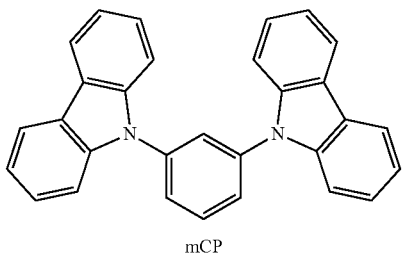

mCP

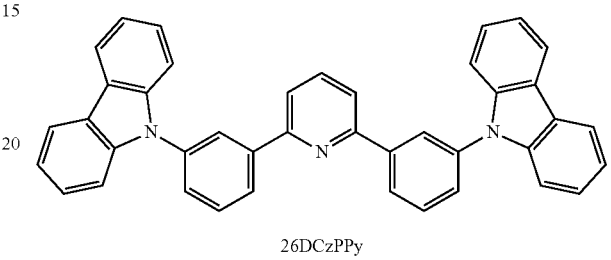

26DCzPPy

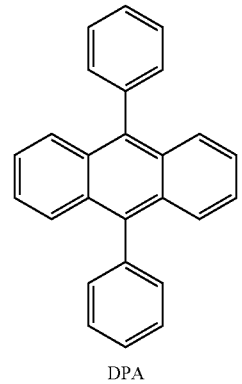

DPA

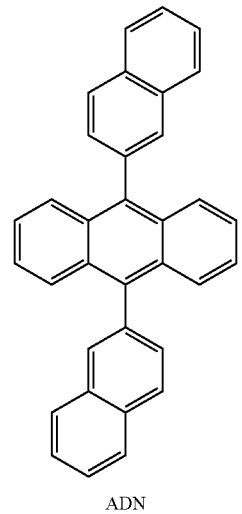

ADN

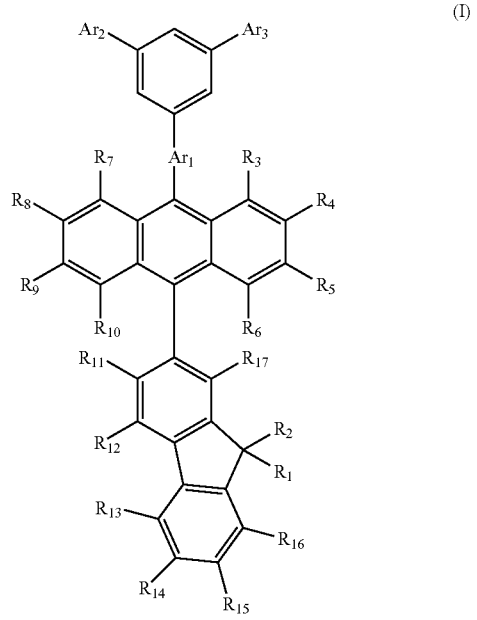

MADN

SUMMARY OF THE INVENTION

The present invention is to overcome the drawbacks of the above devices and to provide an organic electroluminescent dye-doped blue light emitting device with excellent light emitting efficiency and excellent color purity and long lifetime.

An OLED comprises an anode, a cathode, and an organic layer, the organic layer at least contains one or more layer containing light emitting layer from the hole injection layer, hole transport layer, electron injection layer, electron transport layer, light emitting layer; the light emitting layer is a host guest doping system composed of host materials and guest materials. The light-emitting zone of the light emitting layer is blue 440-490 nm, and the host material or guest material has a structure with the formula (I), (I)

Wherein $R_1$-$R_{17}$ independently represent hydrogen, deuterium, halogen, cyano, nitro, C1-C8 alkyl, C1-C8 alkoxy, C6-C30 substituted or unsubstituted aryls, C3-C30 substituted or unsubstituted aryls containing one or more heteroatoms, C2-C8 substituted or unsubstituted alkenyl, C2-C8 substituted or unsubstituted alkynyl, wherein $Ar_1$-$Ar_3$ independently represent C6-C60 substituted or unsubstituted aryl, C3-C60 substituted or unsubstituted heteroaryl containing one or more heteroatoms, triaryl (C6-C30) amine.

Preferably, wherein $R_1$-$R_{17}$ independently represent hydrogen, halogen, cyano, nitro, C1-C8 alkyl, C1-C8 alkoxy, C2-C8 substituted or unsubstituted alkenyl, C2-C8 substituted or an unsubstituted alkynyl, C1-C4 alkyl substituted or unsubstituted phenyl, C1-C4 alkyl substituted or unsubstituted naphthyl, or combined C1-C4 alkyl substituted or unsubstituted fluorenyl; $Ar_1$-$Ar_3$ independently represent C1-C4 alkyl or C6-C30 aryl-substituted phenyl, C1-C4 alkyl or C6-C30 aryl-substituted naphthyl, phenyl, naphthyl, pyridyl, N—C6-C30 aryl or C1-C4 alkyl-substituted carbazolyl, dibenzothienyl, dibenzofuranyl, anthryl, phenanthryl, pyrenyl, perylenyl, fluoranthenyl, (9,9)-dialkyl) fluorenyl, (9,9-dialkyl substituted or unsubstituted aryl) fluorenyl, 9,9-spirofluorenyl.

Preferably, wherein $R_1$-$R_2$ independently and preferably represent hydrogen, halogen, C1-C4 alkyl, C1-C4 alkyl substituted or unsubstituted phenyl, C1-C4 alkyl substituted or unsubstituted naphthyl, or combined C1-C4 alkyl-substituted or unsubstituted fluorenyl; wherein $R_3$-$R_{17}$ may independently represent hydrogen, halogen, C1-C4 alkyl, C1-C4 alkyl substituted or unsubstituted phenyl, C1-C4 alkyl-substituted or unsubstituted naphthyl, preferably $Ar_1$-$Ar_3$ independently represent phenyl, tolyl, xylyl, t-butylphenyl, naphthyl, pyridyl, methyl naphthalene, biphenyl, diphenylphenyl, naphthylphenyl, diphenylbiphenyl, diarylamine phenyl, N-phenylcarbazolyl, (9,9-dialkyl) fluorenyl, (9,9-dialkyl substituted or unsubstituted phenyl) fluorenyl, 9,9-spirofluorenyl.

Preferably, wherein $R_3$-$R_{17}$ preferably represents hydrogen, and $R_1$ and $R_2$ may independently represent hydrogen, methyl, ethyl, propyl, isopropyl, t-butyl, phenyl, biphenyl, naphthyl, or combined fluorenyl; $Ar_1$-$Ar_3$ may independently represent phenyl, pyridyl, tolyl, xylyl, naphthyl, methylnaphthalene, biphenyl, diphenylphenyl, naphthylphenyl, diphenylbiphenyl, (9,9-dialkyl) fluorenyl, (9,9-dimethyl-substituted or unsubstituted phenyl) fluorenyl, 9,9-spirofluorenyl.

Preferably, $R_3$-$R_{17}$ represent hydrogen preferably; $R_1$, $R_2$ independently represent hydrogen, methyl or combined fluorenyl; $Ar_1$, $Ar_2$, $Ar_3$ independently represent phenyl and naphthyl.

Preferably, the compounds with formula (I) have following structures

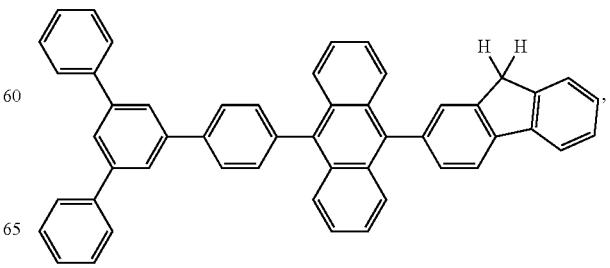

-continued

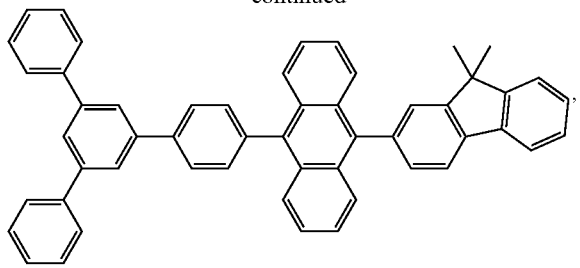

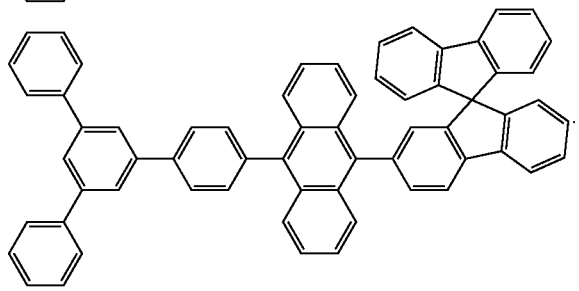

The said multiple organic layers are one or more layers from hole injection layer, hole transport layer, light emitting layer, hole blocking layer, electron transport layer, and in particular, not all organic layers are necessary according to the demands.

The said hole transport layer, electron transport layer and/or light emitting layer contain the said compound with the structural formula (I).

The compound with the structural formula (I) is located in the light emitting layer.

The OLED in the invention at least contains a light emitting layer, and the light emitting zone of the light emitting layer is blue 440-490 nm.

The light emitting layer is a host guest doping system composed of host material and guest material.

The compound with the structural formula (I) is a host material and/or a guest material.

In the doping system, the concentration of the host material is 20-99.9% of the whole light emitting layer in weight, preferably 80-99%, more preferably 90-99%. Correspondingly, the concentration of the guest material is 0.01-80% of the whole light emitting layer in weight, preferably 1-20%, more preferably 1-10%.

The total thickness of the organic layer of electronic device in the present invention is 1-1000 nm, preferably 1-500 nm, more preferably 50-300 nm.

The organic layer can form a thin film by vacuum coating or spin-coating.

As mentioned above, the compounds of formula (I) of the present invention are as follows, but are not limited to, the listed structures:

1

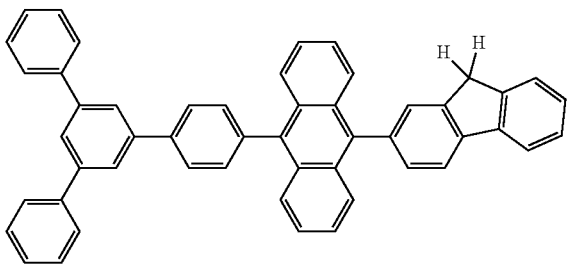

2

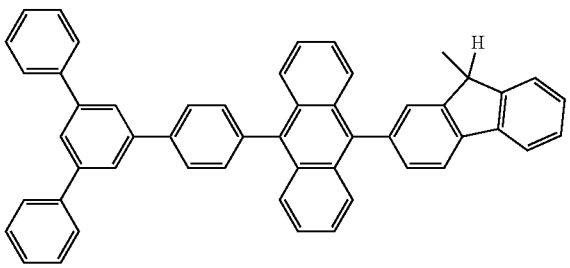

3

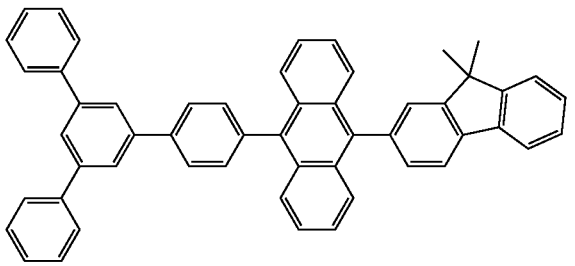

4

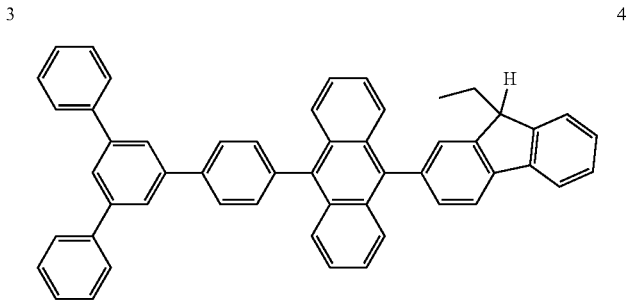

5

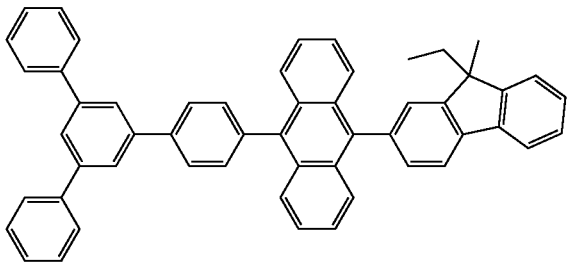

6

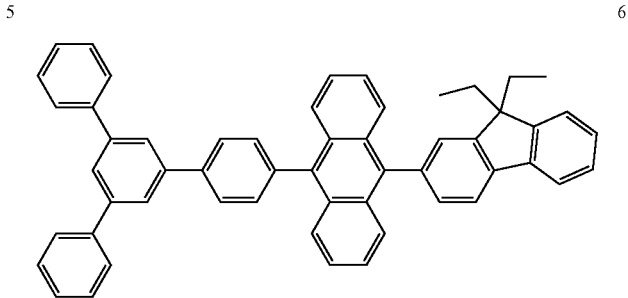

-continued
7
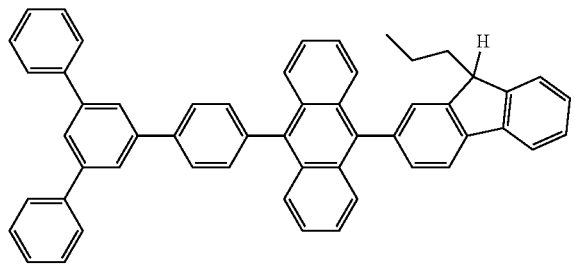
8
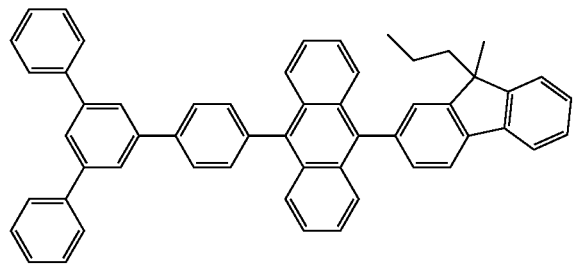
9
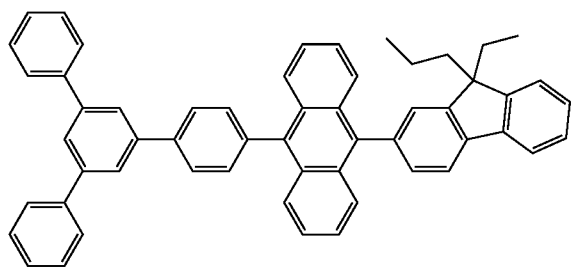
10
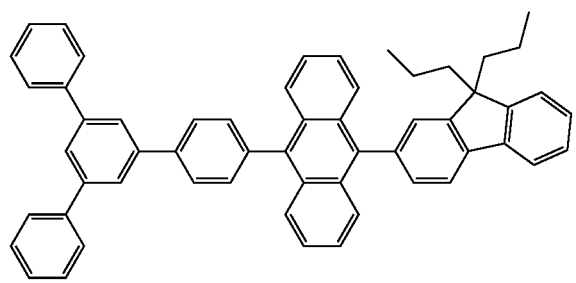
11
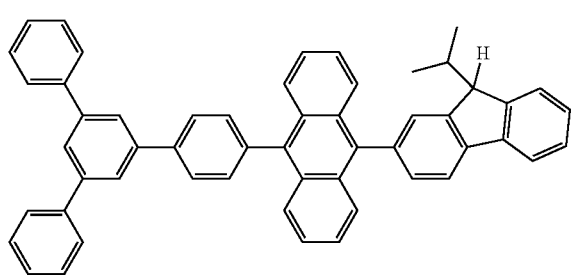
12
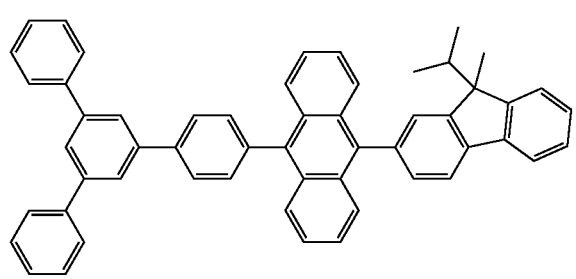
13
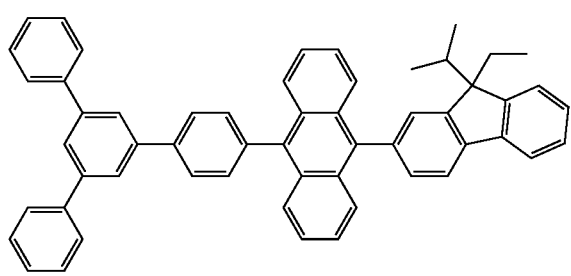
14
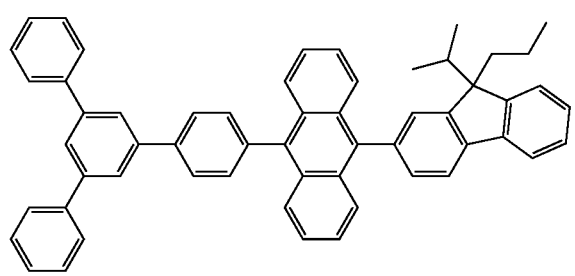
15
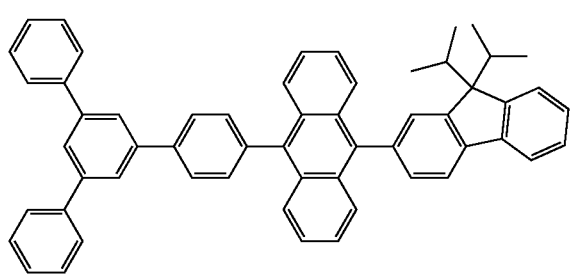
16
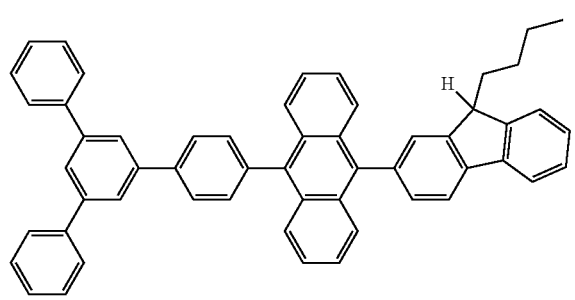

-continued
17
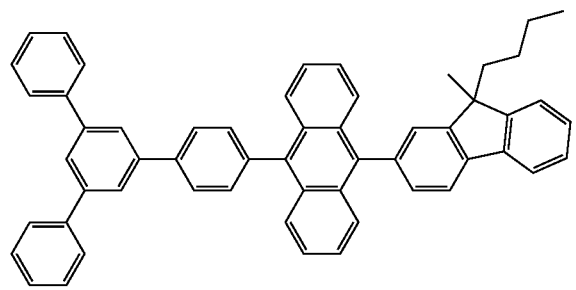
18
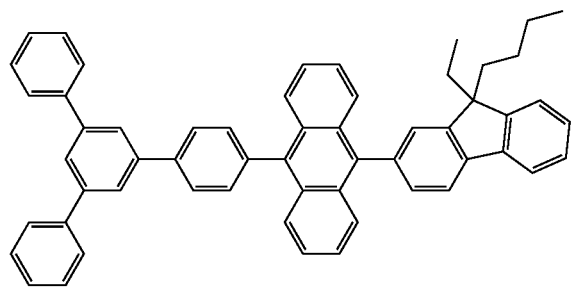
19
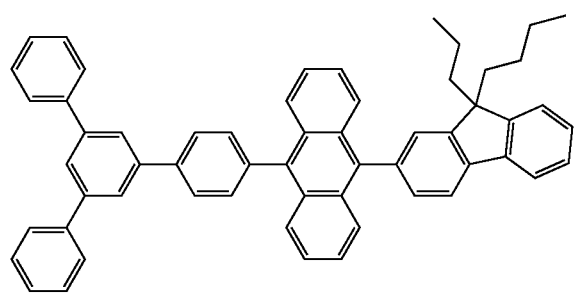
20
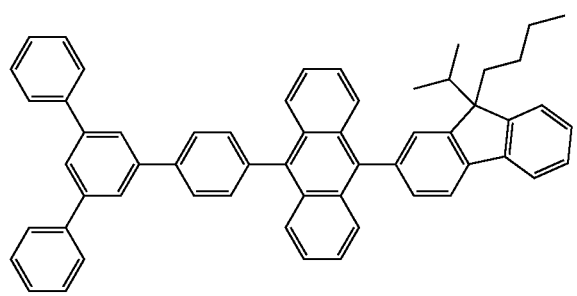
21
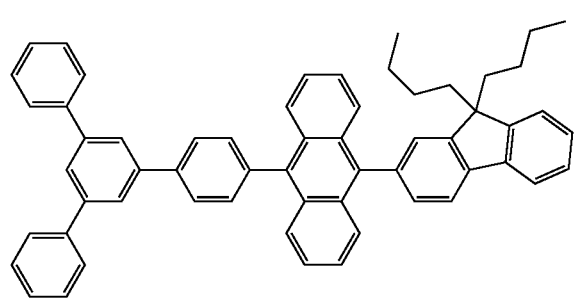
22
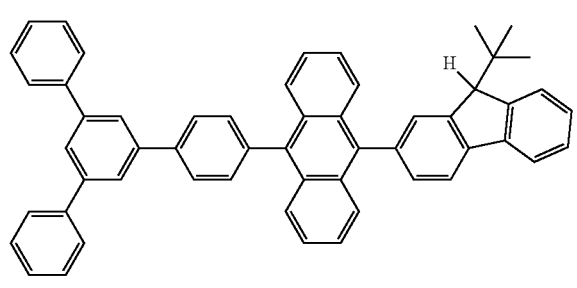
23
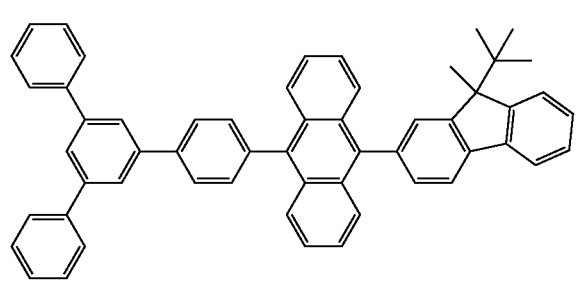
24
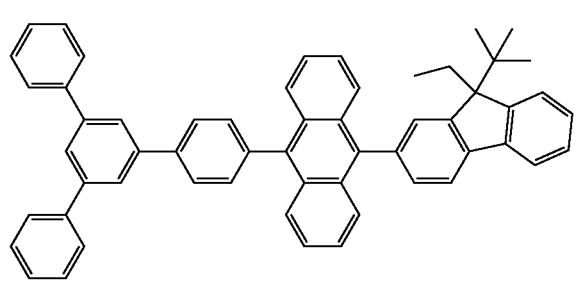
25
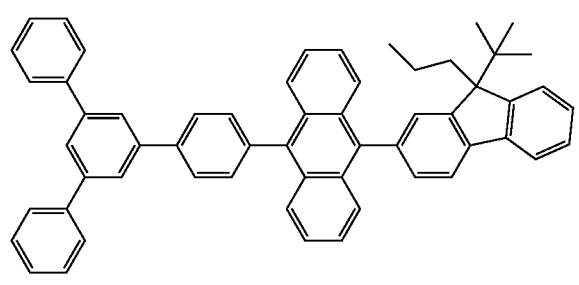
26
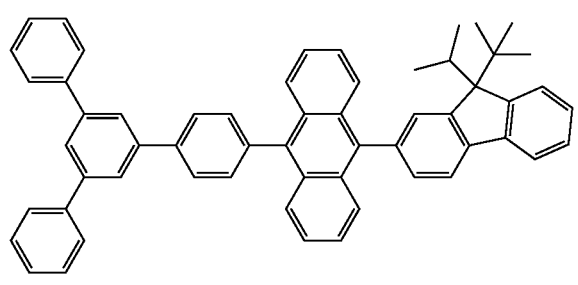

-continued
27
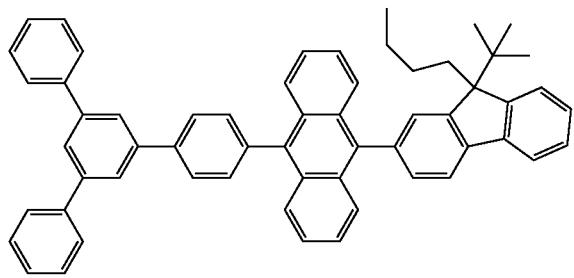
28
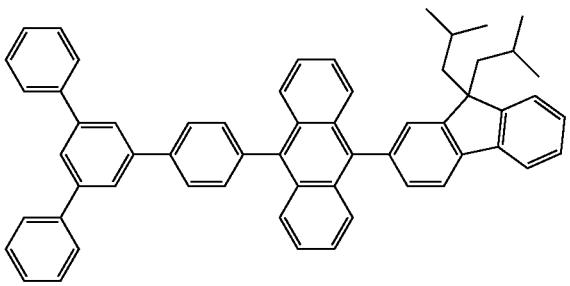
29
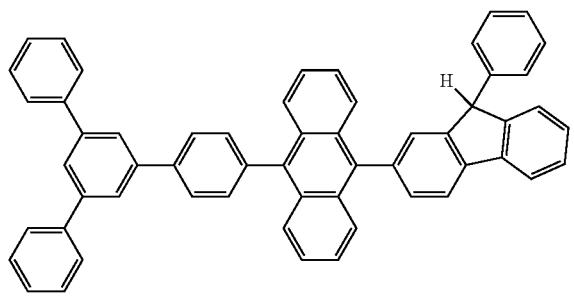
30
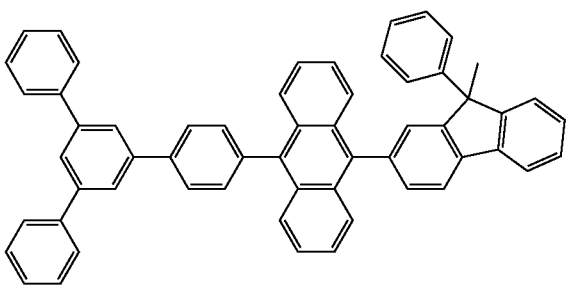
31
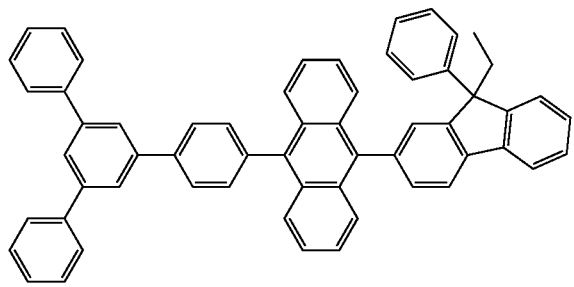
32
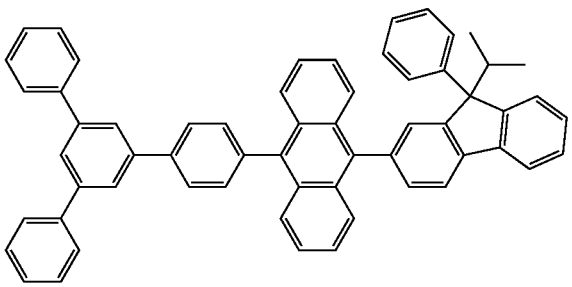
33
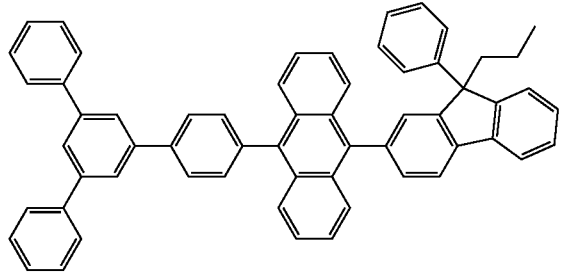
34
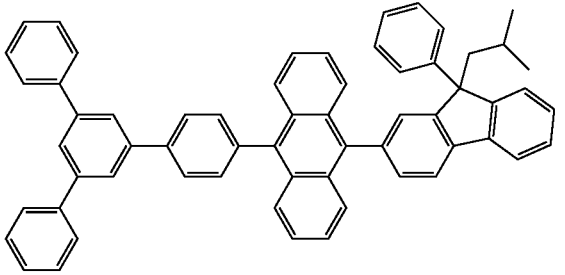
35
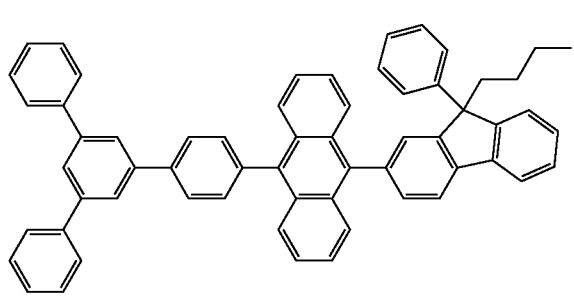
36
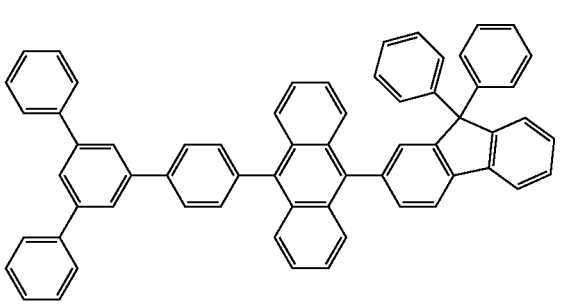

-continued
37
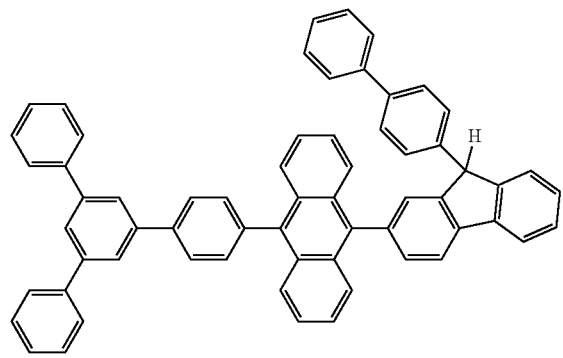
38
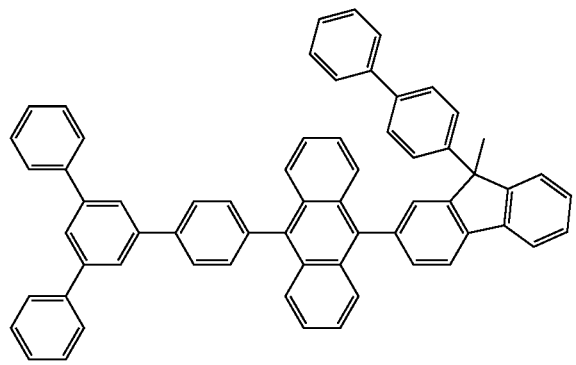
39
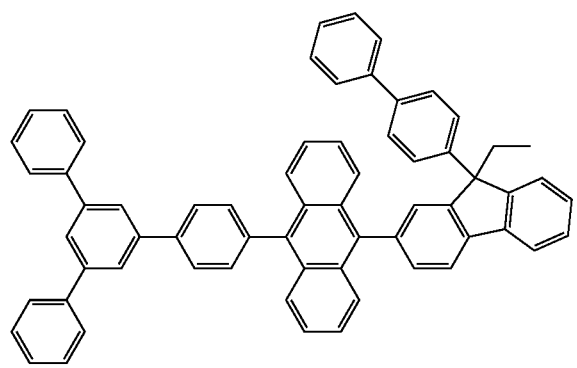
40
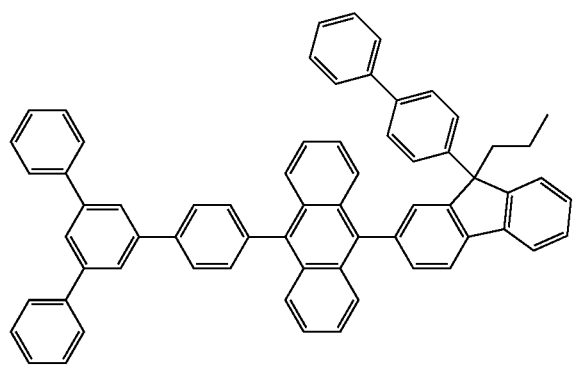
41
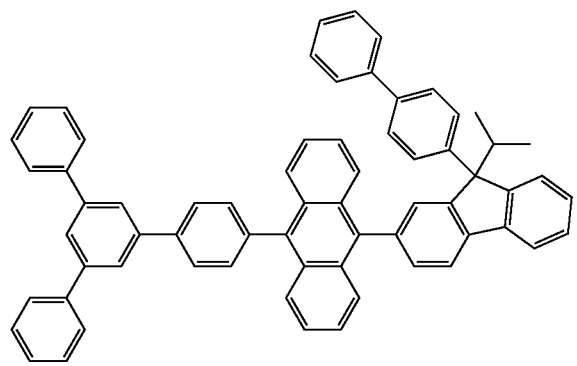
42
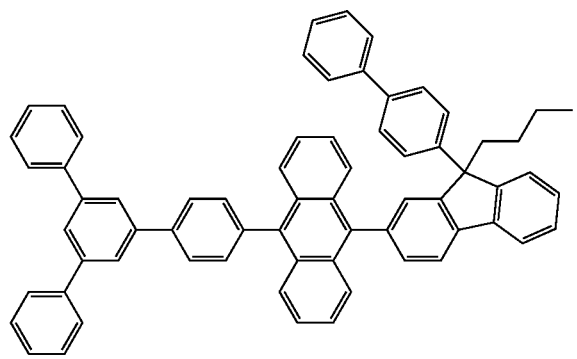
43
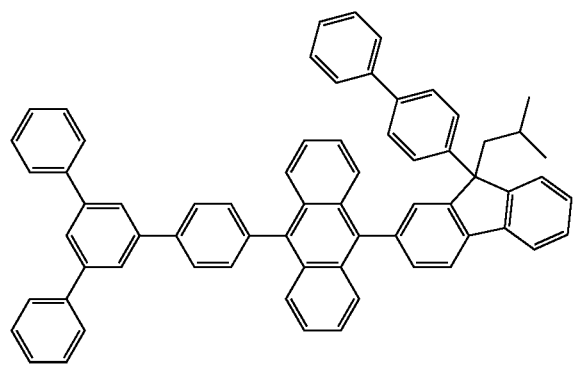
44
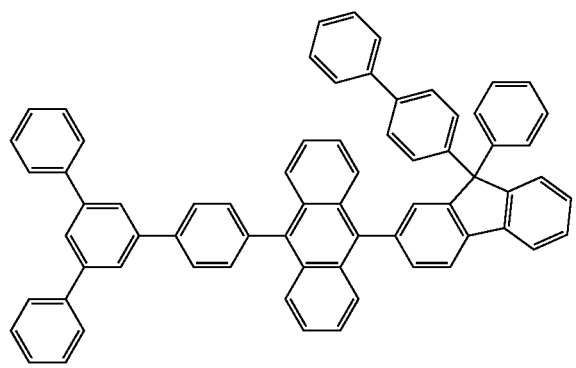

-continued
45
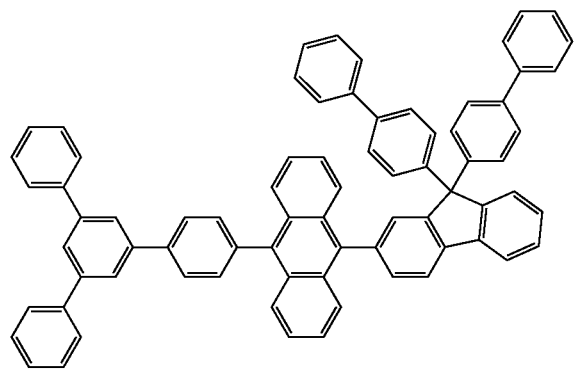
46
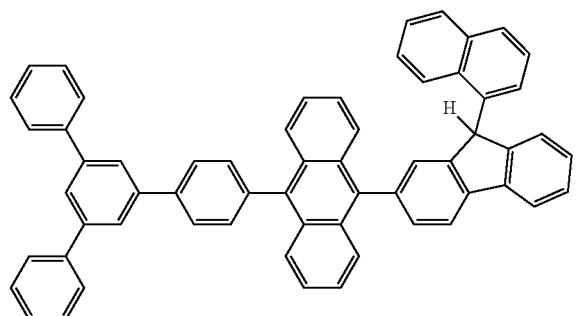
47
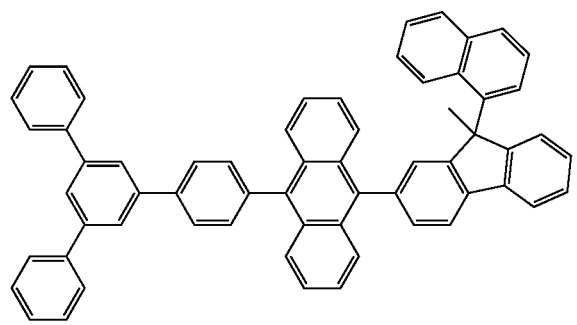
48
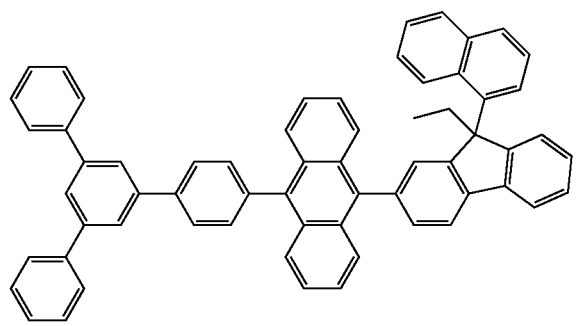
49
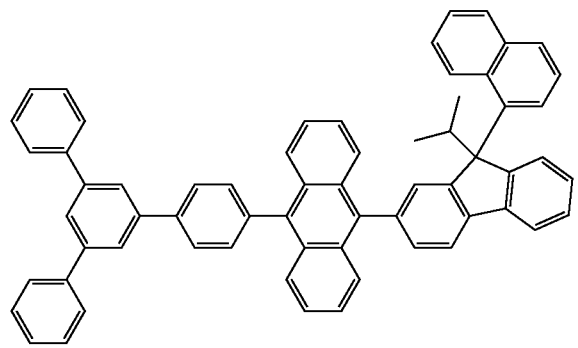
50
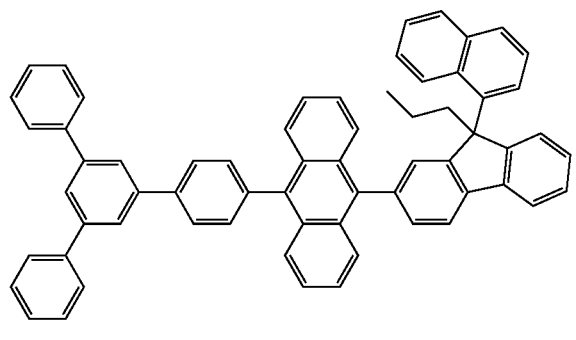
51
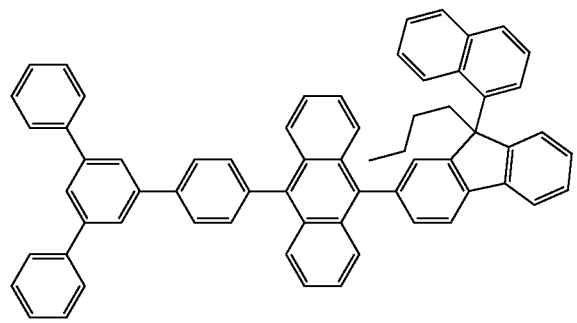
52
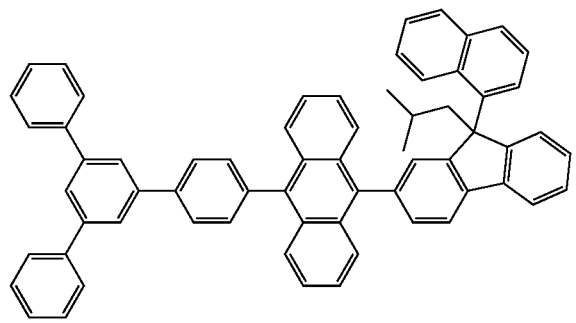

-continued
53
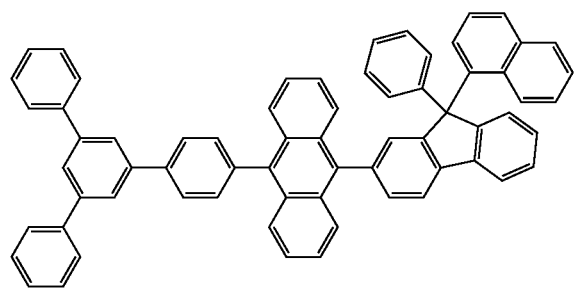
54
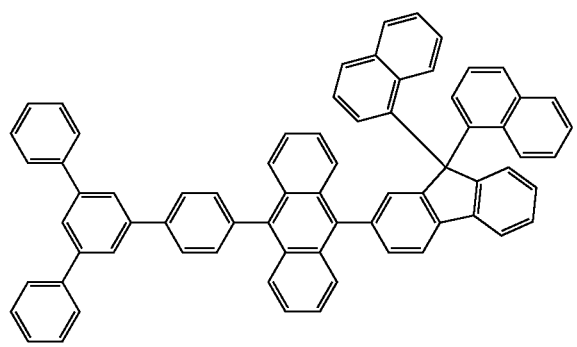
55
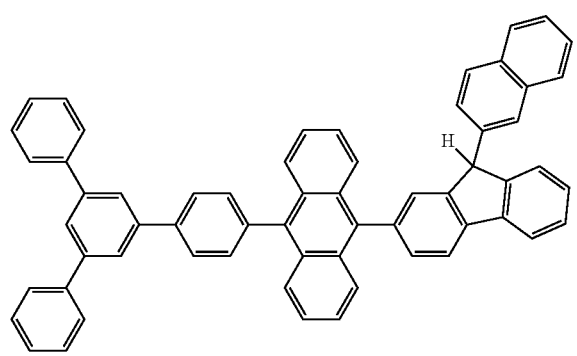
56
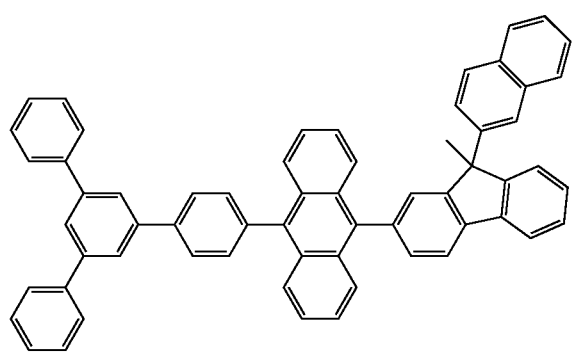
57
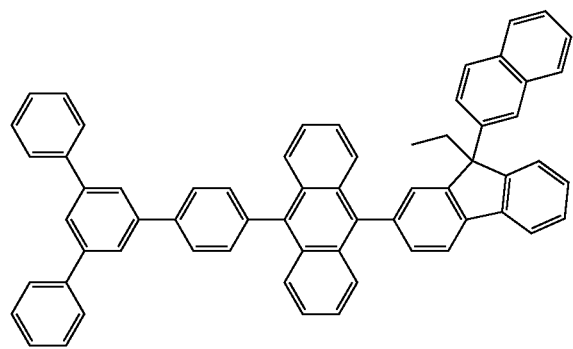
58
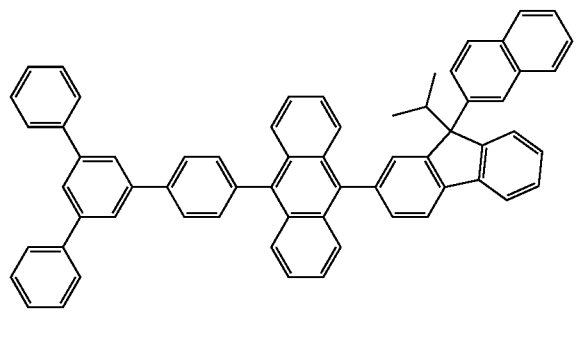
59
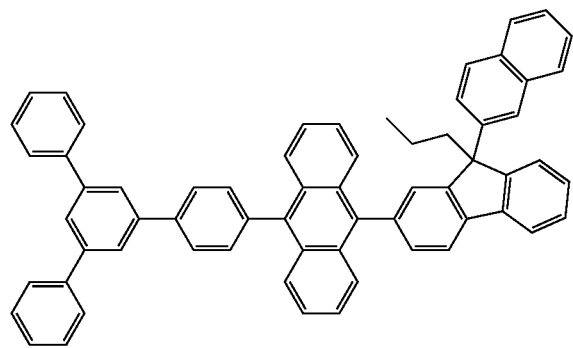
60
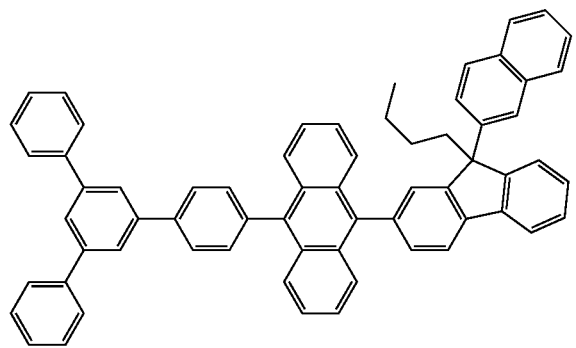

-continued
61
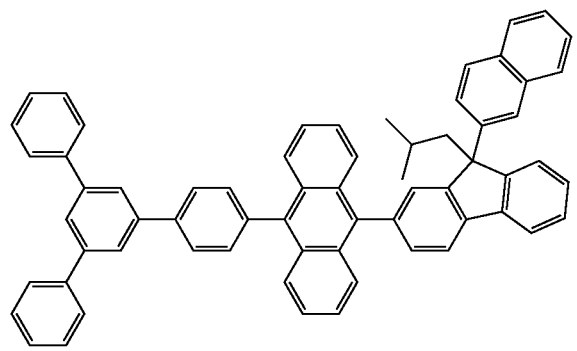
62
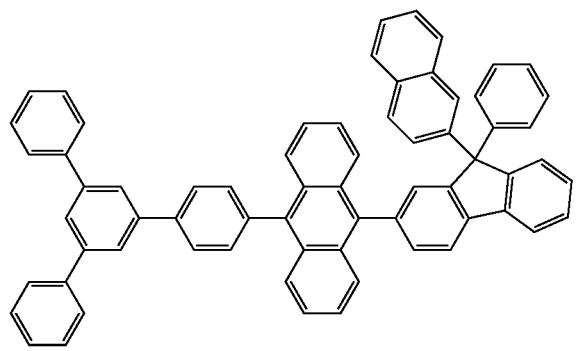
63
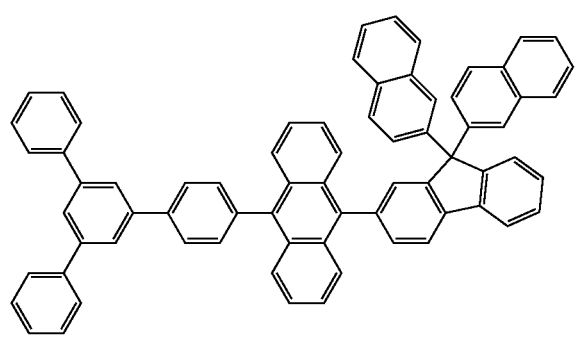
64
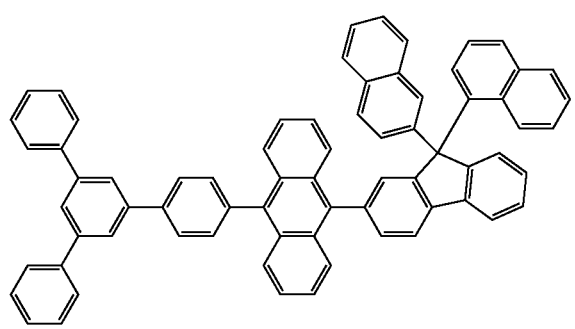
65
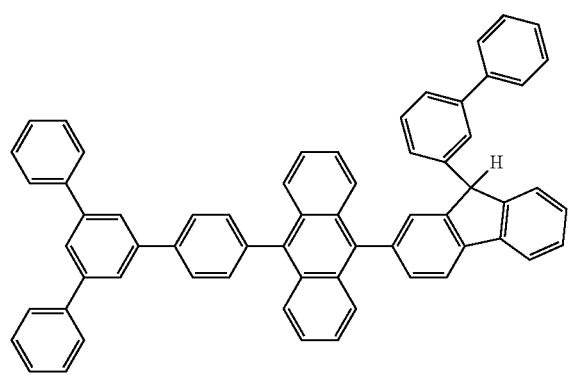
66
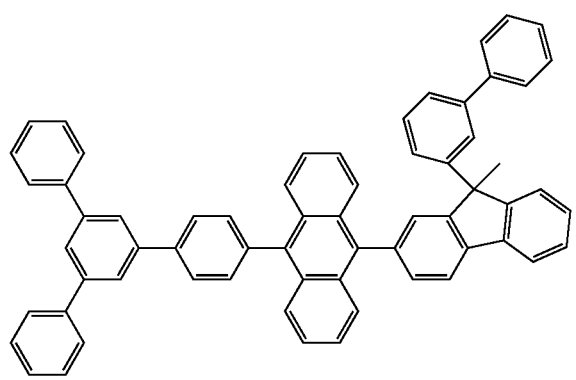
67
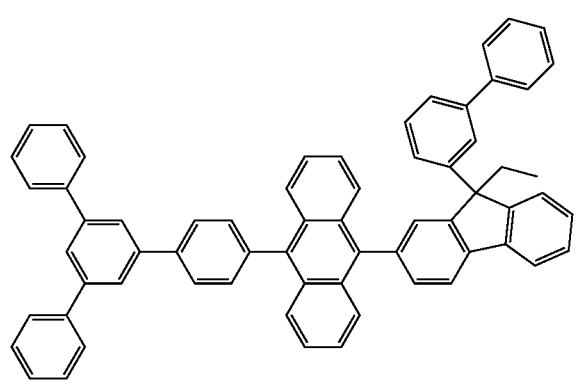
68
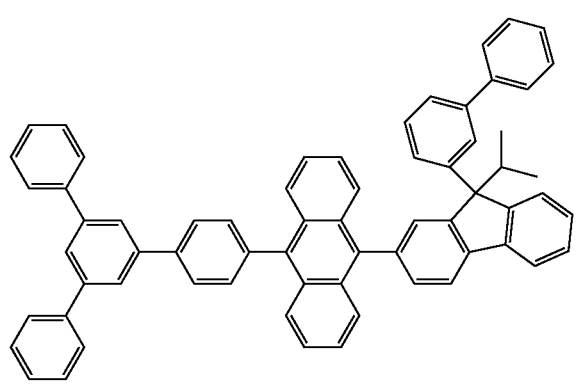

-continued
69
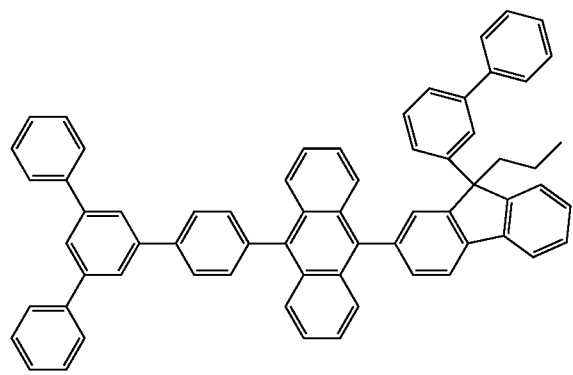
70
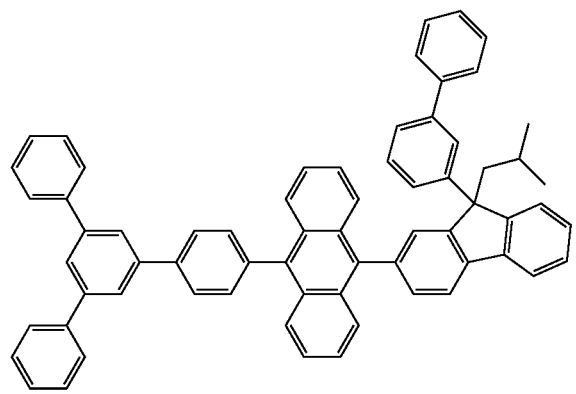
71
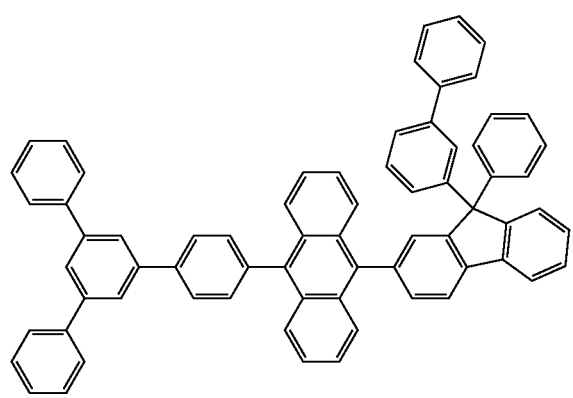
72
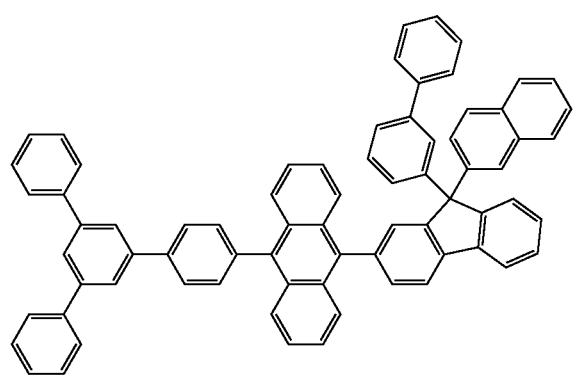
73
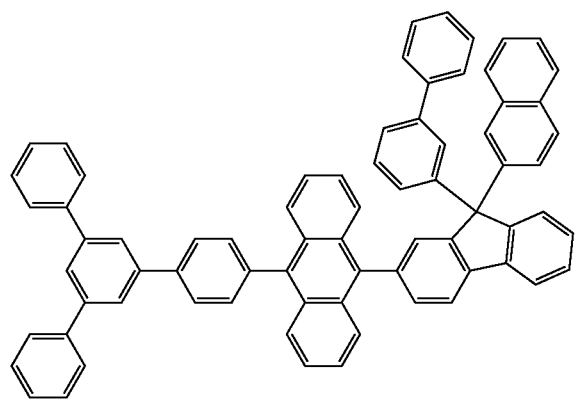
74
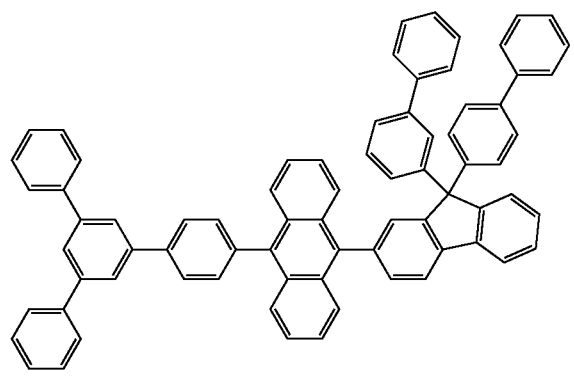
75
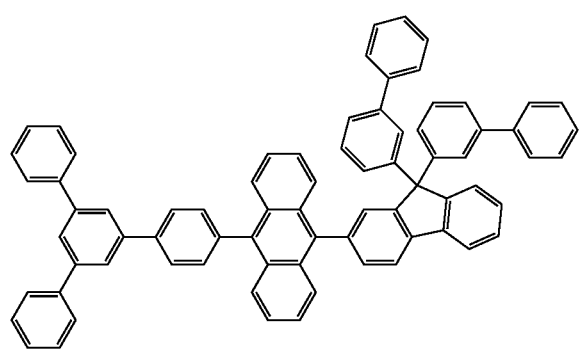
76
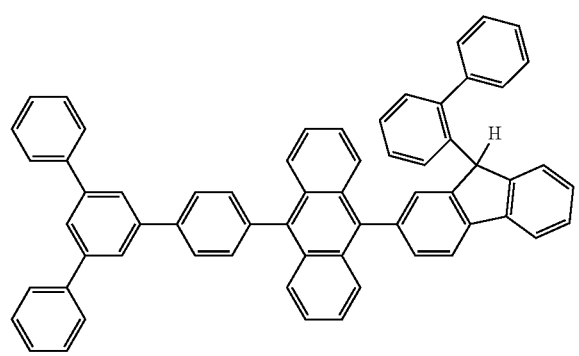

-continued
77
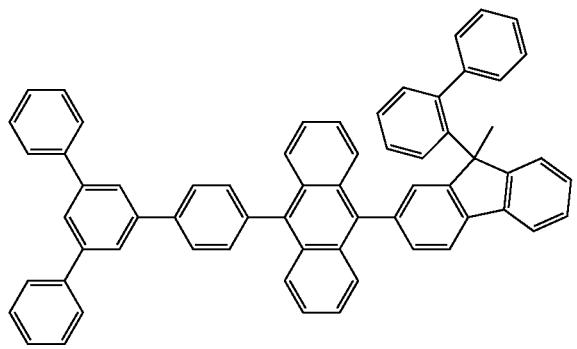
78
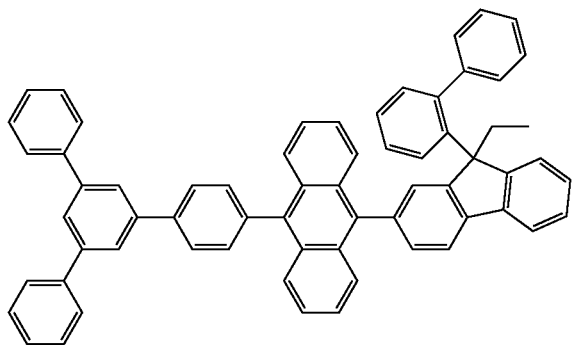
79
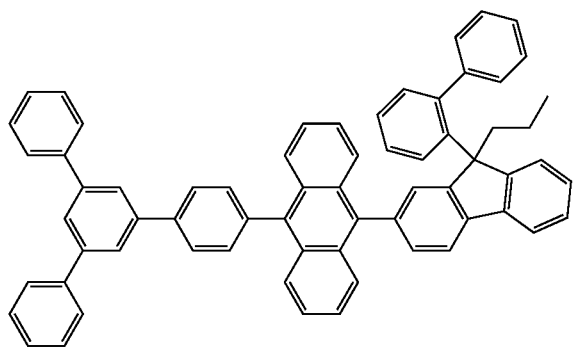
80
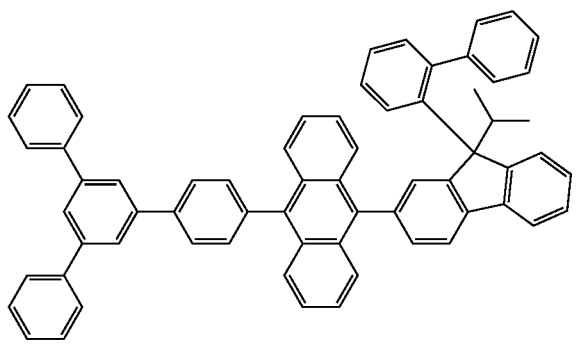
81
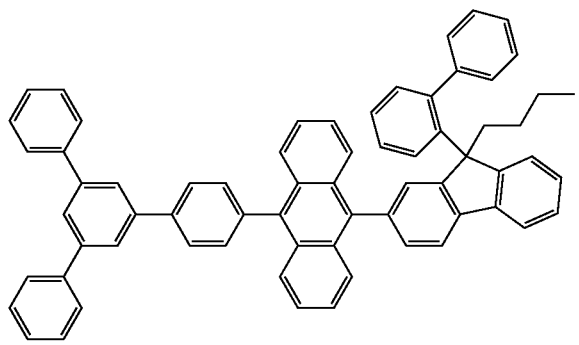
82
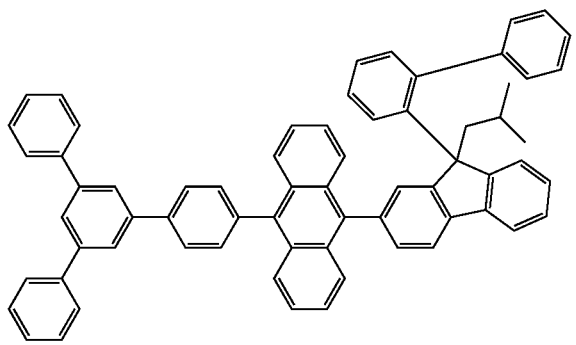
83
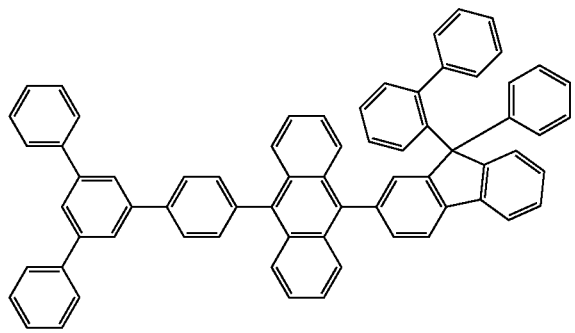
84
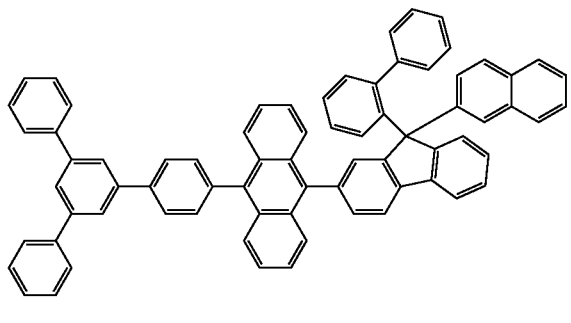

-continued
85
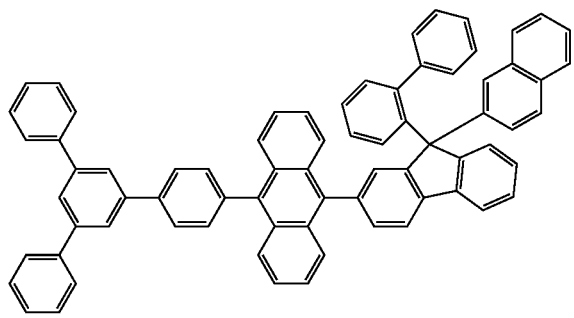
86
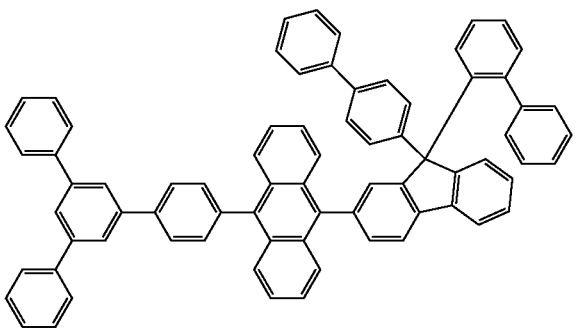
87
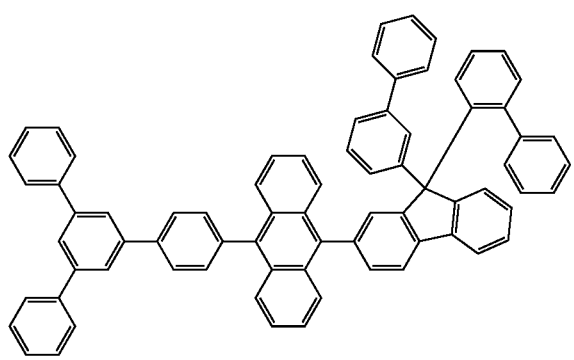
88
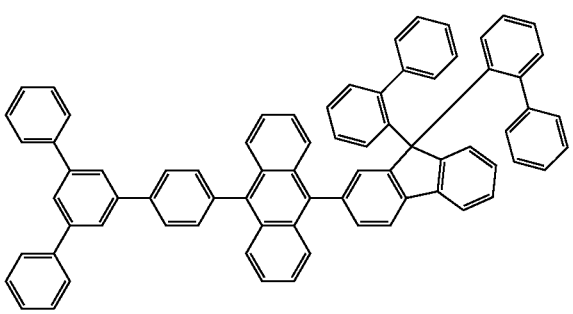
89
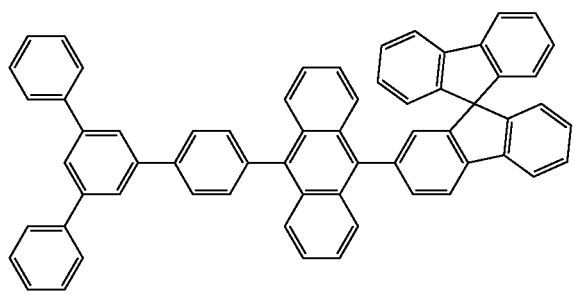
90
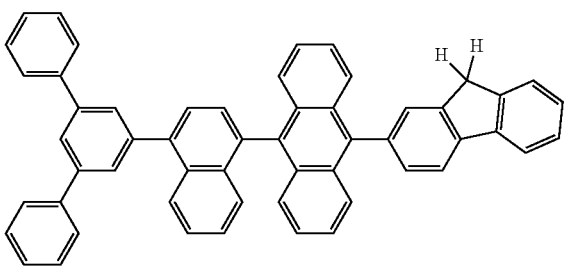
91
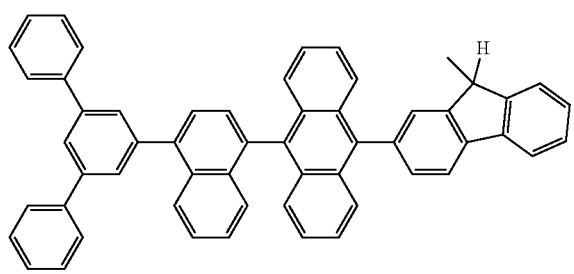
92
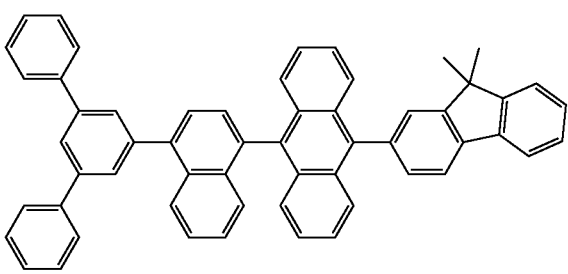
93
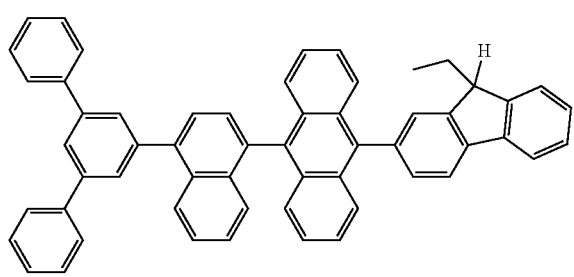
94
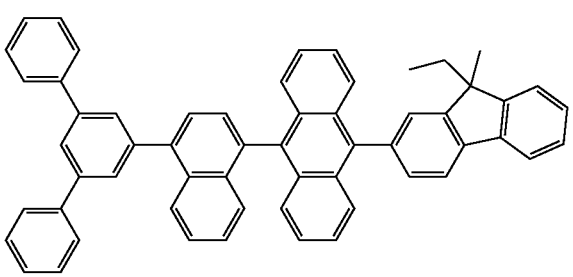

-continued
95
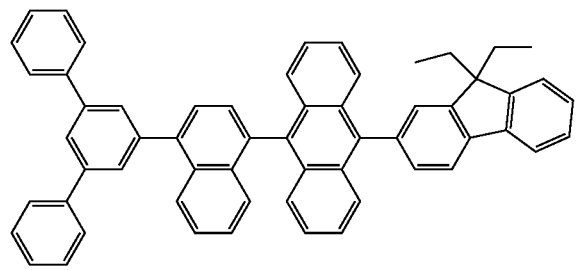
96
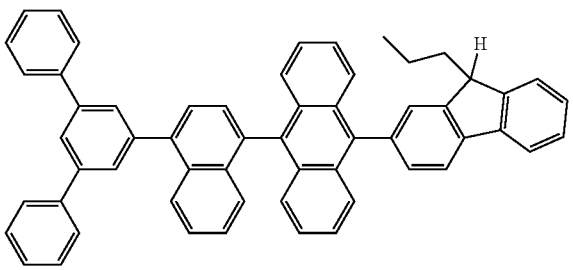
97
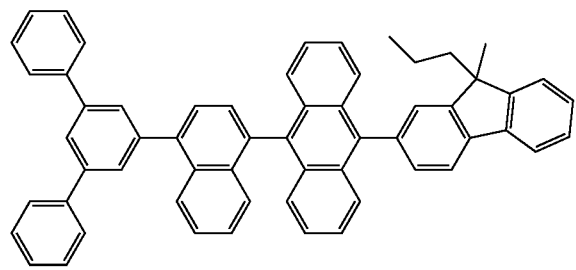
98
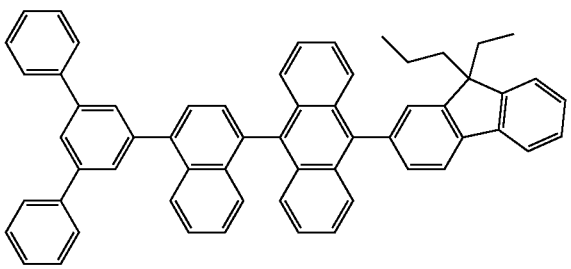
99
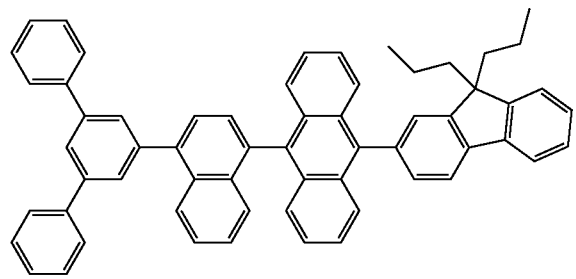
100
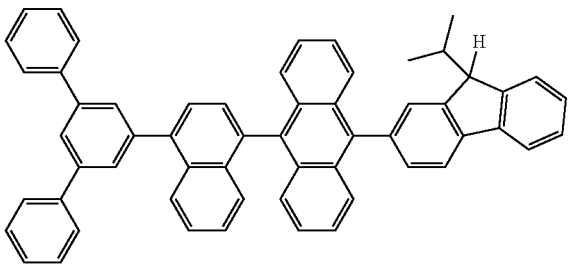
101
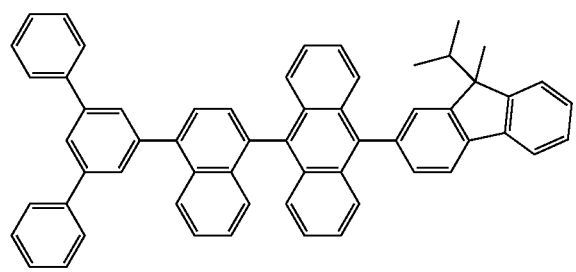
102
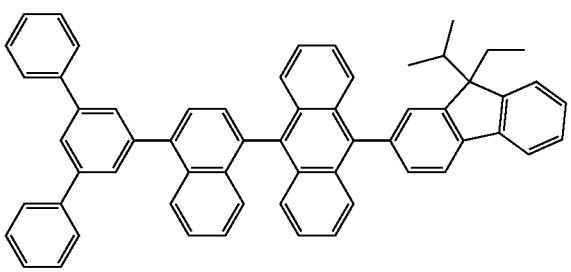
103
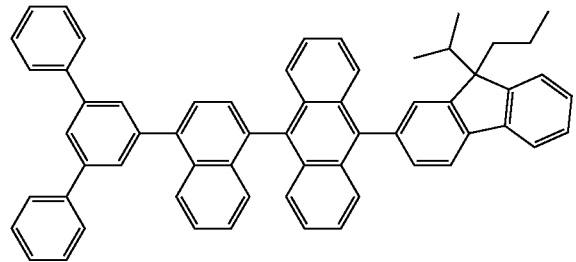
104
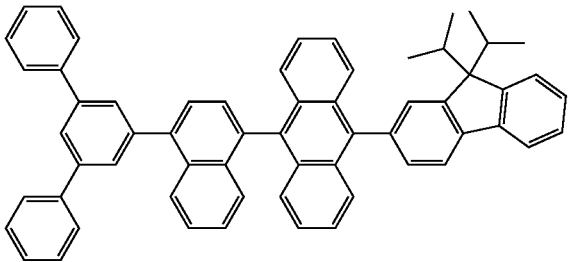

-continued
105
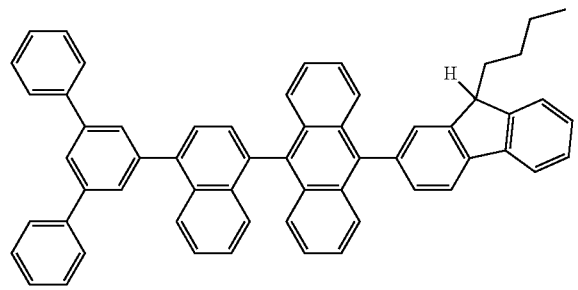
106
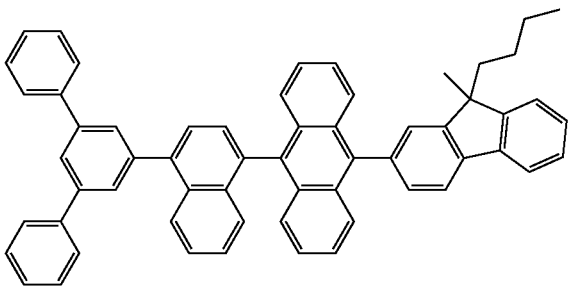
107
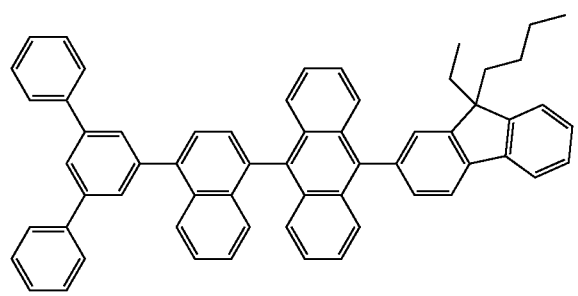
108
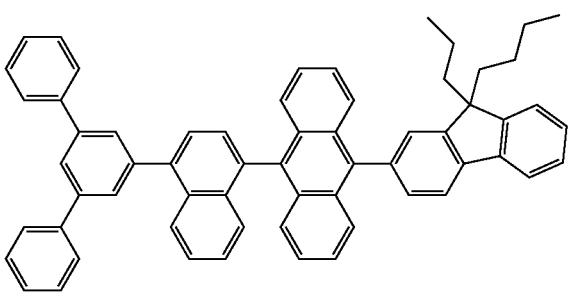
109
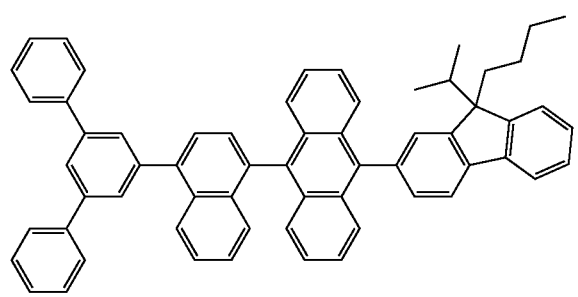
110
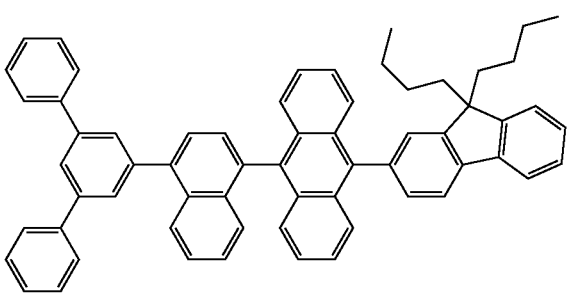
111
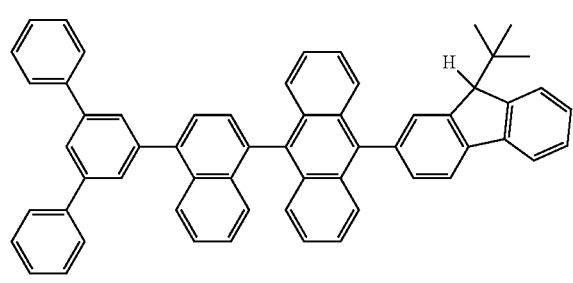
112
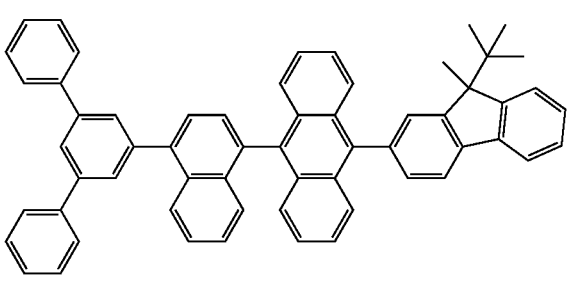
113
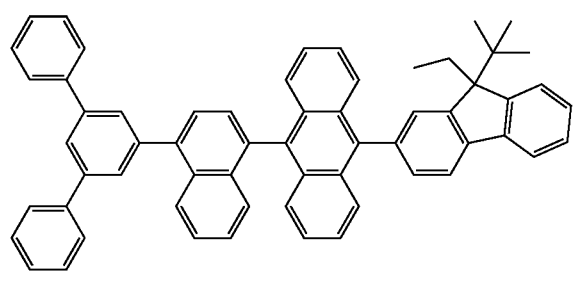
114
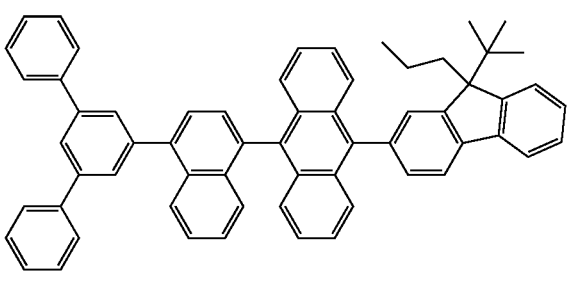

-continued
115
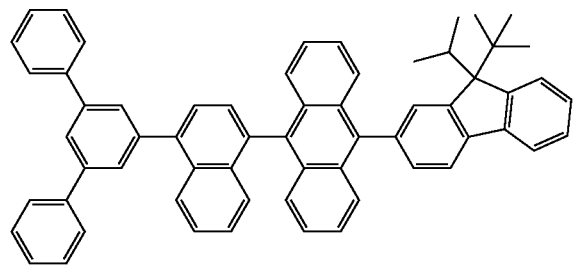
116
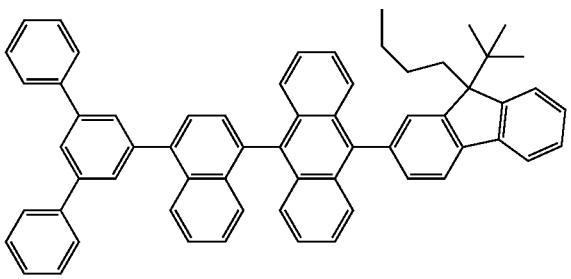
117
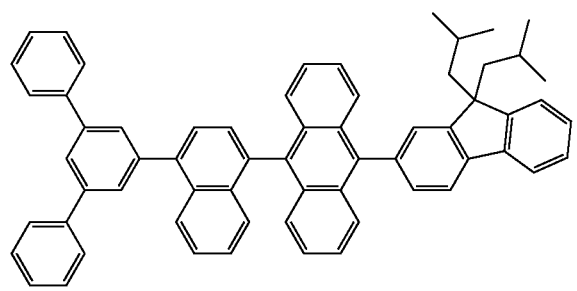
118
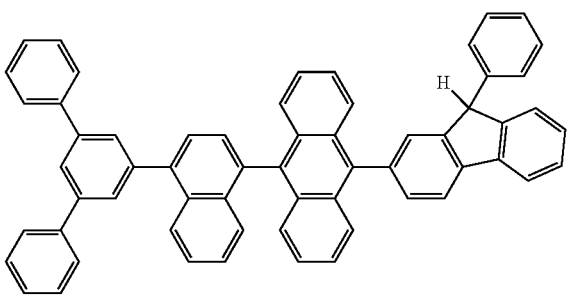
119
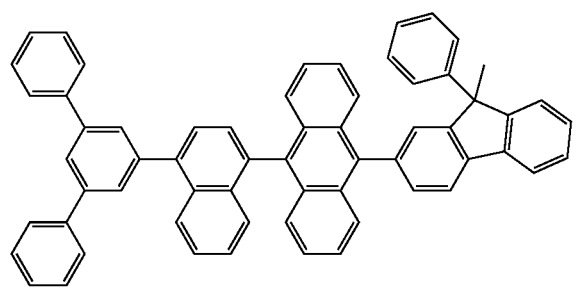
120
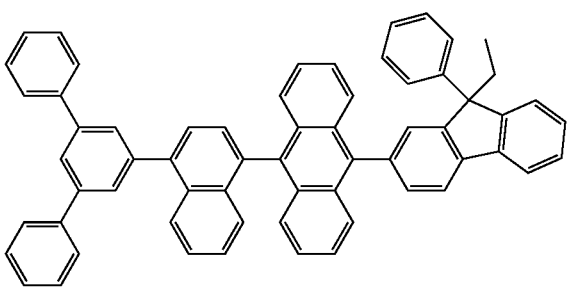
121
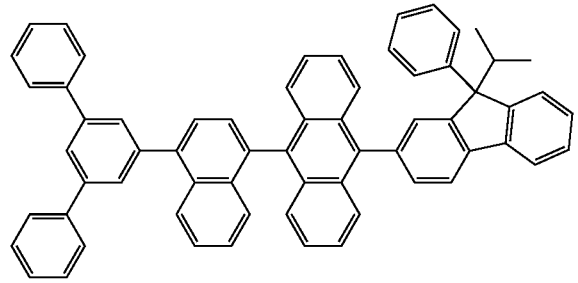
122
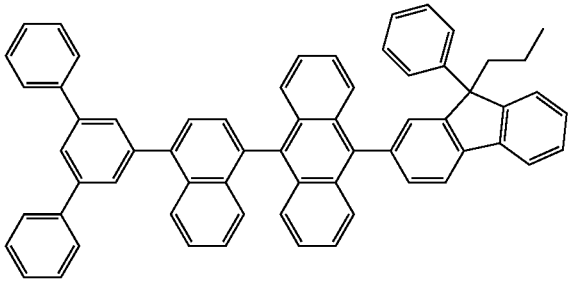
123
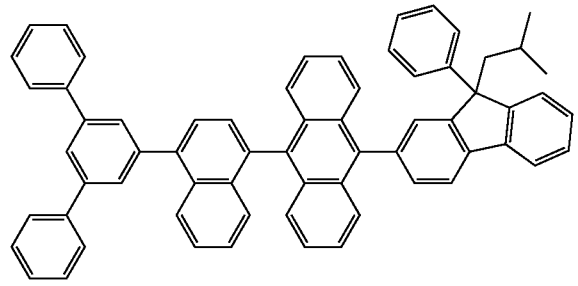
124
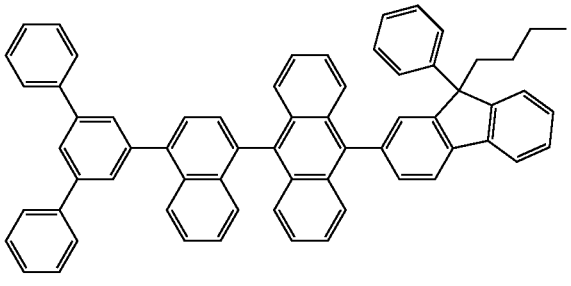

-continued
125
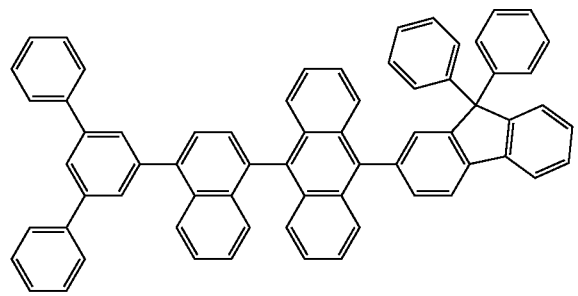
126
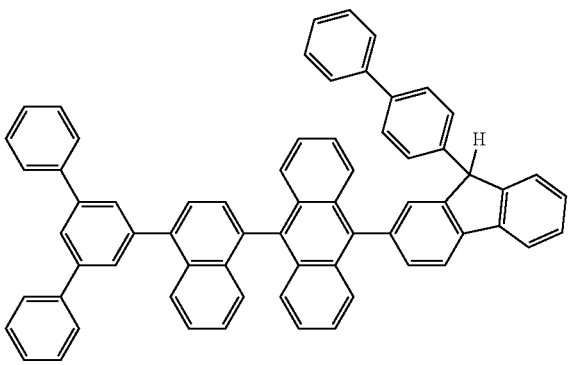
127
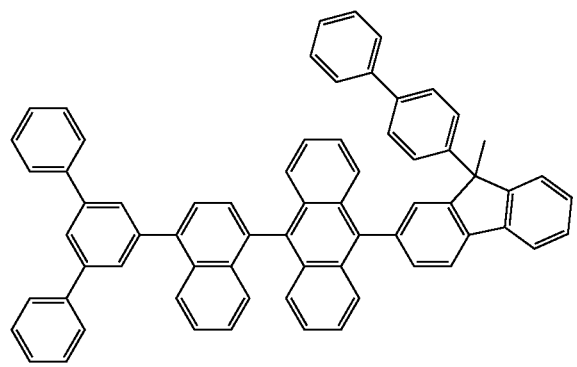
128
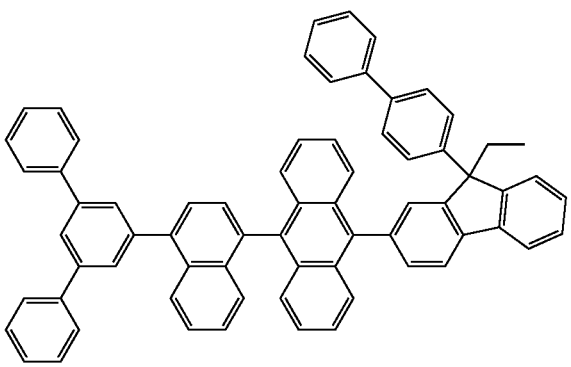
129
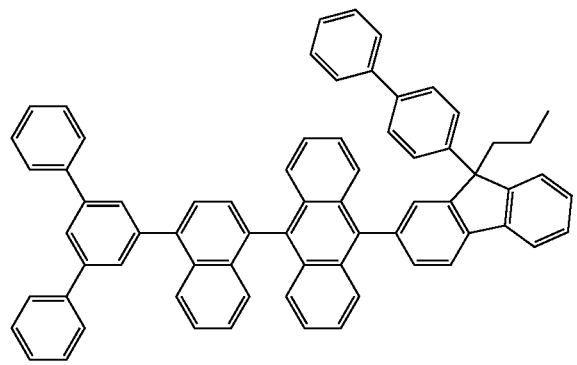
130
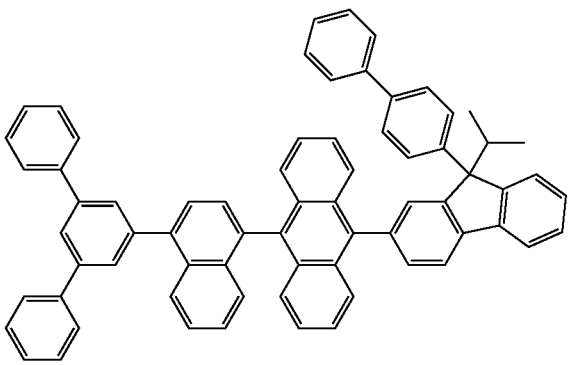
131
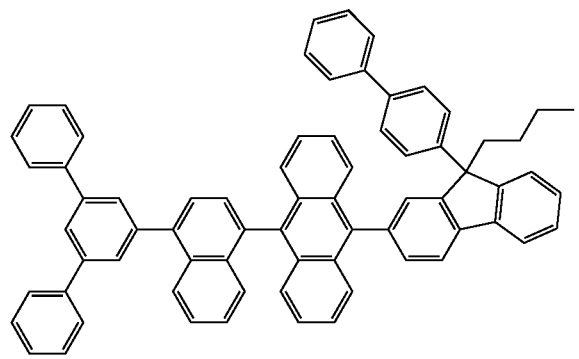
132
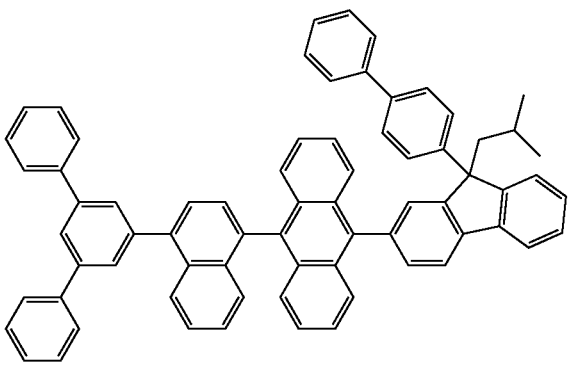

-continued
133
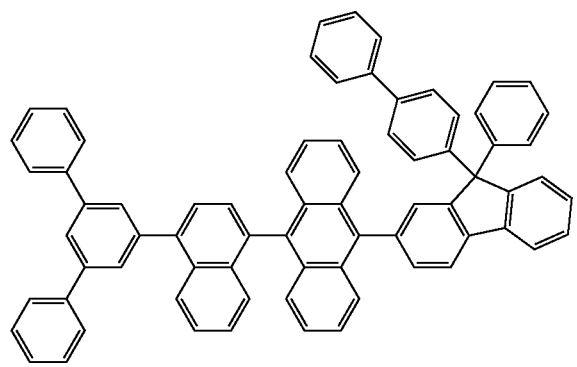
134
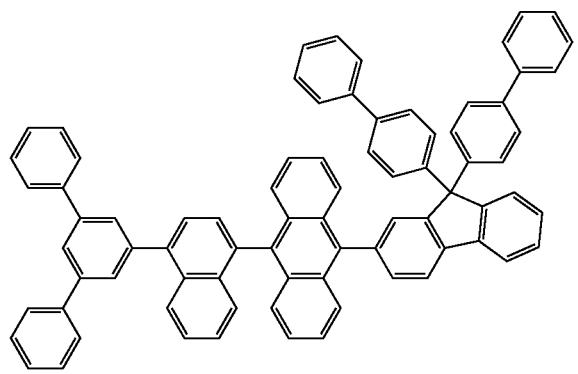
135
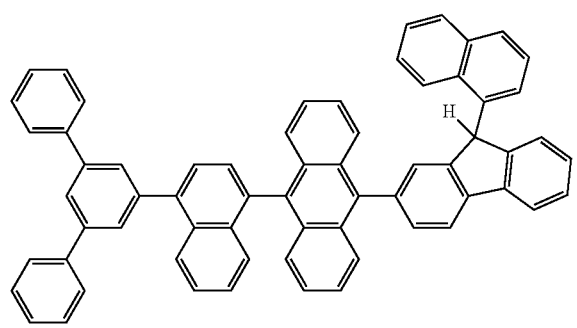
136
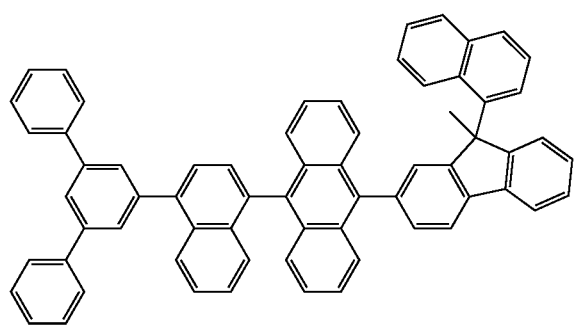
137
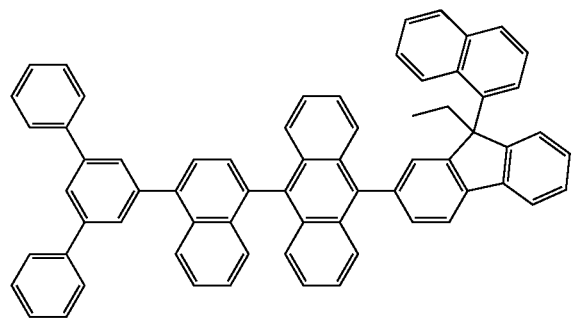
138
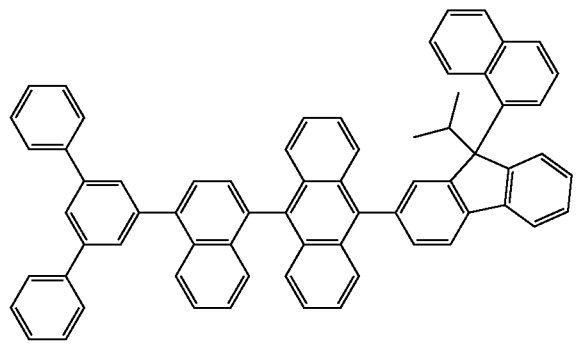
139
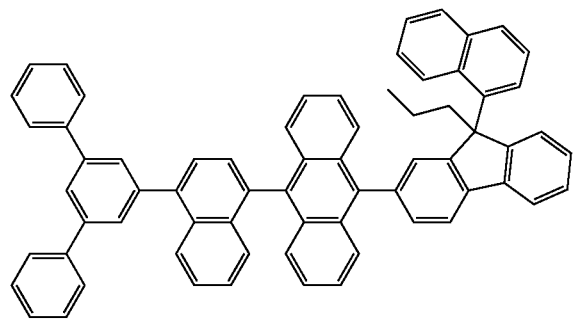
140
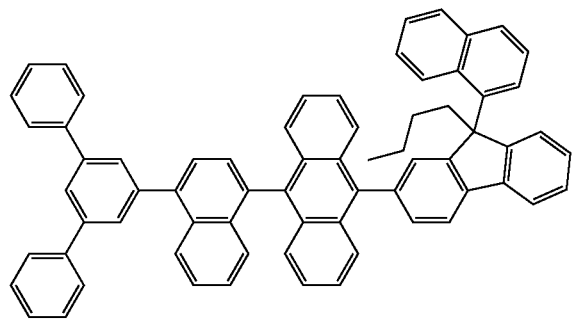

-continued
141
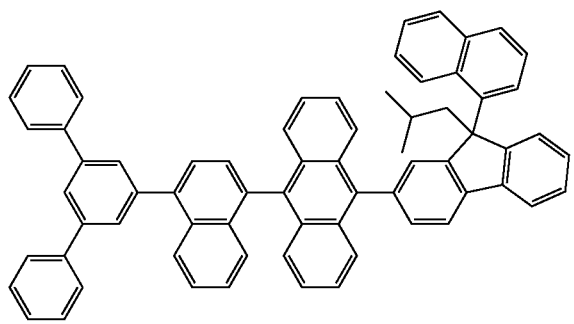
142
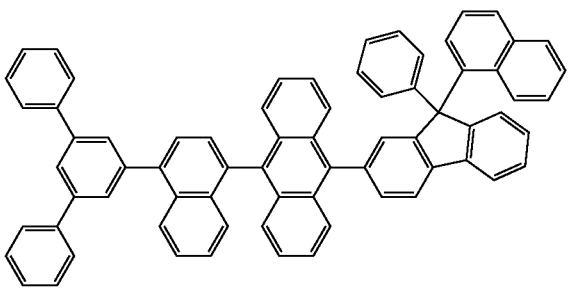
143
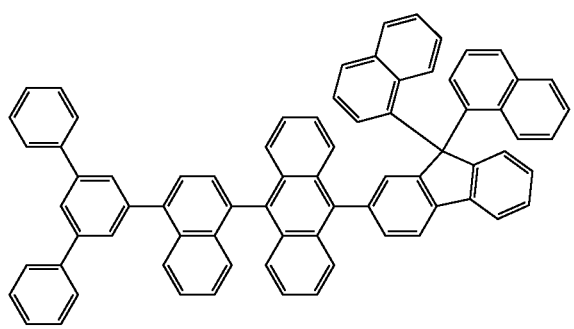
144
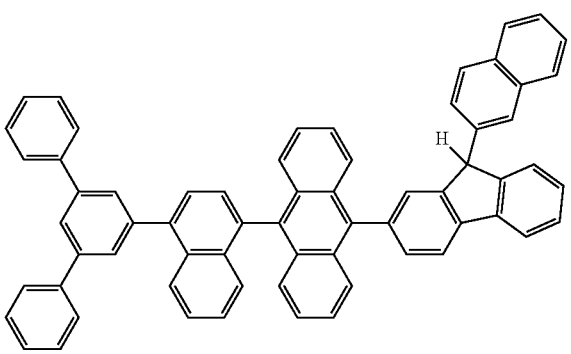
145
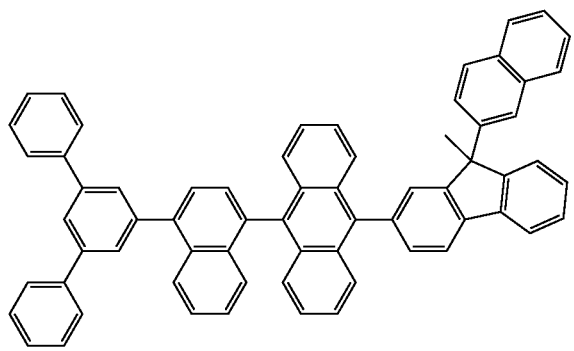
146
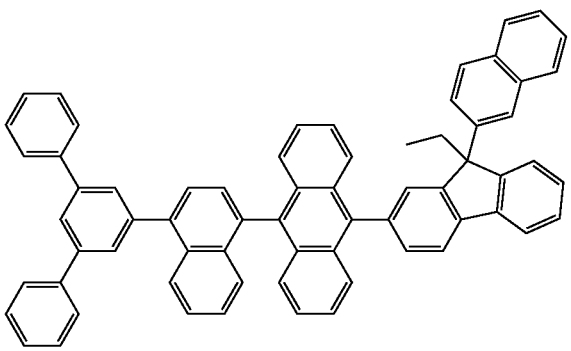
147
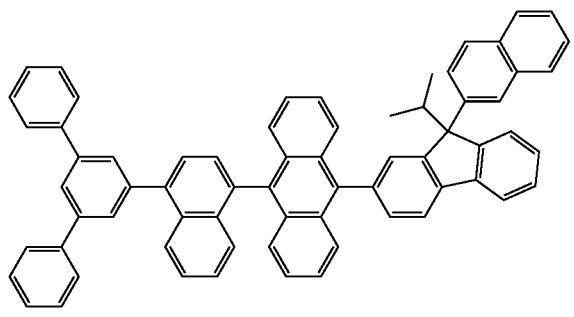
148
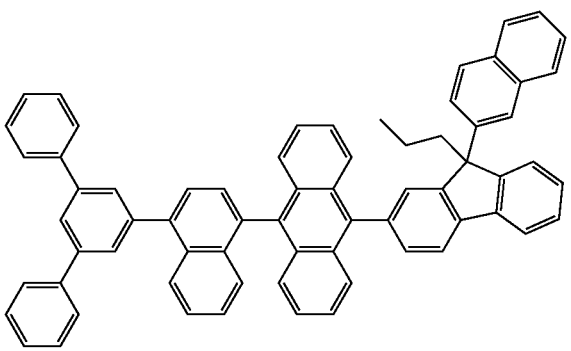

-continued
149
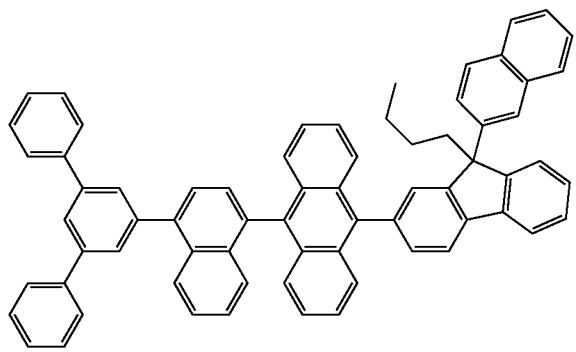
150
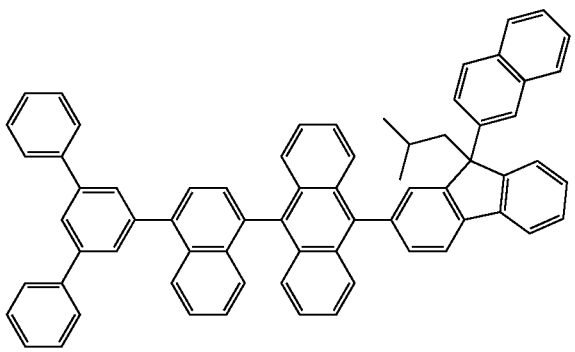
151
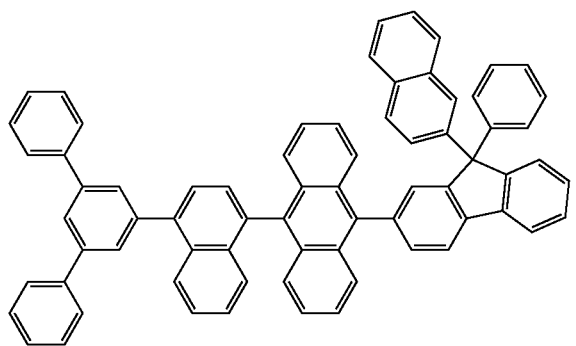
152
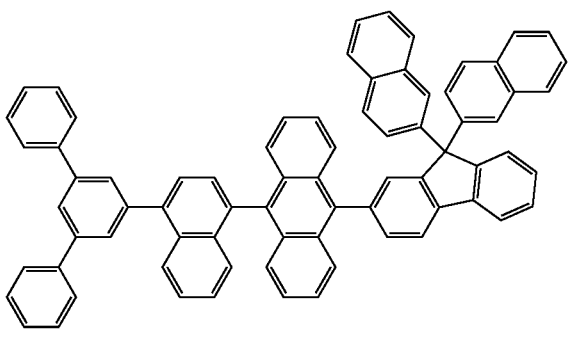
153
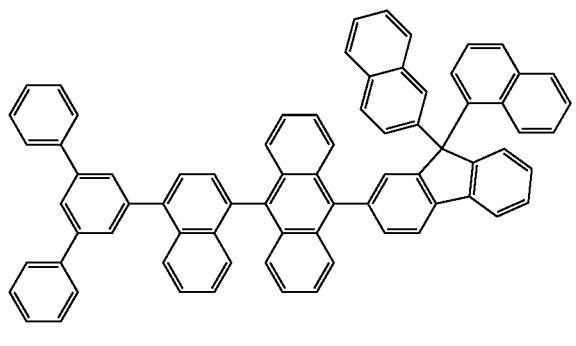
154
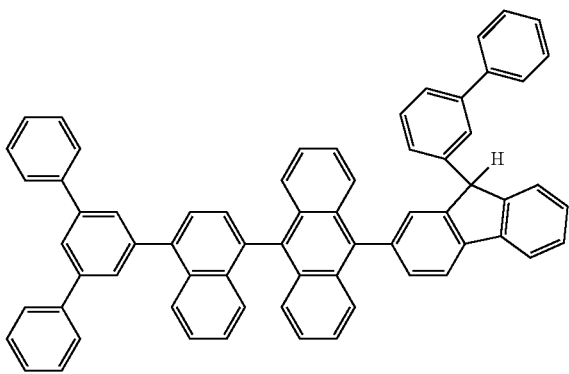
155
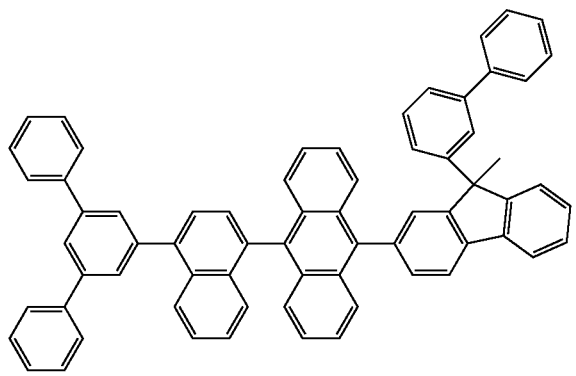
156
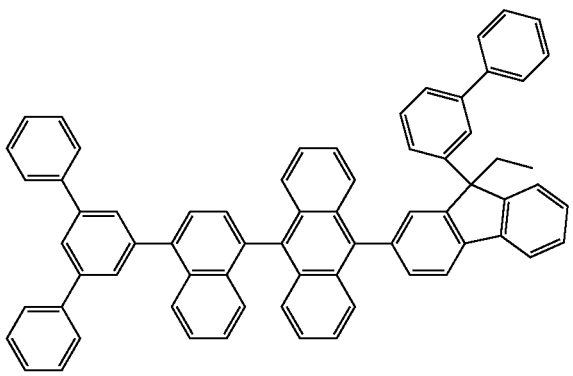

-continued
157
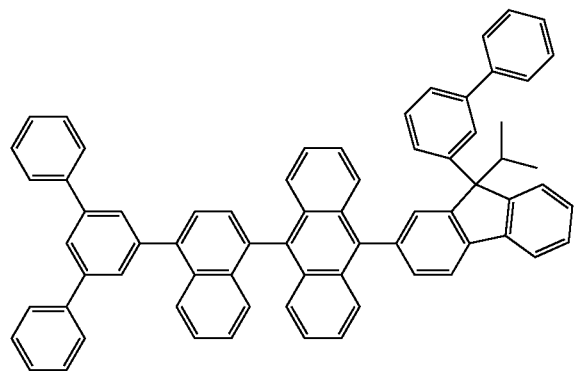
158
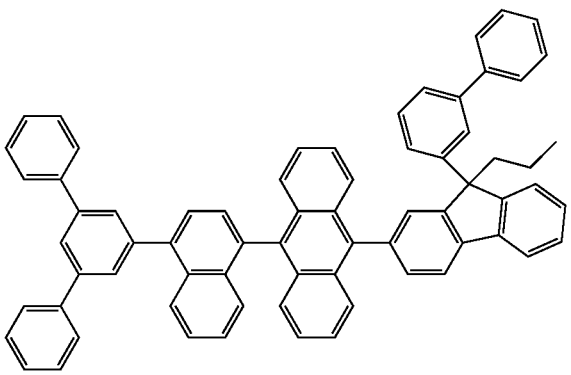
159
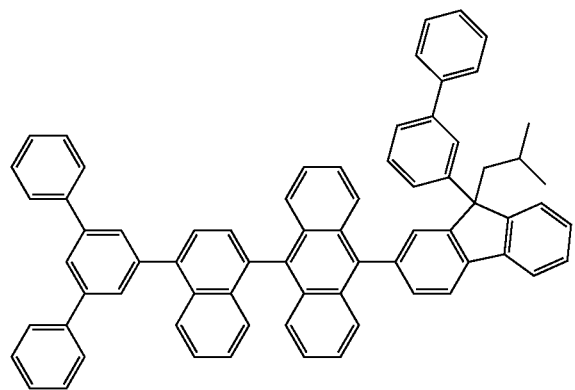
160
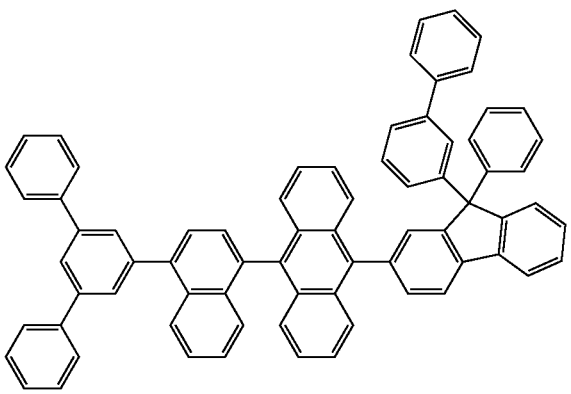
161
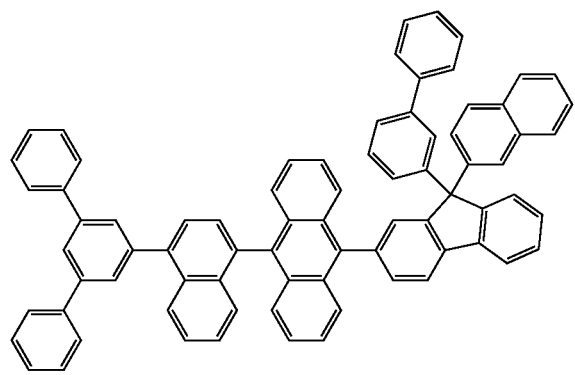
162
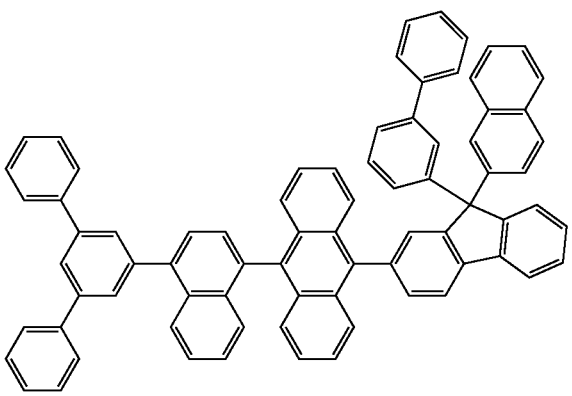
163
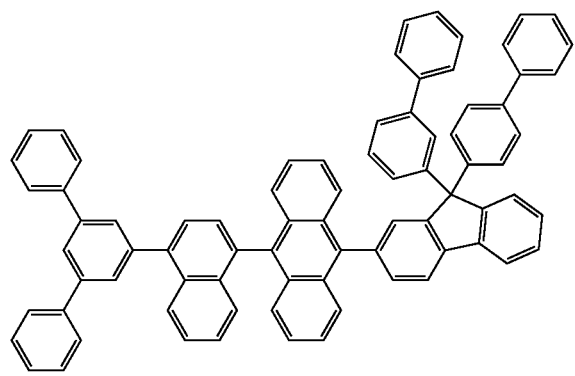
164
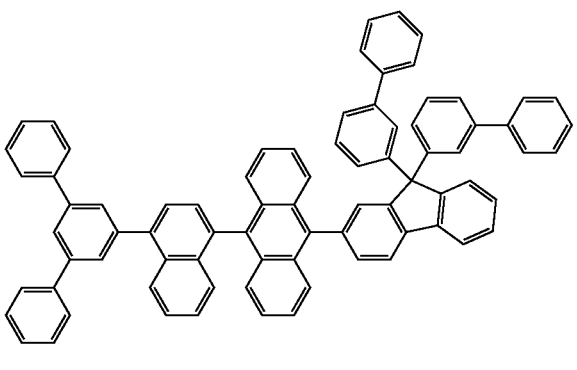

165
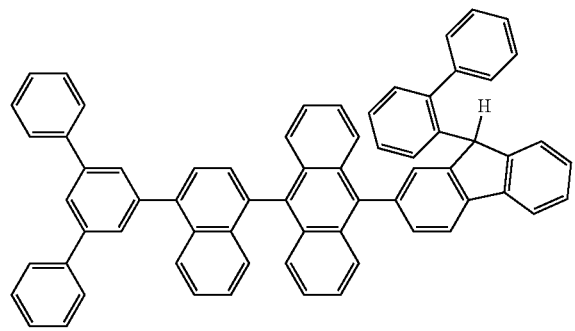
166
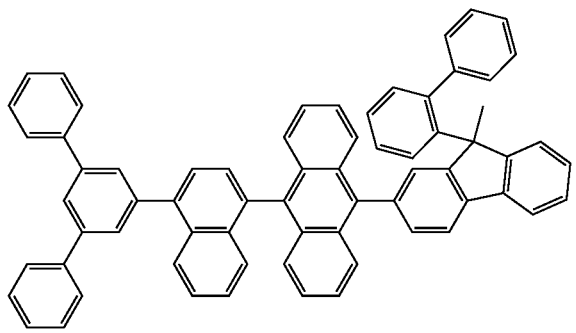
167
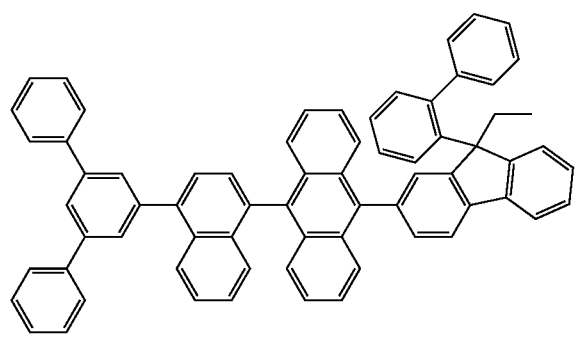
168
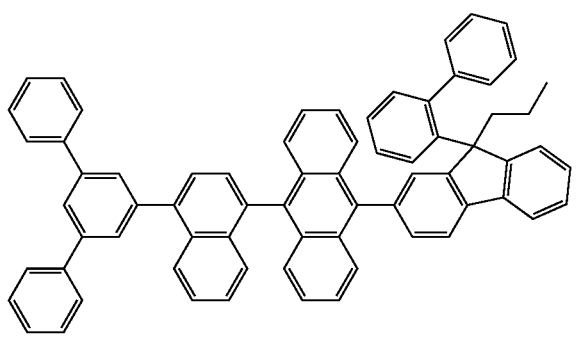
169
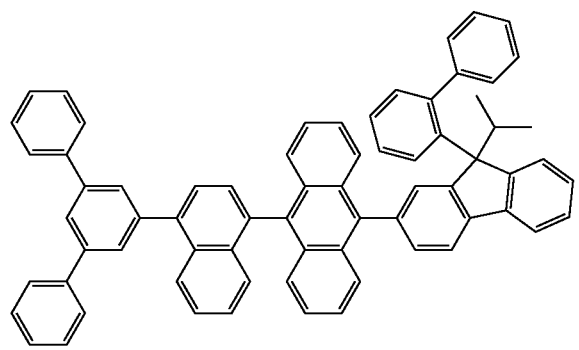
170
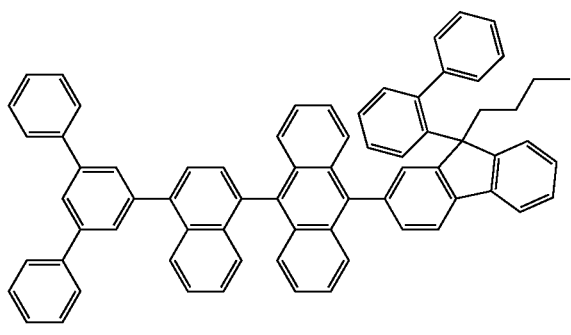
171
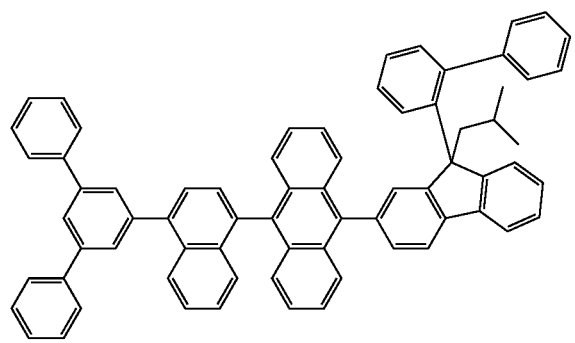
172
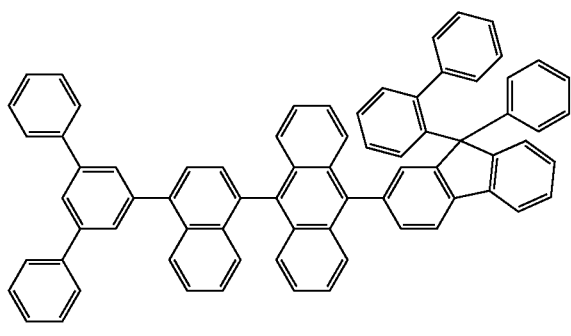

-continued
173
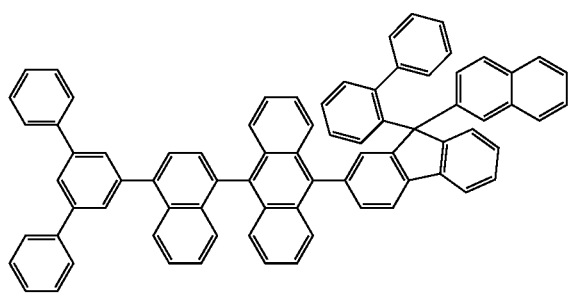
174
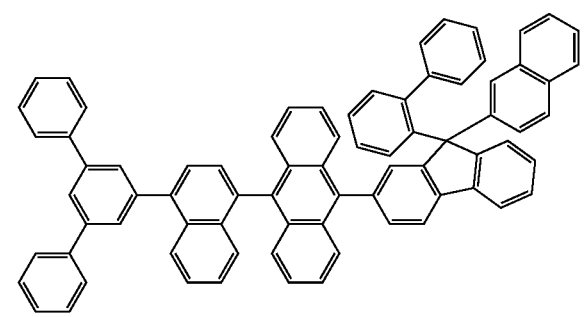
175
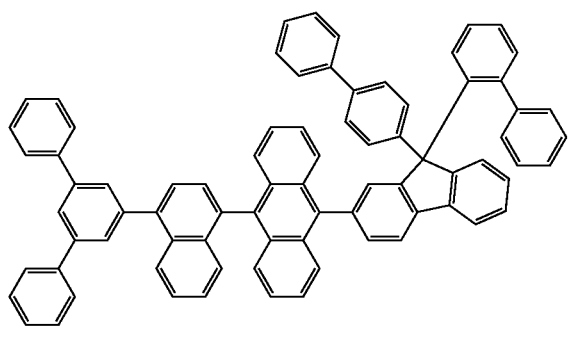
176
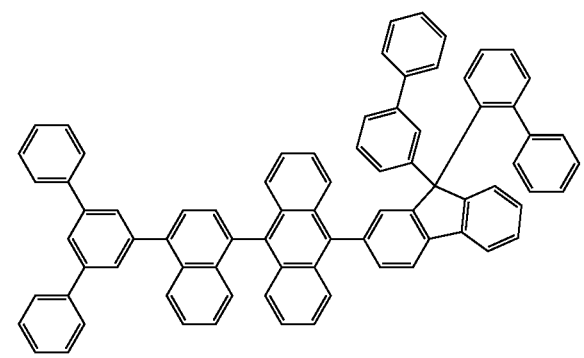
177
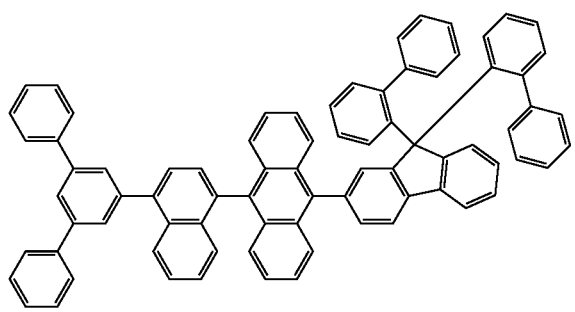
178
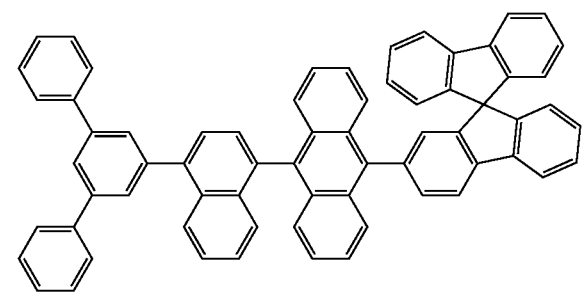
179
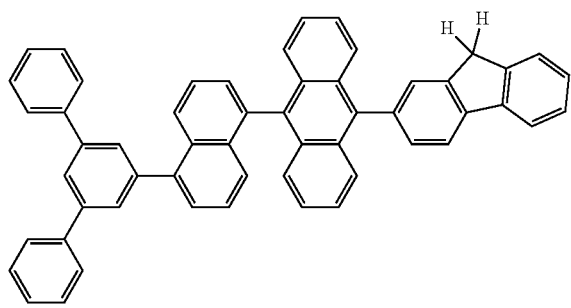
180
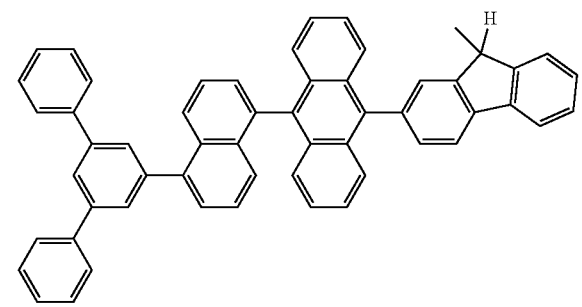

-continued
181
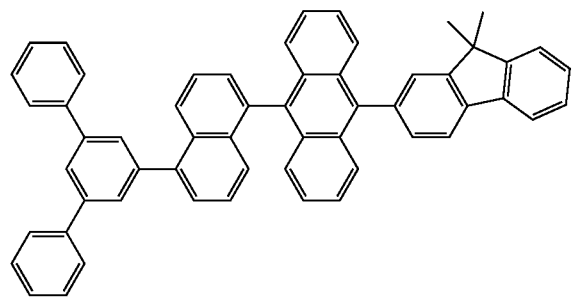
182
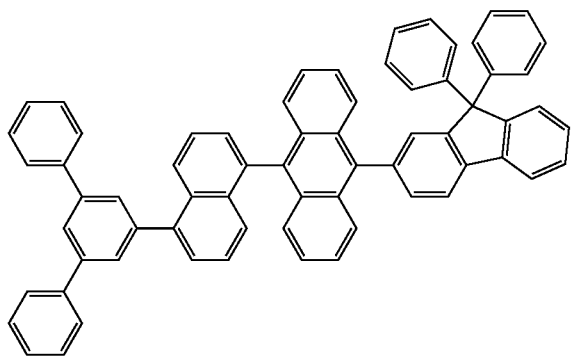
183
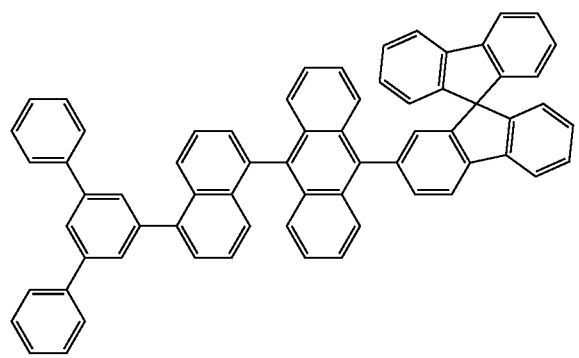
184
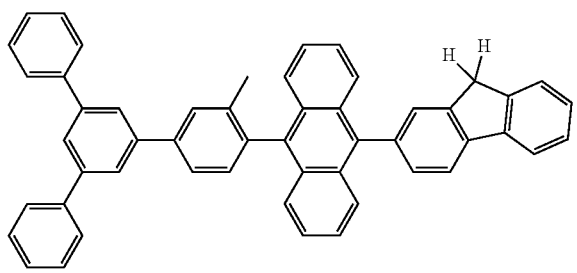
185
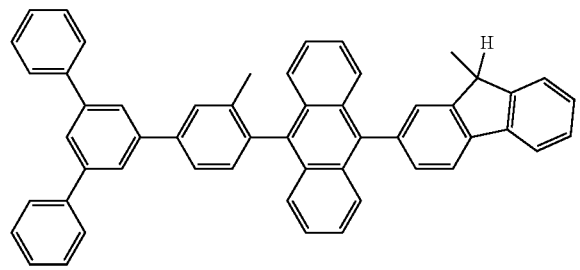
186
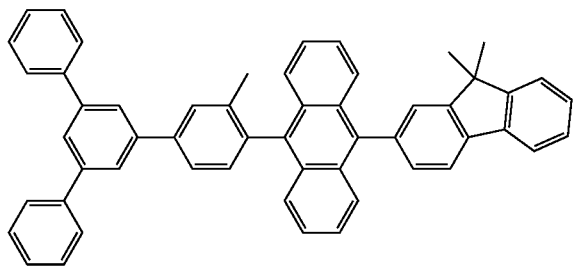
187
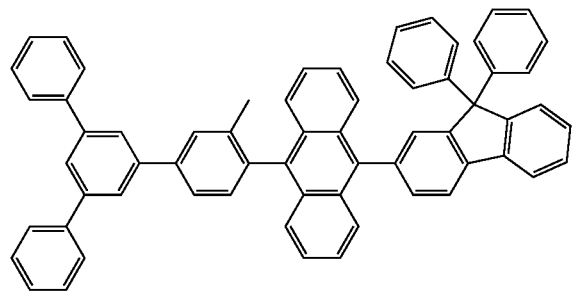
188
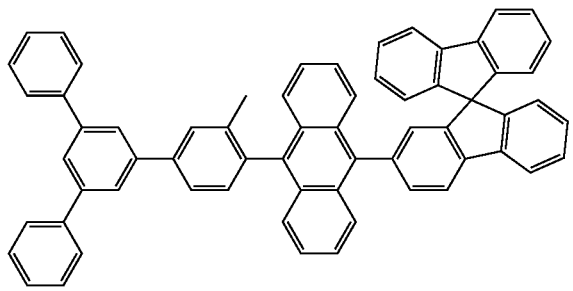
189
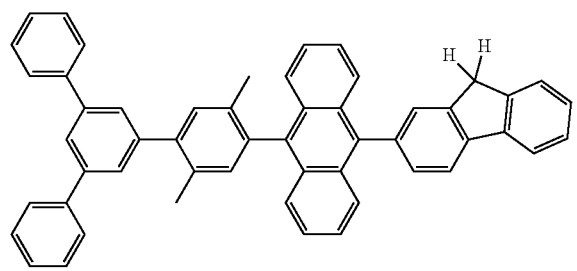
190
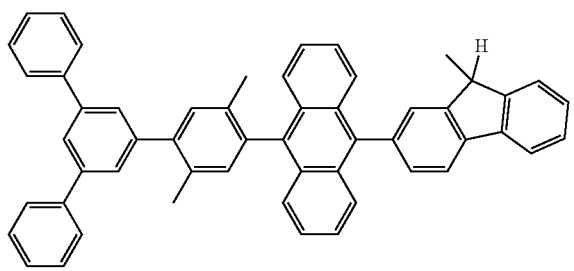

-continued
191
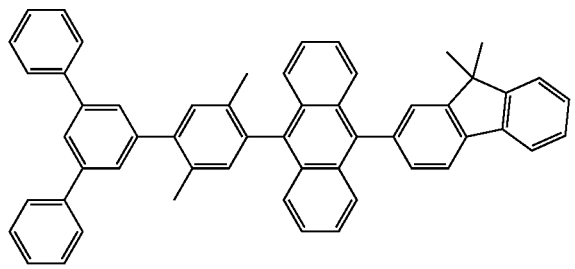
192
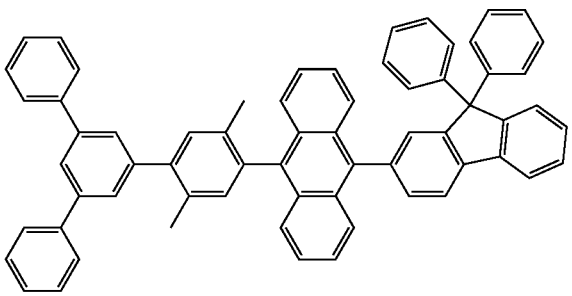
193
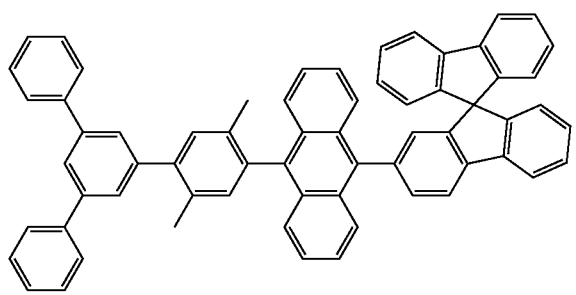
194
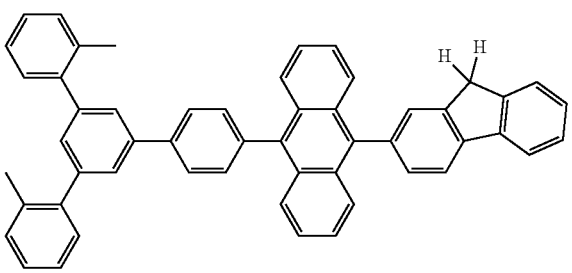
195
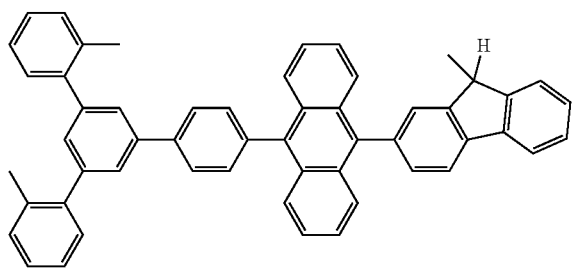
196
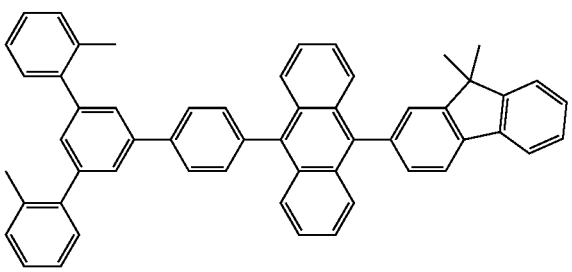
197
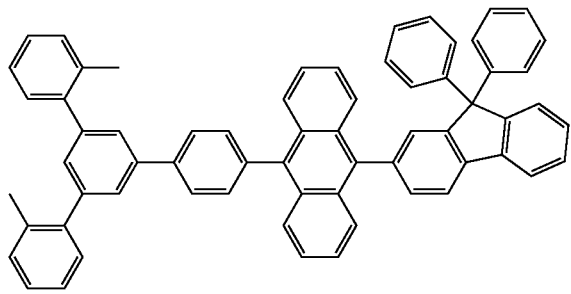
198
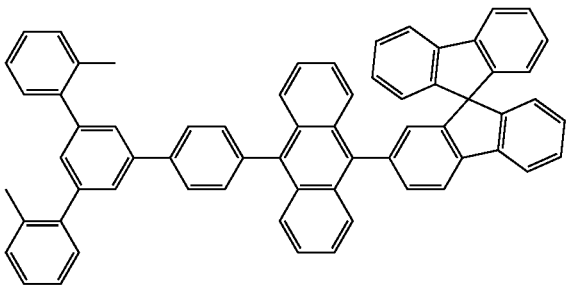
199
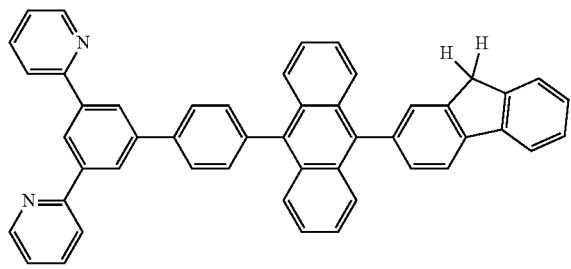
200
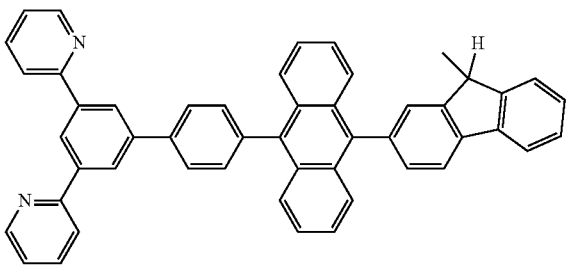

-continued
201
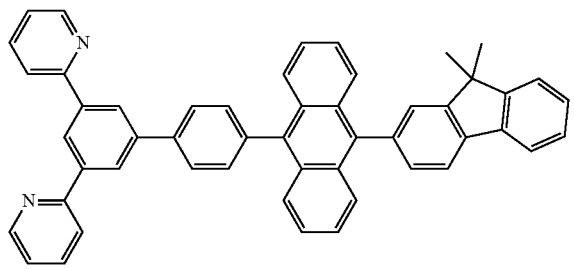
202
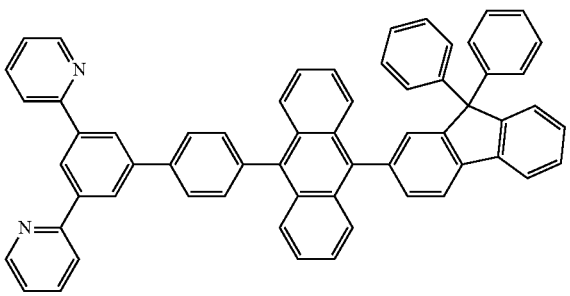
203
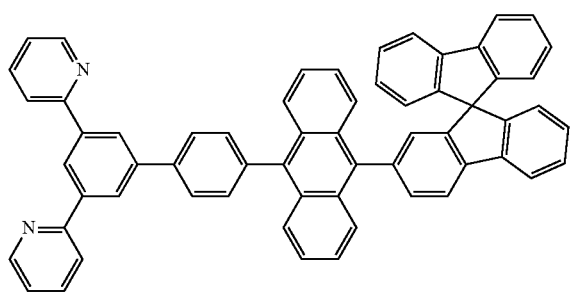
204
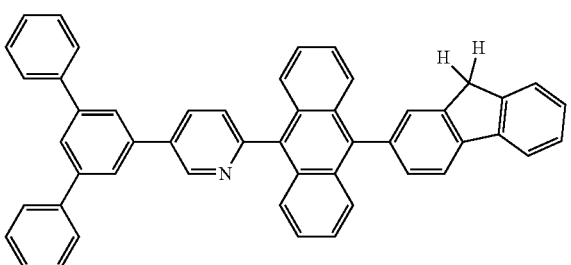
205
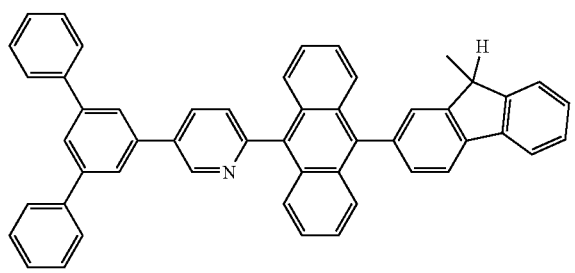
206
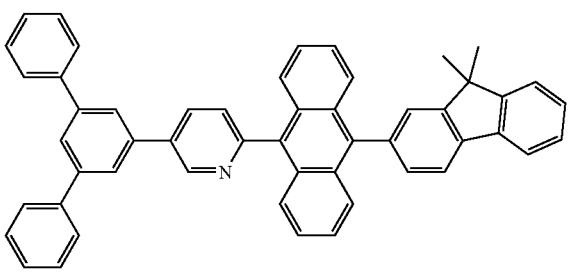
207
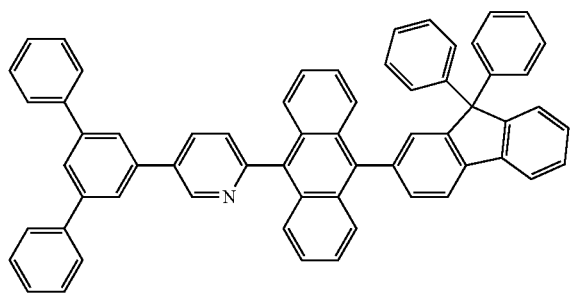
208
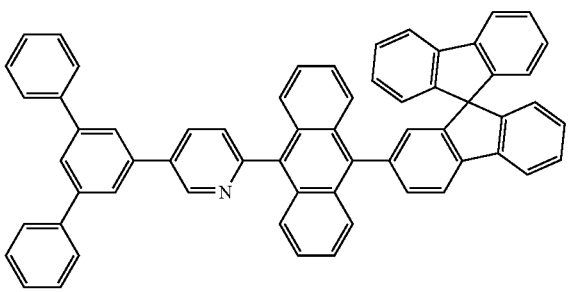
209
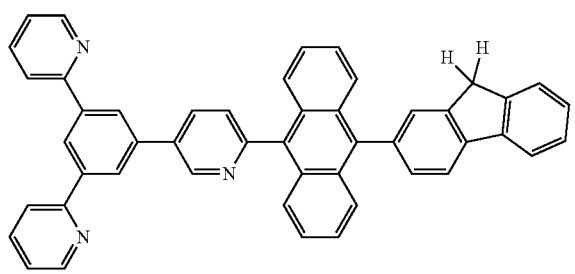
210
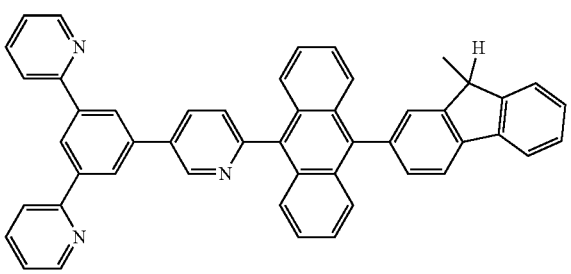

-continued
211
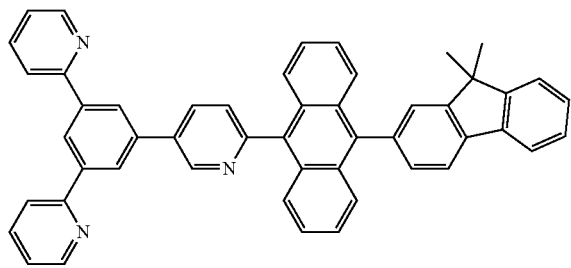
212
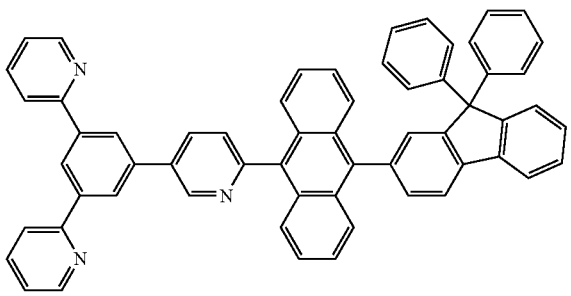
213
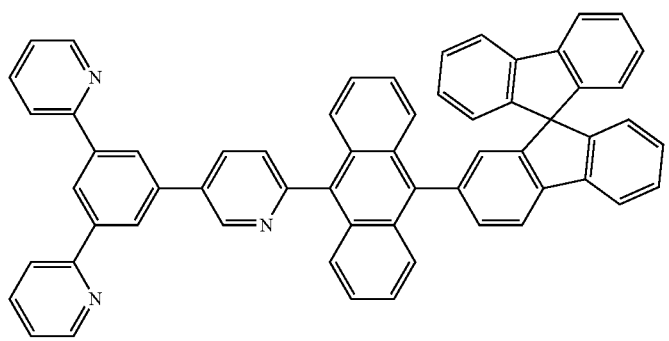
214
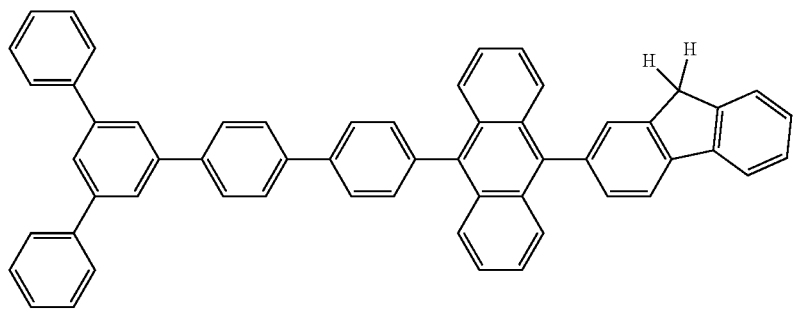
215
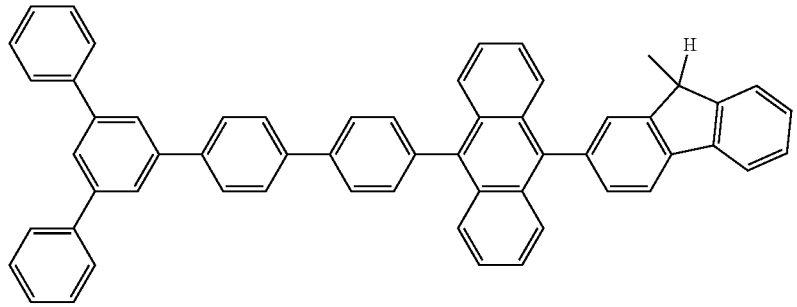
216
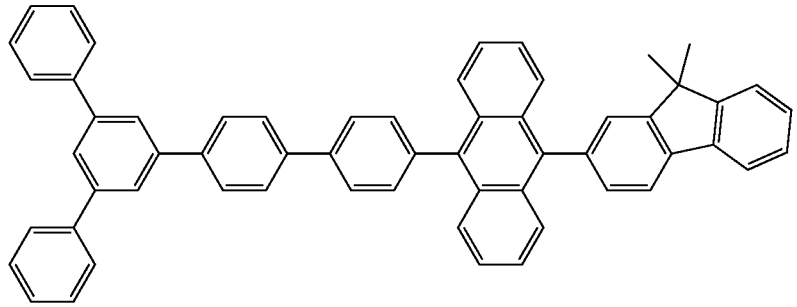

217
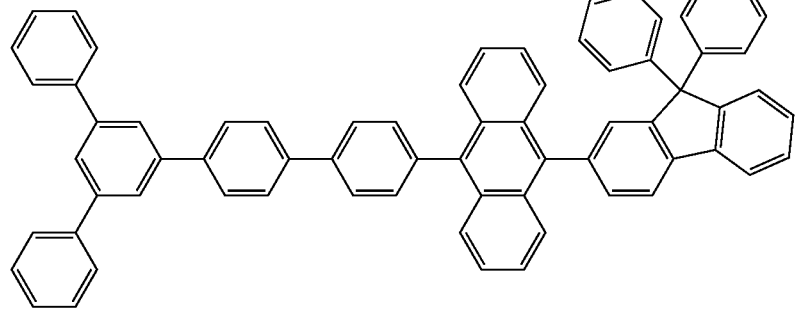
218
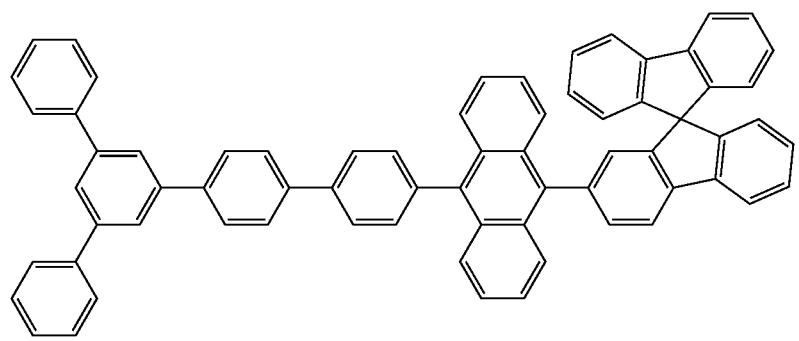
219 220 221 222
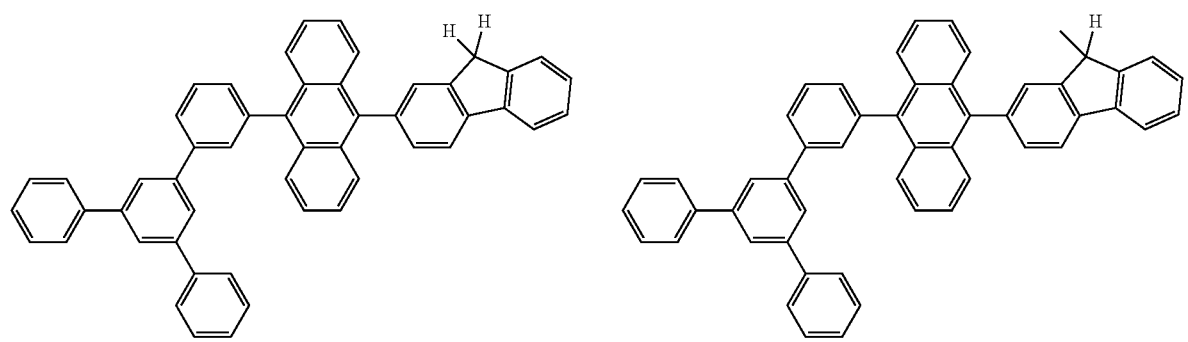
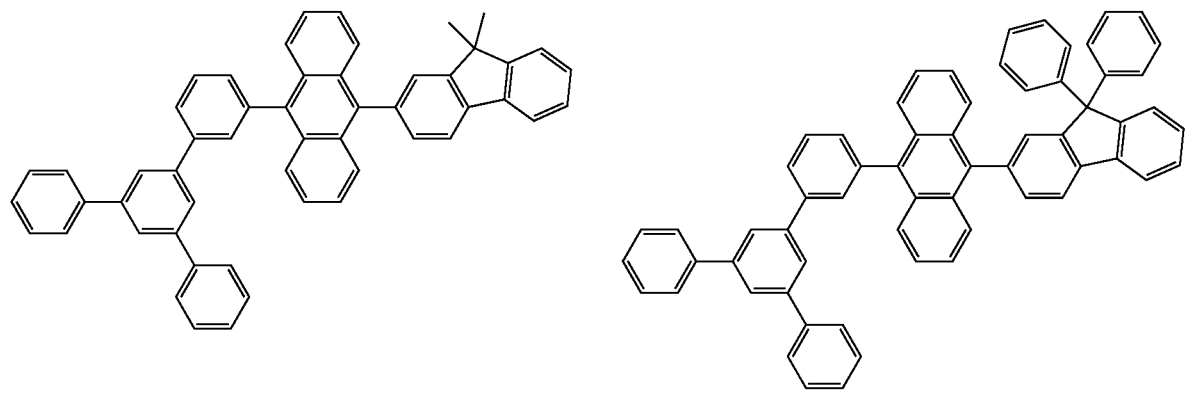

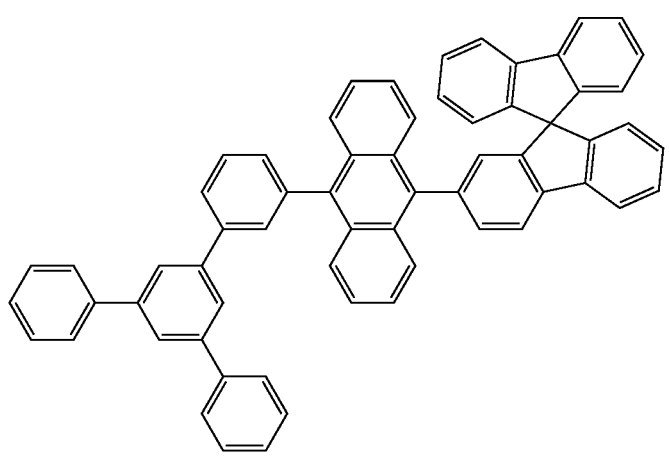

223

The materials of the hole transport layer and hole injection layer in the present invention should have good hole transport performance, which can effectively transport the holes from the anode to the organic light emitting layer. The materials used can include small molecule and polymer organic materials, including but not limited to tri-aromatic amine compounds, benzidine compounds, thiazole compounds, oxazole compounds, imidazole compounds, fluorene compound, phthalocyanine compounds, hexanitrile hexaazatriphenylene, 2,3,5,6-tetrafluoro-7, 7', 8,8'-tetracyanoanthraquinodimethane dimethyl-p-benzoquinone (F4-TCNQ), polyvinyl carbazole, polythiophene, polyethylene, polyethylene sulfonic acid.

The organic light emitting layer in the present invention contains, in addition to the compounds with the structural formula (I), the following but not limited to the following compounds: naphthalene compounds, pyrene compounds, fluorene compounds, phenanthrene compounds, chrysene compounds, fluoranthene compounds, anthracene compounds, dibenzanthracene compounds, perylene compound, bi-aryl vinyl compounds, triphenylamine vinyl compounds, amine compounds, benzimidazole compounds, furan compounds and organic metal chelate compounds.

The organic electron transport material of the organic electronic devices in the present invention should have good electron-transport performance, which can efficiently transfer electrons from the cathode to the light emitting layer. These materials can select the following compounds, but not limited to oxa oxazole, thiazoles, triazole compounds, tri-diazoxide compounds, tri-aza benzene compounds, quinoxaline compounds, dinitrogen anthracene compounds, silicon-containing heterocyclic compounds, quinoline compounds, phenanthroline compounds, metal chelates, fluoro-substituted benzene compounds.

One electron injection layer can be added to the organic electronic device of the present invention as required. The electron injection layer may effectively inject the electrons from the cathode into the organic layer, mainly selected from alkali metals or alkali metal compounds, or selected from alkaline earth metals or alkaline earth metal compounds, including but not limited to the following: lithium, lithium fluoride, lithium oxide, lithium nitride, 8-hydroxyquinoline lithium, cesium, cesium carbonate, 8-hydroxyquinoline cesium, calcium, calcium fluoride, calcium oxide, magnesium, magnesium fluoride, magnesium carbonate, magnesium oxide.

Experimental results show that, the OLEDs in the invention will have advantages of good light-emitting efficiency, excellent color purity and long lifetime.

BRIEF DESCRIPTION OF THE DRAWINGS

FIG. 5 is the TGA map of compound 89.

FIG. 6 shows the voltage-current density curves of Embodiments 4 and 5 and Comparative Example 1.

DETAILED DESCRIPTIONS OF THE PREFERRED EMBODIMENTS

Figure 1:
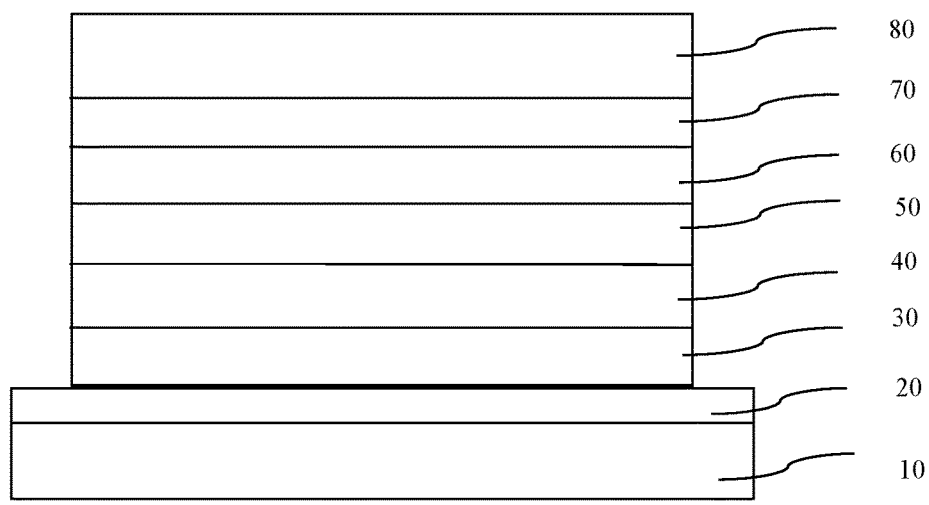
FIG. 1 is a structural charge of the device, of which, 10 denotes a glass substrate, 20 denotes an anode, 30 denotes hole injection layer, 40 denotes hole transport layer, 50 denotes light emitting layer, 60 denotes electron transport layer, 70 denotes electron injection layer, 80 denotes cathode.

In the following, the present invention is described in details by combining the following examples.

(The compounds 1a, 1b, 1e, 1h, 3a, 89a are common materials available in the markets)

Embodiment 1

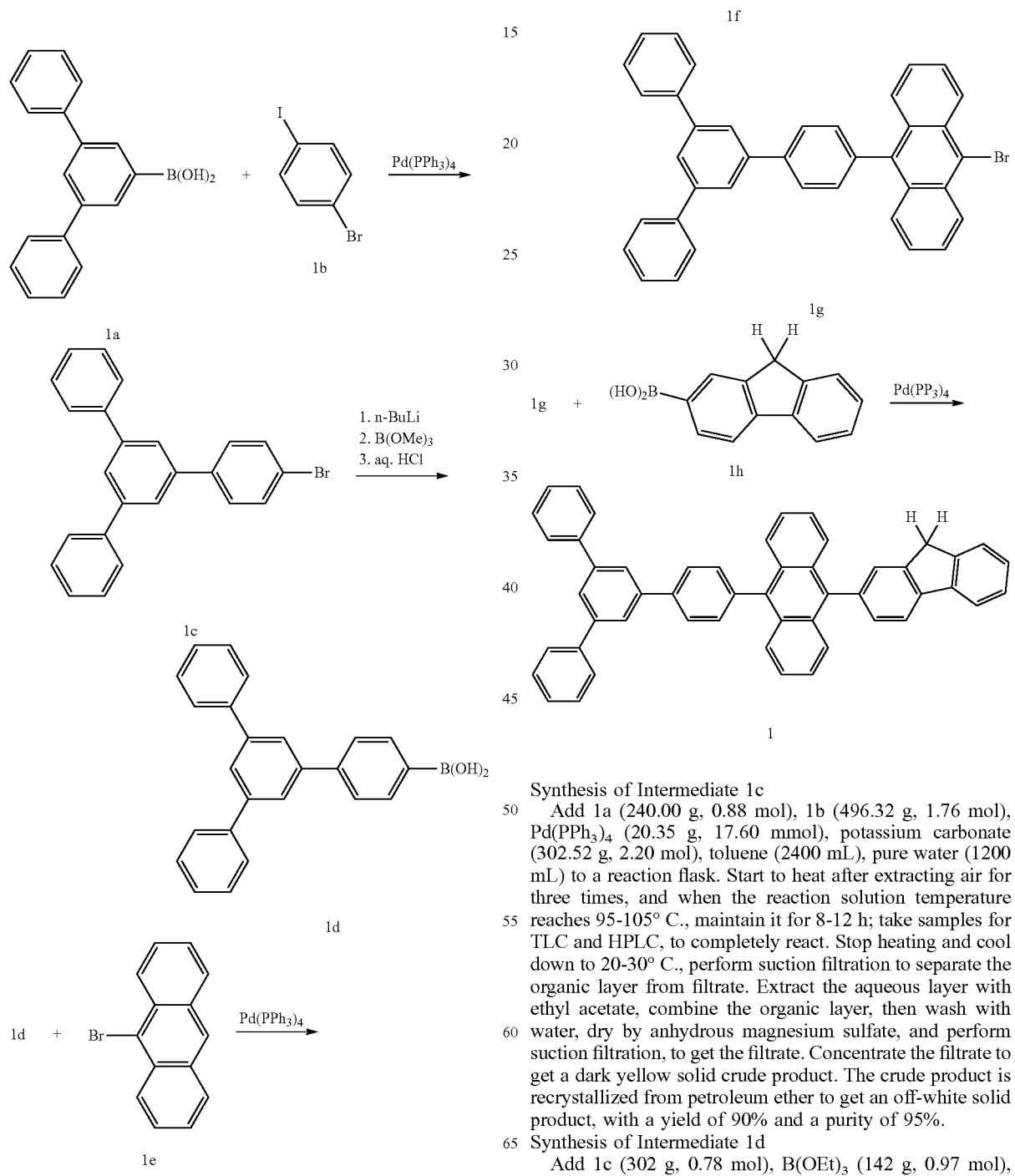

Synthesis of Intermediate 1c

Add 1a (240.00 g, 0.88 mol), 1b (496.32 g, 1.76 mol), Pd(PPh$_3$)$_4$ (20.35 g, 17.60 mmol), potassium carbonate (302.52 g, 2.20 mol), toluene (2400 mL), pure water (1200 mL) to a reaction flask. Start to heat after extracting air for three times, and when the reaction solution temperature reaches 95-105° C., maintain it for 8-12 h; take samples for TLC and HPLC, to completely react. Stop heating and cool down to 20-30° C., perform suction filtration to separate the organic layer from filtrate. Extract the aqueous layer with ethyl acetate, combine the organic layer, then wash with water, dry by anhydrous magnesium sulfate, and perform suction filtration, to get the filtrate. Concentrate the filtrate to get a dark yellow solid crude product. The crude product is recrystallized from petroleum ether to get an off-white solid product, with a yield of 90% and a purity of 95%.

Synthesis of Intermediate 1d

Add 1c (302 g, 0.78 mol), B(OEt)$_3$ (142 g, 0.97 mol), n-BuLi/THF (1.6 M, 600 mL), and anhydrous THF (3000 mL) at appropriate ratio to a reaction flask. After extracting with nitrogen for three times, cool down until the reaction solution temperature is −75~−65° C., slowly add n-BuLi/THF solution dropwise and control the temperature at −75~−65° C.; after dripping, continue to maintain this temperature for reaction 0.5-1 h. Then add appropriate amount of B(OEt)$_3$ dropwise, to control the reaction solution temperature at −75~−65° C., after dripping, continue to maintain this temperature for reaction 0.5-1 h. Then transfer the solution to room temperature for naturally heating reaction 4-6 h, then add 2M dilute hydrochloric acid to adjust the PH value to 2-3, after stirring about 1 h, stop the reaction. Add ethyl acetate to extract the solution, and the aqueous layer is extracted by EA. The organic layers are combined and dried over anhydrous magnesium sulfate, then suction filtration is conducted. The filtrate is concentrated to get an off-white solid product, with a purity of 95% and a yield of 62.5%.

Synthesis of Intermediate 1f

Add 1d (150 g, 0.43 mol), 1e (500 g, 0.86 mol), Pd(PPh$_3$)$_4$ (5.0 g, 0.44 mmol), potassium carbonate (130 g, 0.92 mol), toluene (1000 mL), pure water (500 mL) to a reaction flask. Start to heat after extracting nitrogen for three times, and when the reaction solution temperature reaches 95-105° C. maintain it for 8-12 h; take samples for TLC and HPLC, to completely react. Stop heating and cool down to 20-30° C., perform suction filtration to separate the organic layer from filtrate. Extract the aqueous layer with ethyl acetate, combine the organic layers, dry by anhydrous magnesium sulfate, and perform suction filtration. The filtrate is concentrated to get dark yellow solid crude product, with a purity of 80% and a yield of 78.1%.

Synthesis of Intermediate 1g

Add 1f (210 g, 0.42 mol), NBS (135 g, 0.71 mol), DMF (5 L) to a reaction flask. Start to heat after extracting nitrogen for three times, and when the reaction solution temperature reaches 60-65° C., maintain it for 6-8 h; take samples for TLC and HPLC, to completely react. Stop heating and cool down to 20-30° C., then pour the reaction solution to ice-water to separate dark yellow solid, and then perform suction filtration to get yellow solid and bake to obtain 1 g of crude product. Add the crude product to DCM/MeOH until the solution becomes slightly turbid, continue to stir for about 30 min, to separate out a large amount of solid, then perform suction filtration to get pale yellow solid product, with a yield of approximate 54.05% and a purity of 98.5%.

$^1$H NMR (300 MHz, CDCl$_3$) δ 8.64 (d, J=8.8 Hz, 2H), 7.99-7.90 (m, 4H), 7.87 (t, J=1.6 Hz, 1H), 7.78 (dd, J=9.3, 2.3 Hz, 6H), 7.61 (ddd, J=8.8, 6.5, 1.1 Hz, 2H), 7.56-7.48 (m, 6H), 7.46-7.38 (m, 4H).

$^{13}$C NMR (76 MHz, CDCl$_3$) δ 142.67 (s), 142.03 (s), 141.26 (s), 140.69 (s), 137.83 (s), 137.52 (s), 131.87 (s), 131.24 (s), 130.44 (s), 129.09 (s), 128.80 (s), 128.38-127.40 (m), 127.18 (s), 126.05-125.21 (m), 123.08 (s), 77.74 (s), 77.31 (s), 76.89 (s), 30.10 (s).

Synthesis of Compound 1

Add 1 g (9.5 g, 16.92 mmol), 1h (6.41 g, 30.51 mmol), Pd(PPh$_3$)$_4$ (1.5 g, 1.3 mmol), potassium carbonate (5.84 g, 42.3 mmol), toluene (150 mL) and pure water (75 mL) to a 500 ml three-necked flask. After extracting nitrogen for three times, reaction occurs at 105° C. The time of reaction stop is around 12 h, which is detected by liquid phase. The reaction solution is earth yellow of catalyst at the beginning, slowly turning into a yellow solution. After reaction stops, the upper layer is bright and light yellow, and the lower layer is water. After reaction stops, filter the solution, wash the filter residues with ethyl acetate until no product in the residue, then collect the filtrate, spin-dry, to separate out a large amount of off white solid. Collect the filter residue to dry, to get the target product, with purity of 98%; after vacuum sublimation, gray-white solid powder with purity of 99.5% is obtained.

$^1$H-NMR (300 MHz, CDCl$_3$) δ 8.10-8.21 (d, 2H), 7.96-7.98 (dd, 3H), 7.87-7.89 (m, 2H), 7.81-7.86 (m, 4H), 7.78-7.81 (d, 4H), 7.62-7.65 (m, 2H), 7.59 (s, 1H), 7.51-7.57 (m, 5H), 7.45-7.48 (m, 2H), 7.36-7.43 (m, 7H), 3.88 (s, 2H).

Embodiment 2

Synthesis of Compound 3

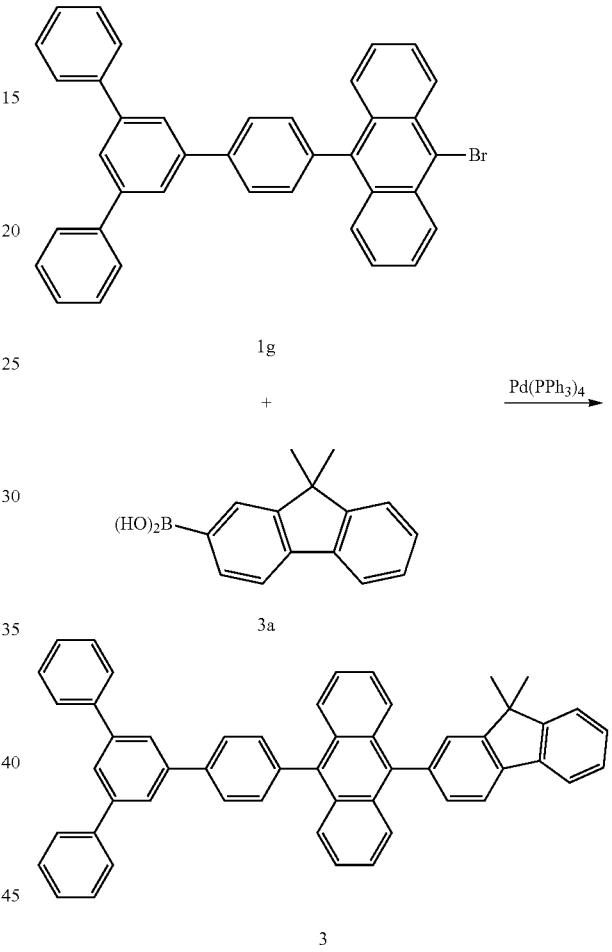

Add 1 g (9.5 g, 16.92 mmol), 3a (7.25 g, 30.46 mmol), Pd(PPh$_3$)$_4$ (1.5 g, 1.3 mmol), potassium carbonate (5.84 g, 42.3 mmol), toluene (150 mL) and pure water (75 mL) to a 500 ml three-necked flask. After extracting nitrogen for three times, reaction occurs at 105° C. The time of reaction stop is around 12 h, which is detected by liquid phase. The reaction solution is earth yellow of catalyst at the beginning, slowly turning into a yellow solution. After reaction stops, the upper layer is bright and light yellow, and the lower layer is water. After reaction stops, filter the solution, wash the filter residues with ethyl acetate until no product in the residue, then collect the filtrate, spin-dry, to separate out a large amount of off white solid. Collect the filter residue to dry, to get the target product, with purity of 98%; after vacuum sublimation, gray-white solid powder with purity of 99.7% is obtained.

$^1$H-NMR (300 MHz, CDCl$_3$) δ 8.1-8.2 (d, 2H), 7.96-7.99 (dd, 3H), 7.88-7.89 (m, 2H), 7.81-7.86 (m, 4H), 7.78-7.81 (d, 4H), 7.61-7.65 (m, 2H), 7.59 (s, 1H), 7.51-7.56 (m, 5H), 7.46-7.48 (m, 2H), 7.35-7.43 (m, 7H), 1.61 (s, 6H).

Embodiment 3

Synthesis of Compound 89

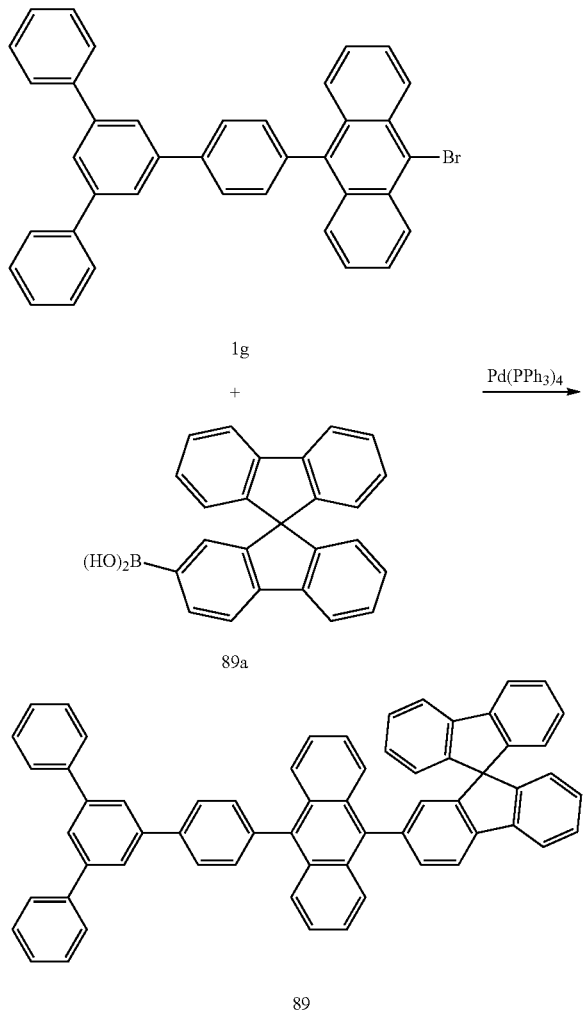

Add 1 g (10.0 g, 17.8 mmol), 89a (7.1 g, 19.6 mmol), Pd(PPh$_3$)$_4$ (432.2 mg, 0.35 mmol), K2CO3 (6.14 g, 44.5 mmol), toluene (300 mL) and water (150 mL) successively to a reaction tank. After deoxygenization of the device and introduction of nitrogen, heat to 100° C. for reaction overnight, apply to the plates at a ratio of DCM:PE=1:5. The product gives out intensive blue light under UV light at 365 nm wavelength, with the Rf value at about 0.2. Perform suction filtration with the reaction solution, wash the filter cake with ethyl acetate (100 mL) twice and separate. Extract the aqueous layer with ethyl acetate (100 mL) once, combine the organic layers, then wash the organic layer once with water (200 mL). spin dry to remove the solvent. The crude product is recrystallized from 120 ml DCM/MeOH, then suction filtration is performed to get 13.1 g yellow solid powder, with a purity of 98.7% and a yield of 92.2% yield. After vacuum sublimation, a slight yellow solid powder with purity of 99.7% is obtained. m/z=797.

Figure 2:
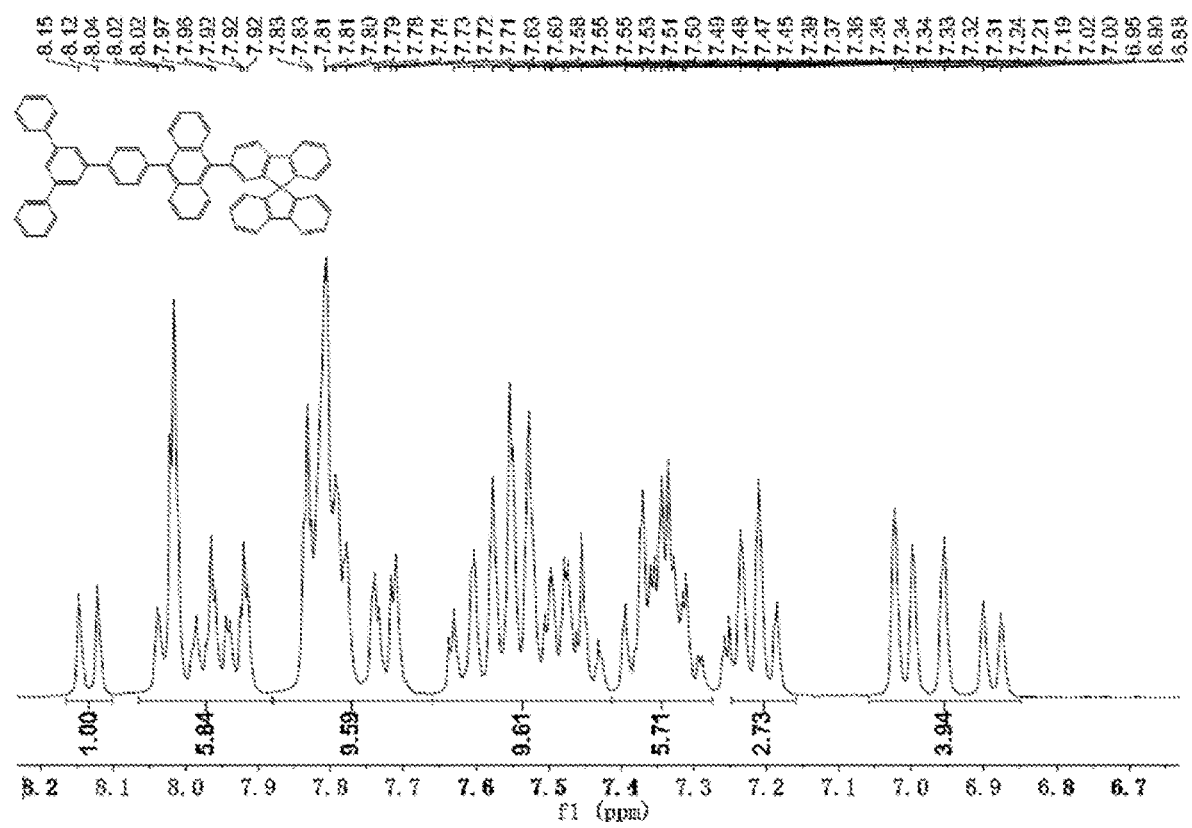
FIG. 2 is the $^1$H NMR diagram of compound 89.
Figure 3:
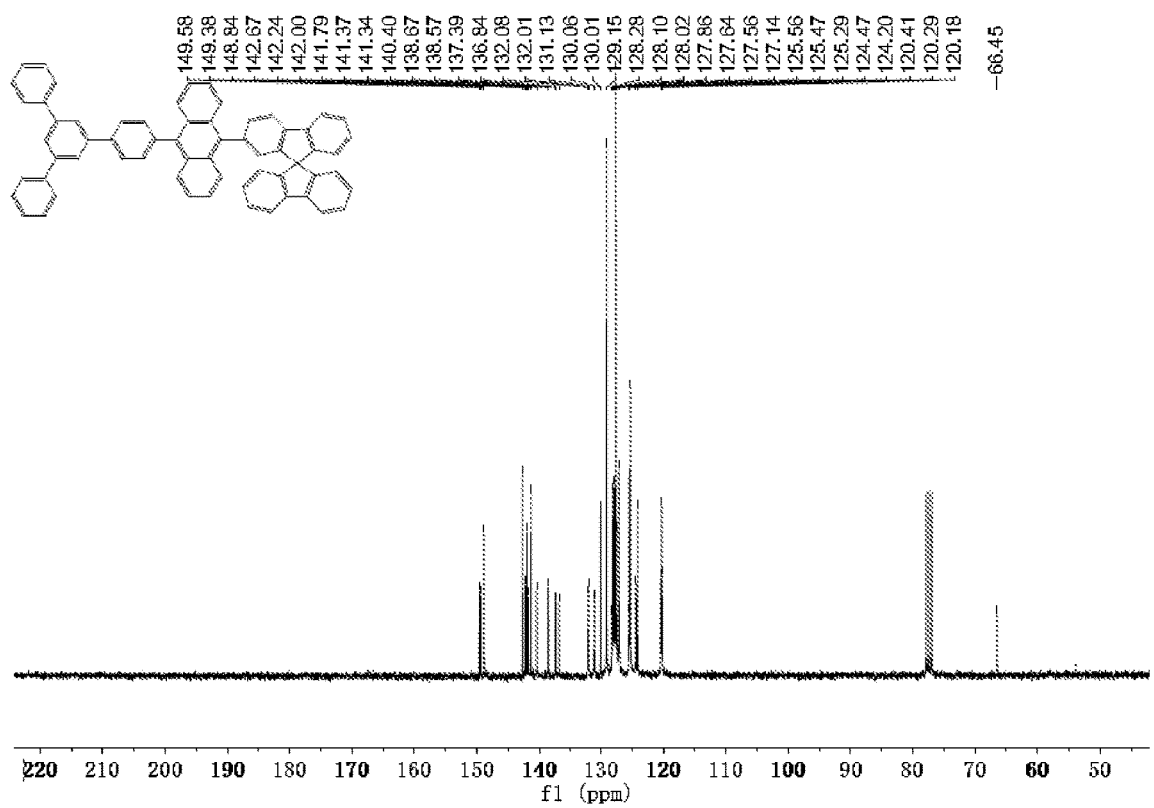
FIG. 3 is the $^{13}$C NMR diagram of compound 89.
Figure 4:
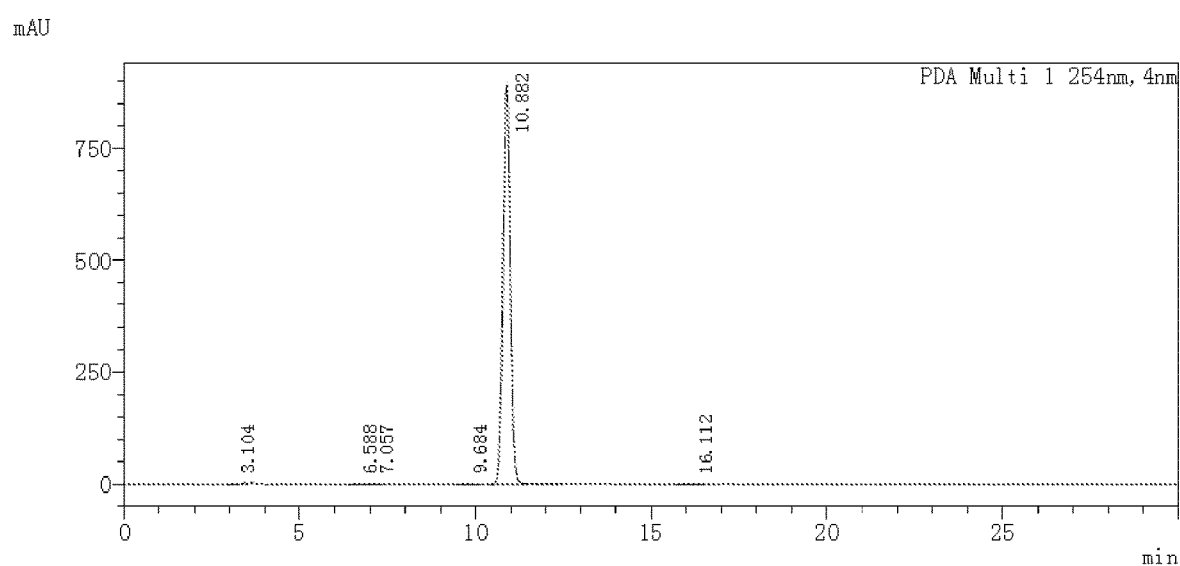
FIG. 4 is a high performance liquid chromatogram of compound 89.
Figure 7:
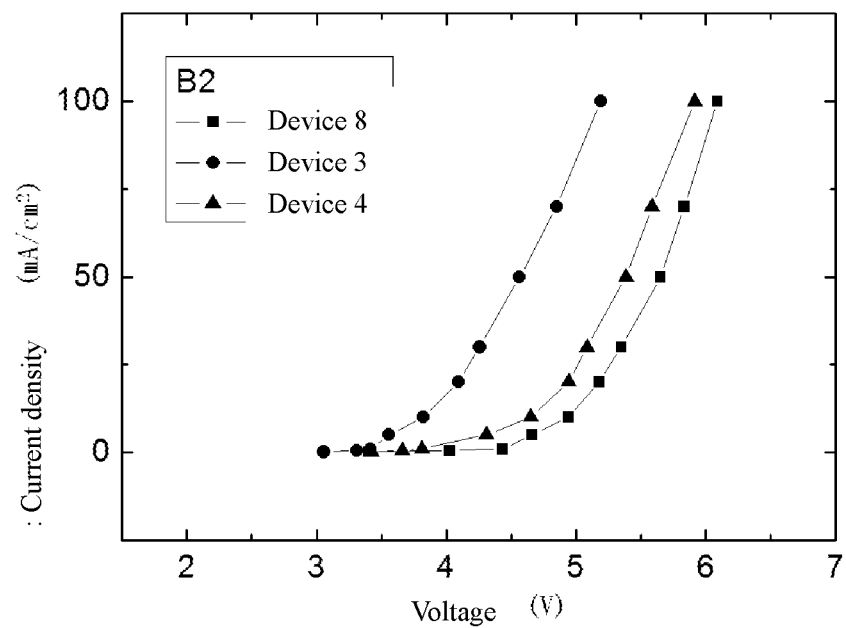
FIG. 7 shows the voltage-current density curves of Embodiments 6 and 7 and Comparative Example 2.
Figure 8:
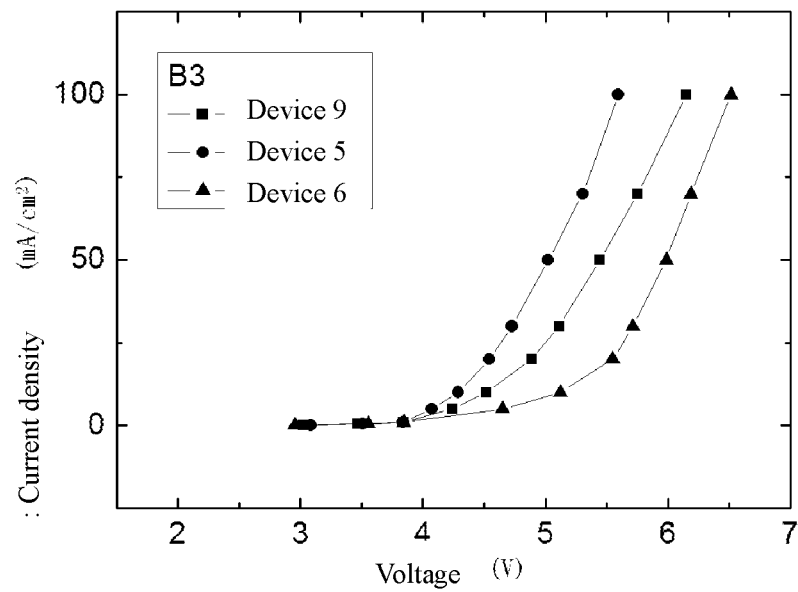
FIG. 8 shows the voltage-current density curves of Embodiments 8 and 9 and Comparative Example 3.
Figure 9:
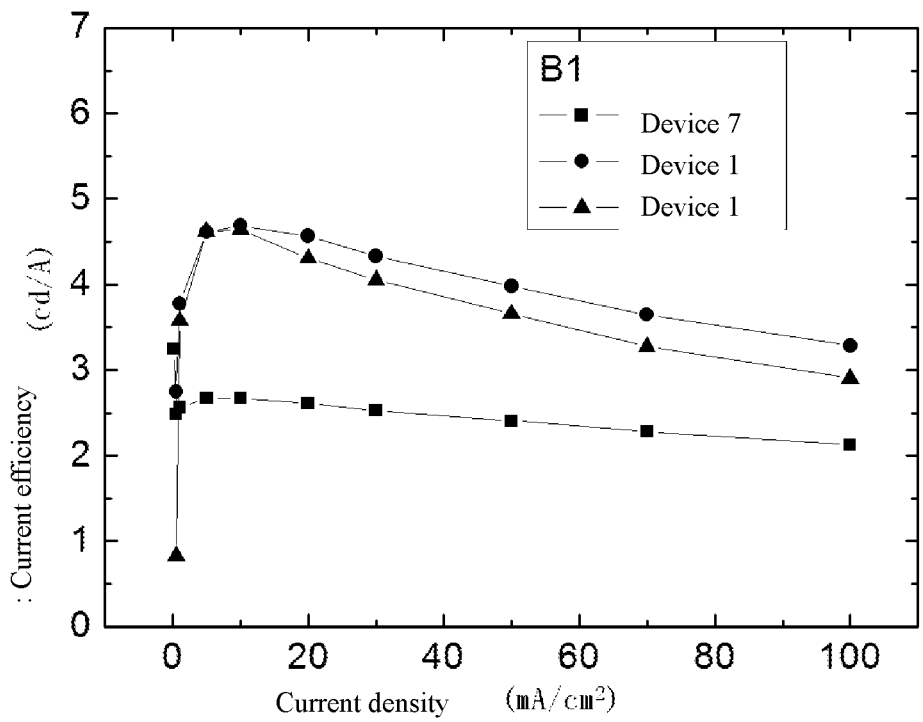
FIG. 9 shows the current density-current efficiency curves of Embodiments 4 and 5 and Comparative Example 1.
Figure 10:
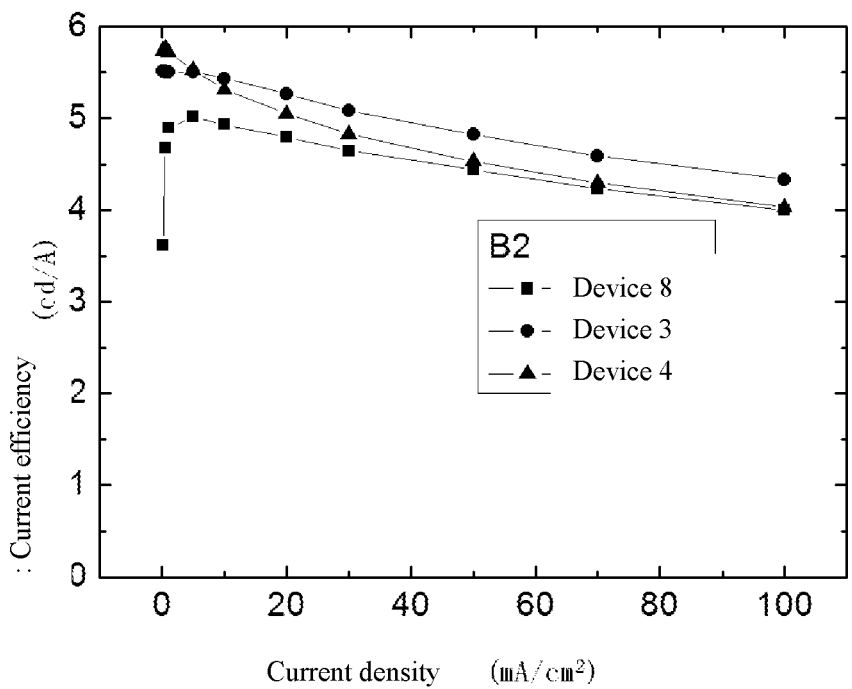
FIG. 10 shows the current density-current efficiency curves of Embodiments 6 and 7 and Comparative Example 2.
Figure 11:
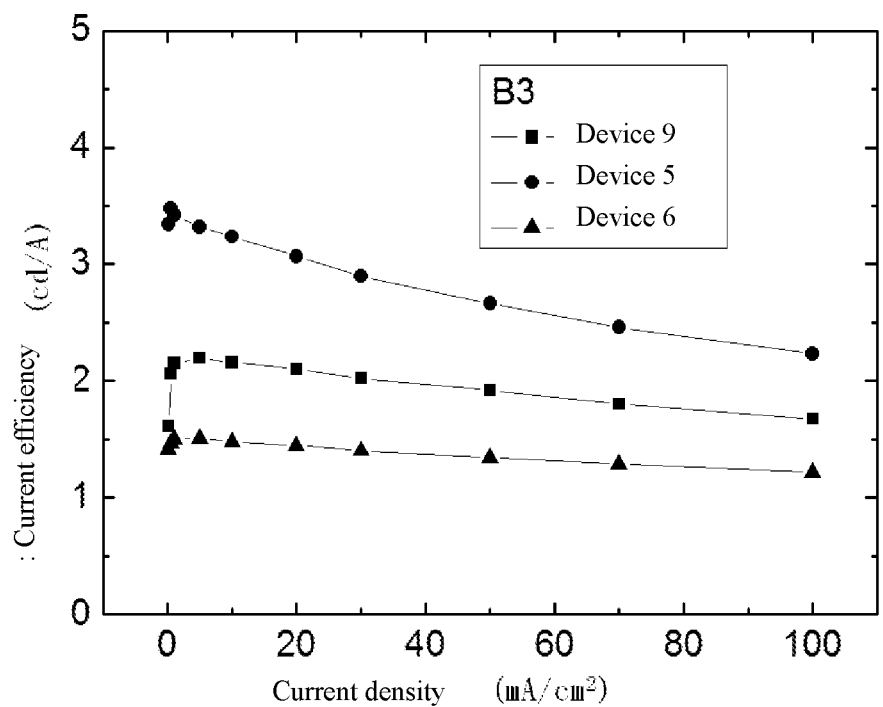
FIG. 11 shows the current density-current efficiency curves of Embodiments 8 and 9 and Comparative Example 3.
Figure 12:
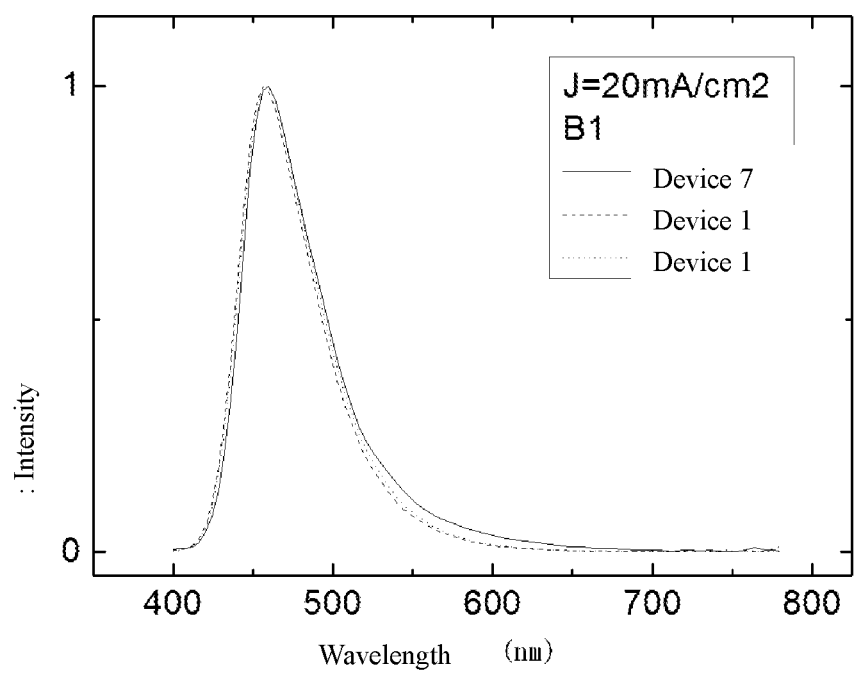
FIG. 12 shows the light-emitting spectra of Embodiments 4 and 5 and Comparative Example 1.
Figure 13:
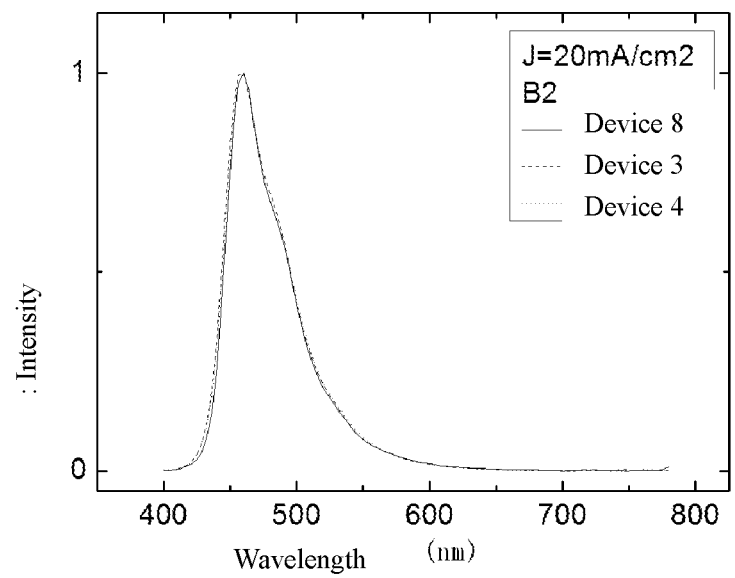
FIG. 13 shows the light-emitting spectra of Embodiments 6 and 7 and Comparative Example 2.
Figure 14:
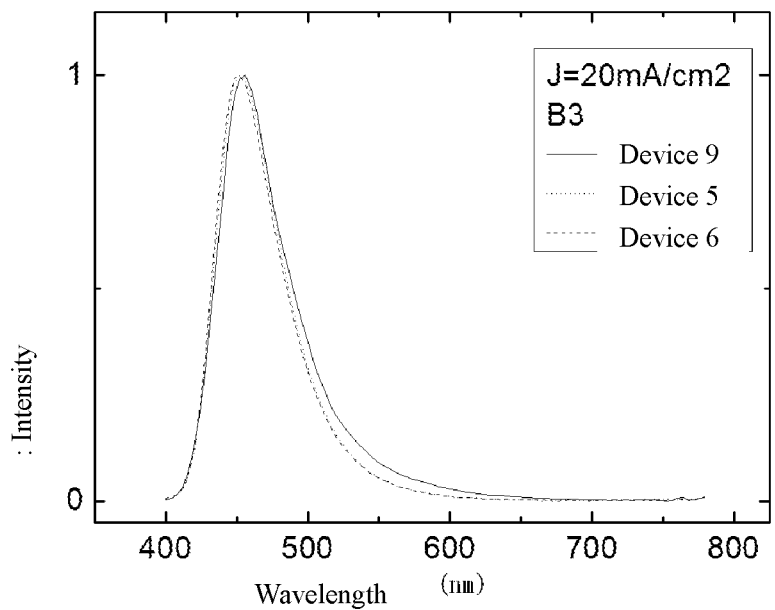
FIG. 14 shows the light-emitting spectra of Embodiments 8 and 9 and Comparative Example 3.
Figure 15:
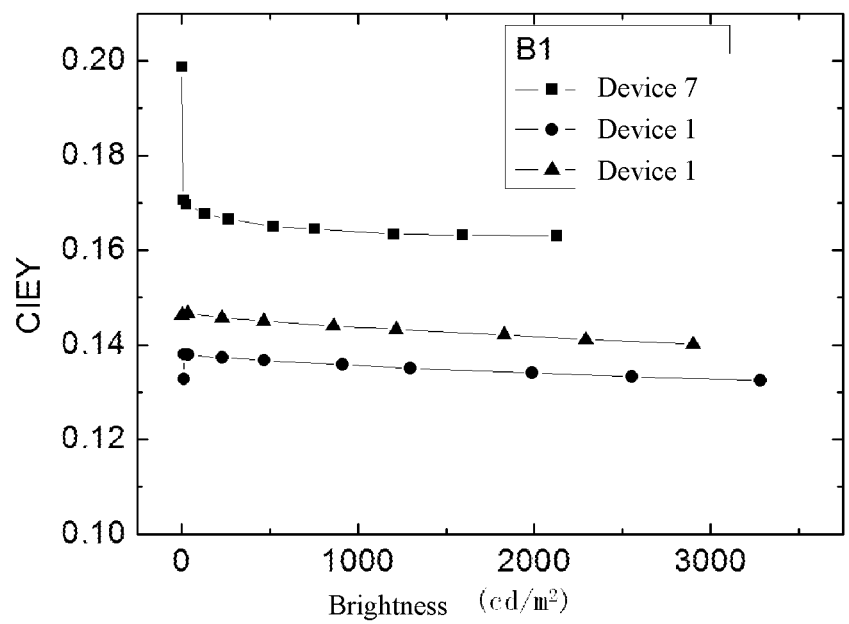
FIG. 15 shows the brightness-CIEy plot of Embodiments 4 and 5 and Comparative Example 1.
Figure 16:
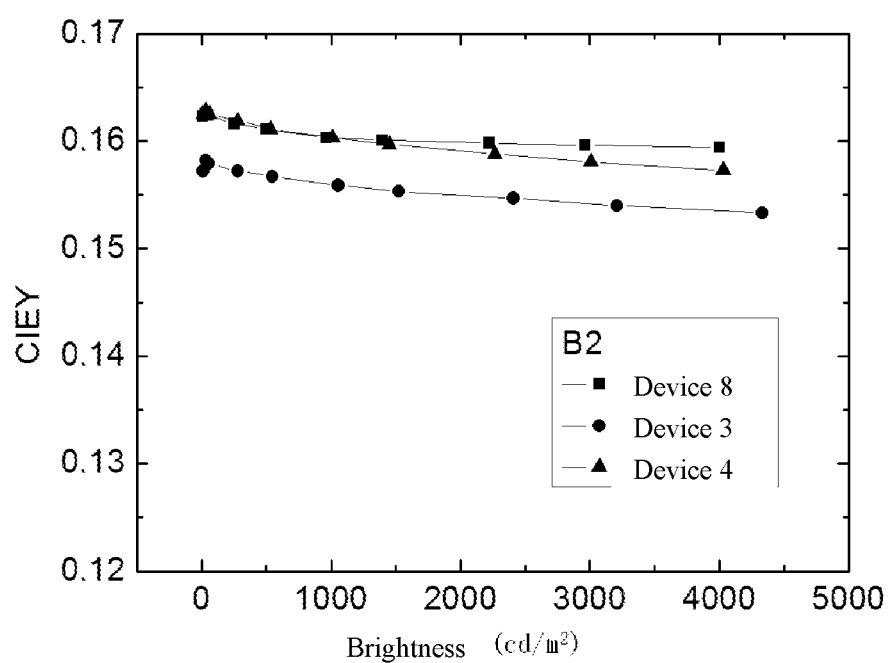
FIG. 16 shows the brightness-CIEy plot of Embodiments 6 and 7 and Comparative Example 2.
Figure 17:
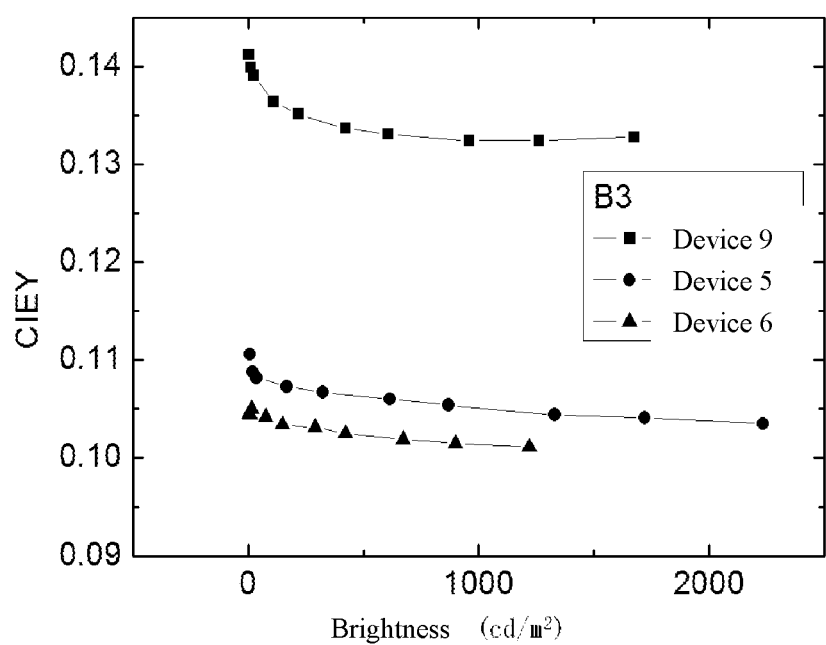
FIG. 17 shows the brightness-CIEy plot of Embodiments 8 and 9 and Comparative Example 3.

As shown from FIG. 2 and FIG. 3, the hydrogen spectra and carbon spectra of compound 89 are completely consistent with the structures. From the high performance liquid chromatogram of compound 89 in FIG. 4, the product made by the synthesis method in the invention has high purity. According to the thermal gravametric analysis of compound 89 in FIG. 5, the decomposition temperature of this type of compound is higher than 400 degrees centigrade, indicating that it has very high thermal stability.

Embodiment 4

Preparation of OLED1

Prepare OLED by the organic electronic material in the present invention Firstly, the ITO transparent conductive glass substrate 10 (with anode 20 above) is washed with detergent solution and deionized water, ethanol, acetone, deionized water in sequence, then treated with oxygen plasma for 30 seconds.

Then, perform vacuum evaporation of 10 nm HAT-CN$_6$ in ITO, which is used as the hole injection layer 30.

Then, perform vacuum evaporation of NPB, to form 30 nm thick of hole transport layer 40.

Then, perform vacuum evaporation of 30 nm thick of compound B1(2%) and compound 3(98%) in hole transport layer, which is used as light emitting layer 50.

And then, perform vacuum evaporation of 15 nm thick of TPBi in light emitting layer, which is used as electron transport layer 60.

Finally, perform vacuum evaporation of 15 nm BPhen:Li as electron injection layer 70, and vacuum evaporation of 150 nm Al as the device cathode 80.

The voltage of the device made in 20 mA/cm$^2$ of operating current density is 3.87 V, the current efficiency is 4.57 cd/A, and the peak for emitting blue light is 460 nm. The CIEy at the luminance of 1000 cd/m$^2$ is 0.135.

The said structural formula of the device

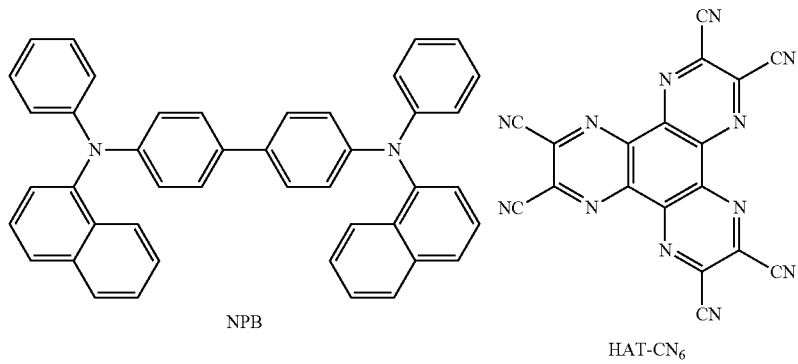

-continued

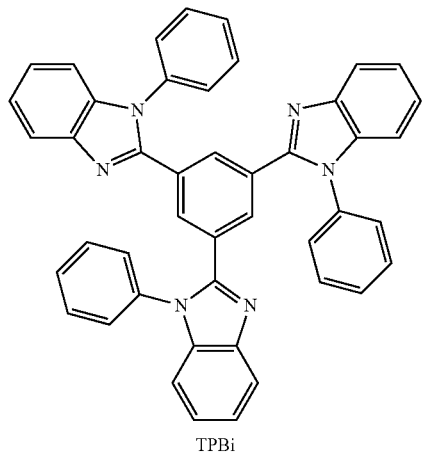
TPBi

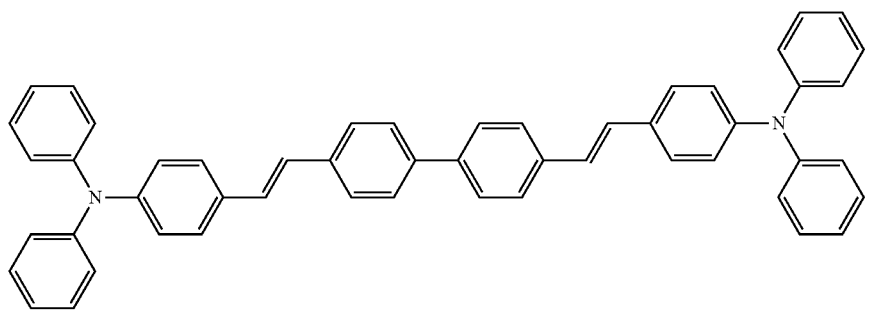
B1

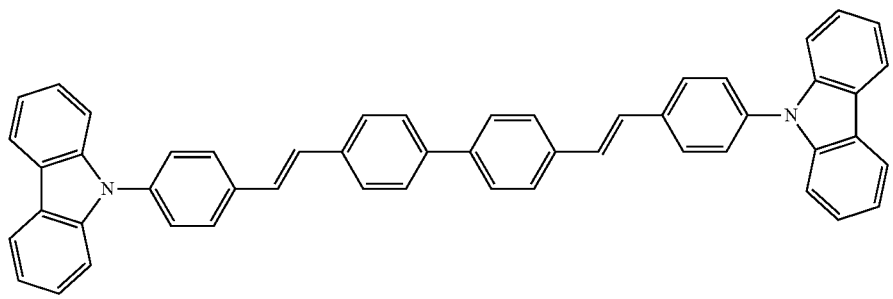
B2

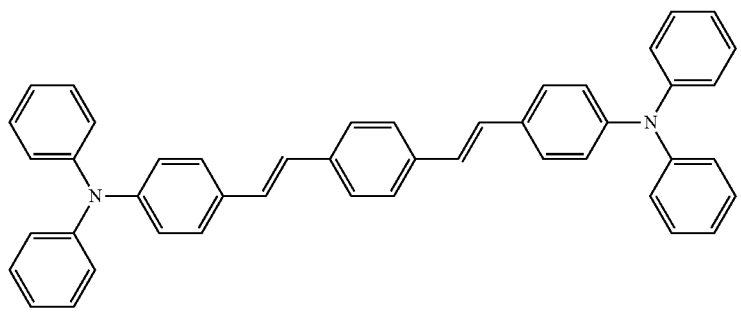
B3

Embodiment 5

Preparation of OLED2

Procedures are the same as Embodiment 4. OLED is made using compound 89 instead of compound 3.

The voltage of the device made in 20 mA/cm² of operating current density is 4.91 V, the current efficiency is 4.31 cd/A, and the peak for emitting blue light is 456 nm. The CIEy at the luminance of 1000 cd/m² is 0.143.

Embodiment 6

Preparation of OLED3

Procedures are the same as Embodiment 4. OLED is made using compound B2 instead of compound B1.

The voltage of the device made in 20 mA/cm² of operating current density is 4.09 V, the current efficiency is 5.27 cd/A, and the peak for emitting blue light is 460 nm. The CIEy at the luminance of 1000 cd/m² is 0.155.

Embodiment 7

Preparation of OLED4

Procedures are the same as Embodiment 6. OLED is made using compound 89 instead of compound 3.

The voltage of the device made in 20 mA/cm² of operating current density is 4.94V, the current efficiency is 5.05 cd/A, and the peak for emitting blue light is 460 nm. The CIEy at the luminance of 1000 cd/m² is 0.160.

Embodiment 8

Preparation of OLED5

Procedures are the same as Embodiment 4. OLED is made using compound B3 instead of compound B1.

The voltage of the device made in 20 mA/cm² of operating current density is 4.54V, the current efficiency is 3.07 cd/A, and the peak for emitting blue light is 452 nm. The CIEy at the luminance of 1000 cd/m² is 0.105.

Embodiment 9

Preparation of OLED6

Procedures are the same as Embodiment 8. OLED is made using compound 89 instead of compound 3.

The voltage of the device made in 20 mA/cm² of operating current density is 5.54V, the current efficiency is 1.44 cd/A, and the peak for emitting blue light is 452 nm. The CIEy at the luminance of 1000 cd/m² is 0.101.

Comparative Example 1

Preparation of OLED7

Procedures are the same as Embodiment 4. OLED is made using compound MADN instead of compound 3.

The voltage of the device made in 20 mA/cm² of operating current density is 5.24V, the current efficiency is 2.60 cd/A, and the peak for emitting blue light is 460 nm. The CIEy at the luminance of 1000 cd/m² is 0.164.

Comparative Example 2

Preparation of OLED8

Procedures are the same as Embodiment 6. OLED is made using compound MADN instead of compound 3.

The voltage of the device made in 20 mA/cm² of operating current density is 5.18V, the current efficiency is 4.79 cd/A, and the peak for emitting blue light is 460 nm. The CIEy at the luminance of 1000 cd/m² is 0.161.

Comparative Example 3

Preparation of OLED 9

Procedures are the same as Embodiment 8. OLED is made using compound MADN instead of compound 3.

The voltage of the device made in 20 mA/cm² of operating current density is 4.89V, the current efficiency is 2.10 cd/A, and the peak for emitting blue light is 456 nm. The CIEy at the luminance of 1000 cd/m² is 0.132.

The embodiments 4,5,6,7,8 and 9 are the specific applications of the material in the present invention. The blue light-emitting efficiency and luminance of the devices prepared are superior to the comparative examples, and the CIEy value is lower, indicating suitable for the organic dye doped blue light-emitting devices. Therefore, as stated above, the material in the present invention has high stability, and the OLED made in the invention has high efficiency and light purity.

The invention claimed is:

1. An OLED, comprising an anode, a cathode, and an organic layer; wherein the organic layer contains a light emitting layer, or a light emitting layer and one or more layers comprising a hole injection layer, a hole transport layer, an electron injection layer, an electron transport layer, or a combination thereof; wherein the light emitting layer is a host-guest doping system comprising host materials and guest materials; wherein the light emitting layer emits a blue light with a wavelength of 440-490 nm; and wherein the host material or the guest material has a structure of Formula (I),

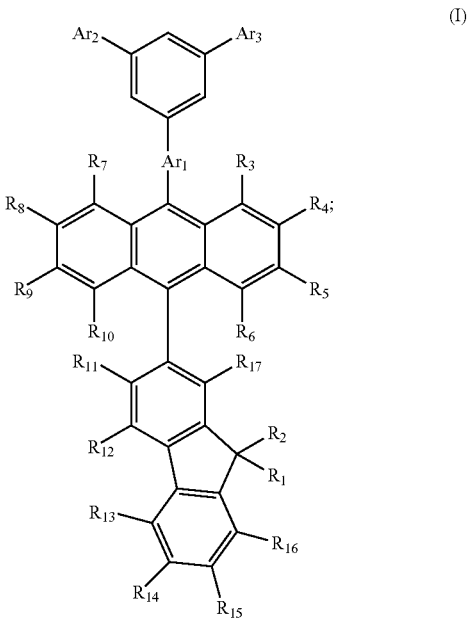

(I)

wherein $R_1$-$R_{17}$ independently represent hydrogen, halogen, cyano, nitro, C1-C8 alkyl, C1-C8 alkoxy, C2-C8 substituted or unsubstituted alkenyl, C2-C8 substituted or an unsubstituted alkynyl, C1-C4 alkyl substituted or unsubstituted phenyl, C1-C4 alkyl substituted or unsubstituted naphthyl, or combined C1-C4 alkyl substituted or unsubstituted fluorenyl; and wherein $Ar_1$, $Ar_2$, and $Ar_3$ independently represent C1-C4 alkyl substituted phenyl, phenyl, or pyridyl.

2. The OLED according to claim 1, wherein $R_1$-$R_2$ independently and represent hydrogen, halogen, C1-C4 alkyl, C1-C4 alkyl substituted or unsubstituted phenyl, C1-C4 alkyl substituted or unsubstituted naphthyl, or combined C1-C4 alkyl-substituted or unsubstituted fluorenyl; wherein $R_3$-$R_{17}$ independently represent hydrogen, halogen, C1-C4 alkyl, C1-C4 alkyl substituted or unsubstituted phenyl, or C1-C4 alkyl-substituted or unsubstituted naphthyl; and wherein $Ar_1$, $Ar_2$, and $Ar_3$ independently represent phenyl, tolyl, xylyl, t-butylphenyl, or pyridyl.

3. The OLED according to claim 2, wherein $R_3$-$R_{17}$ represents hydrogen; wherein $R_1$ and $R_2$ independently represent hydrogen, methyl, ethyl, propyl, isopropyl, t-butyl, phenyl, biphenyl, naphthyl, or combined fluorenyl; and wherein $Ar_1$, $Ar_2$, and $Ar_3$ independently represent phenyl, pyridyl, tolyl, or xylyl.

4. The OLED according to claim 3, wherein $R_3$-$R_{17}$ represent hydrogen $R_1$, $R_2$ independently represent hydrogen, methyl, or combined fluorenyl; and wherein $Ar_1$, $Ar_2$, and $Ar_3$ represent phenyl.
5. The OLED according to claim 1, wherein the compound with the structure of Formula (I) is:
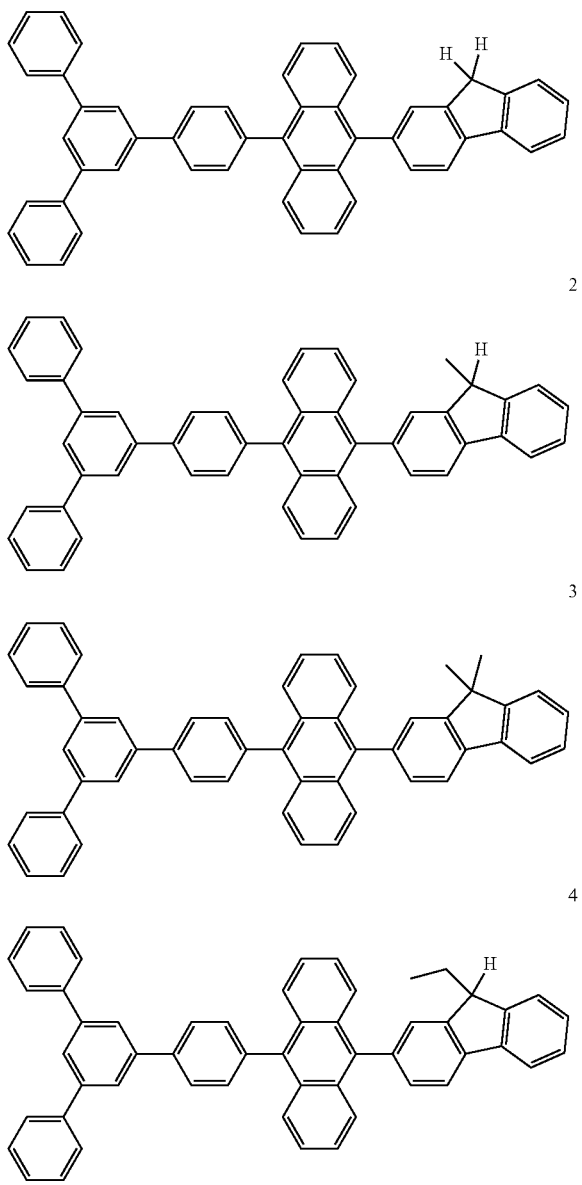
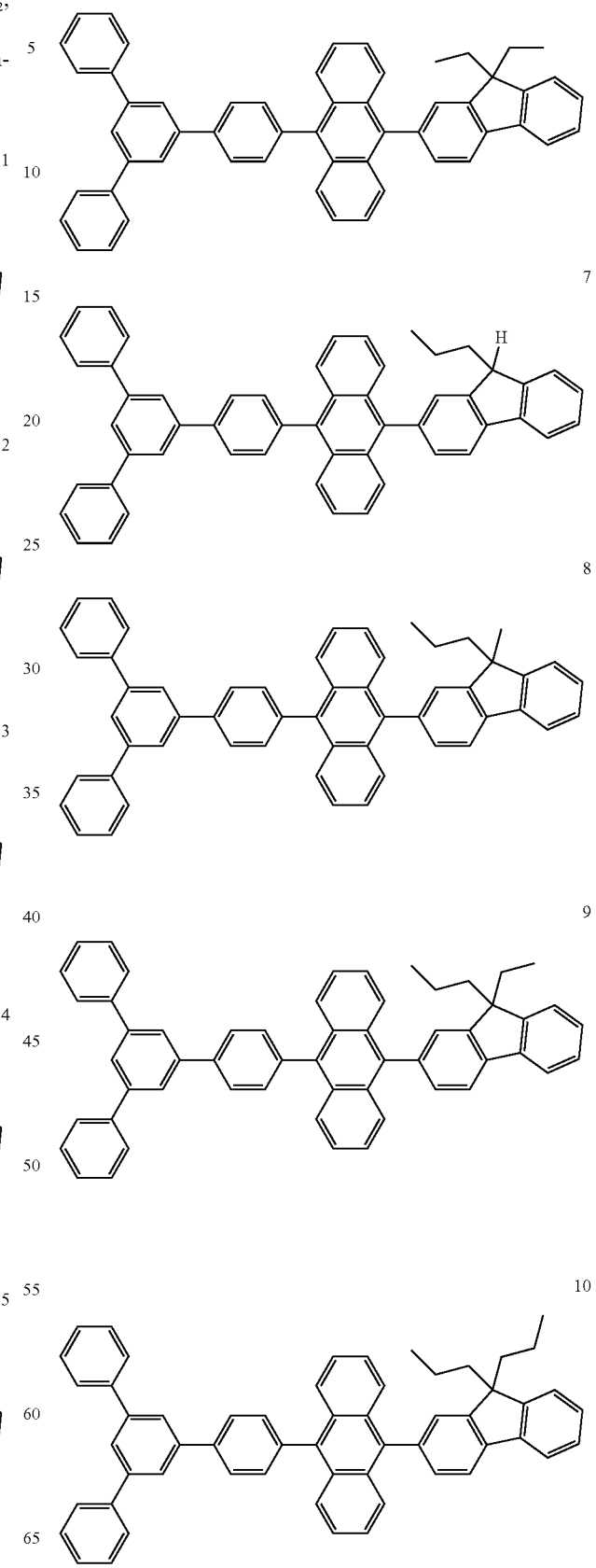

11
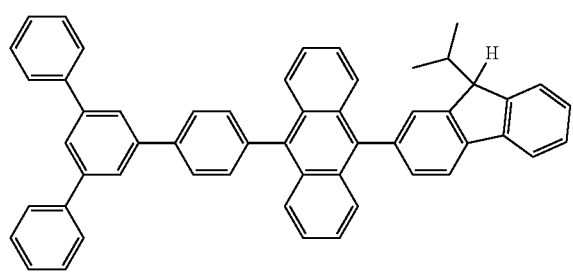
12
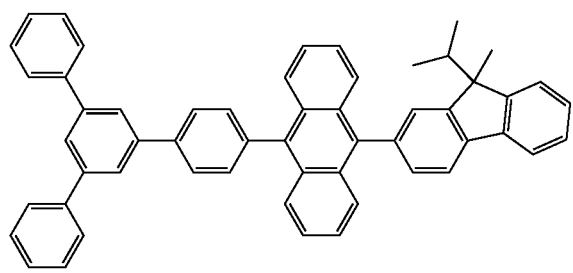
13
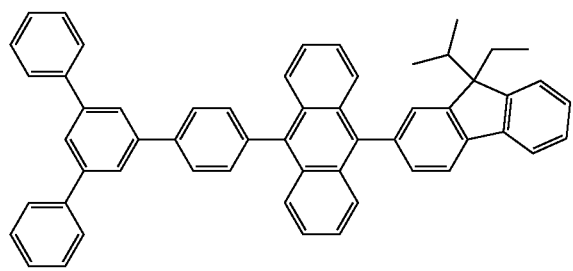
14
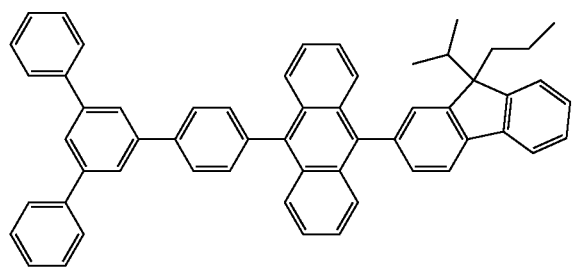
15
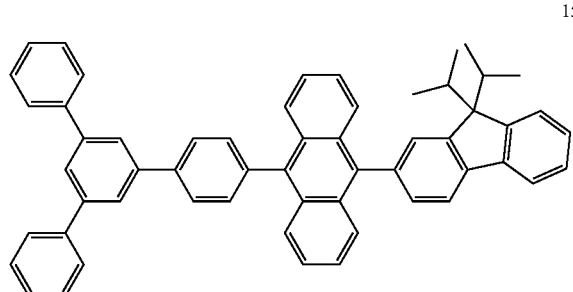
16
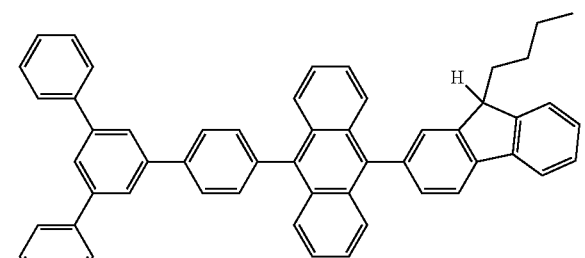
17
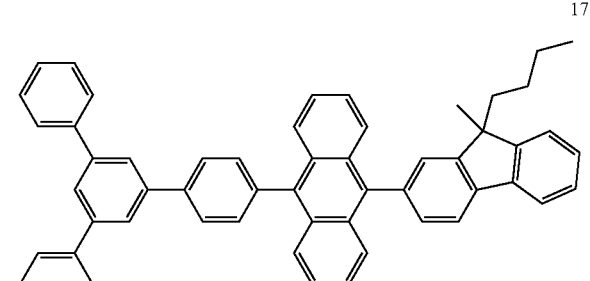
18
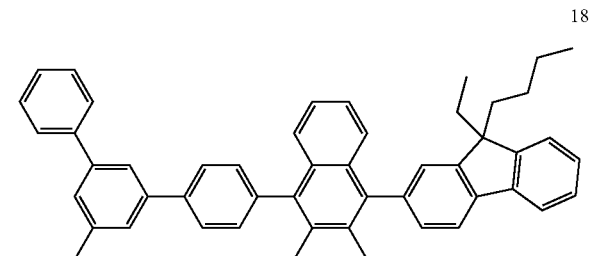
19
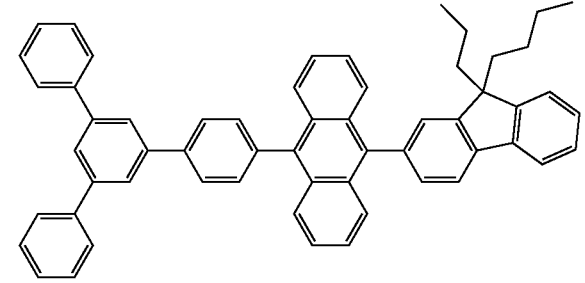
20
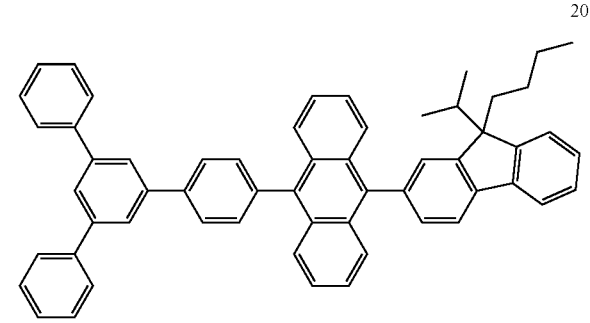

21
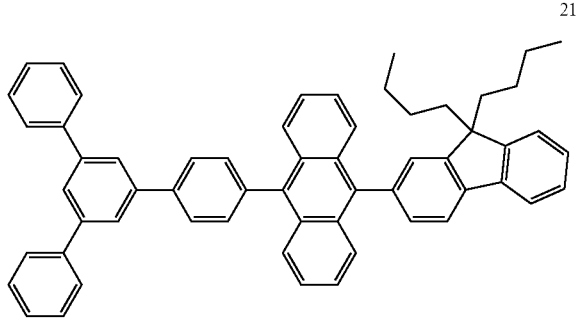
22
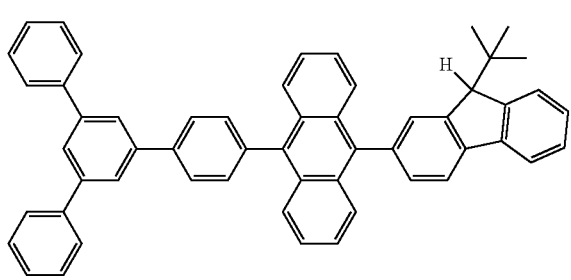
23
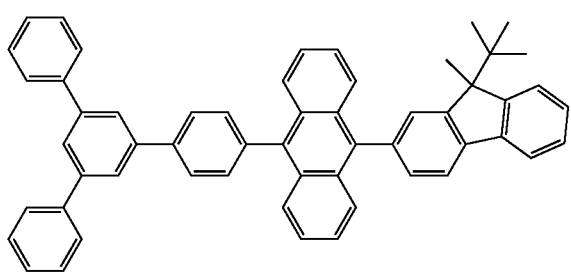
24
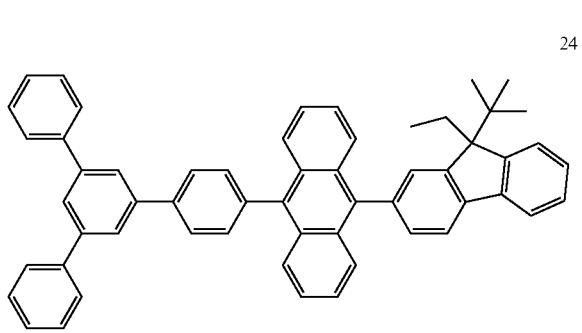
25
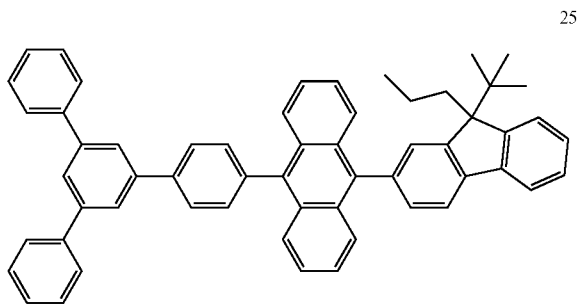
26
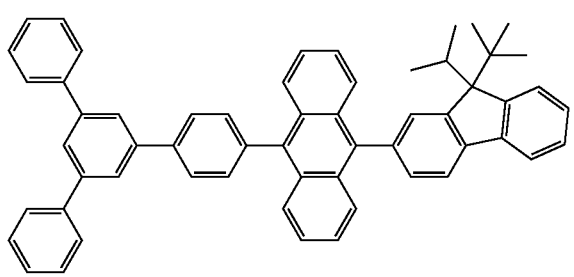
27
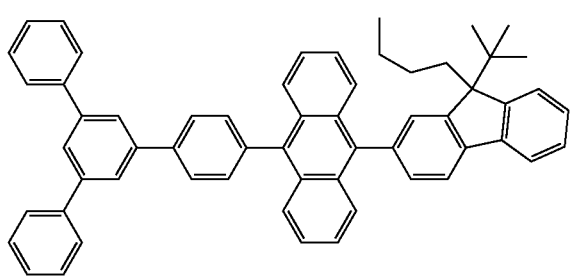
28
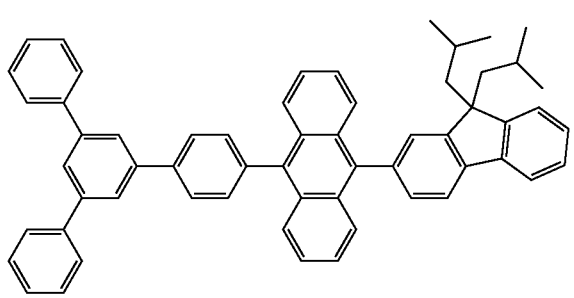
29
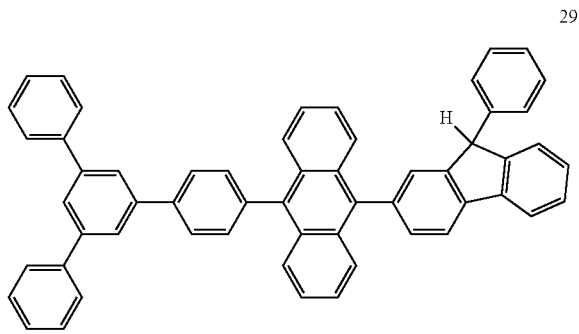
30
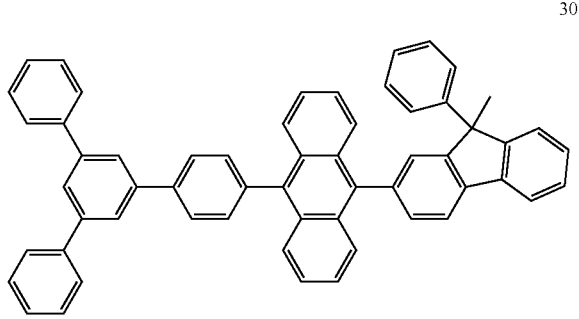

31
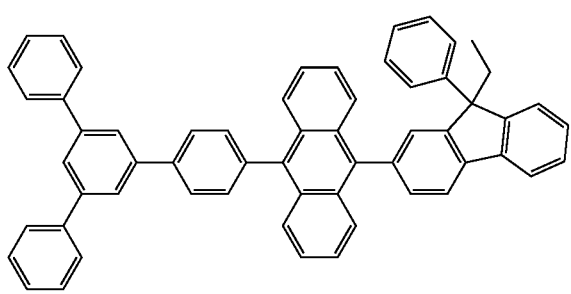
32
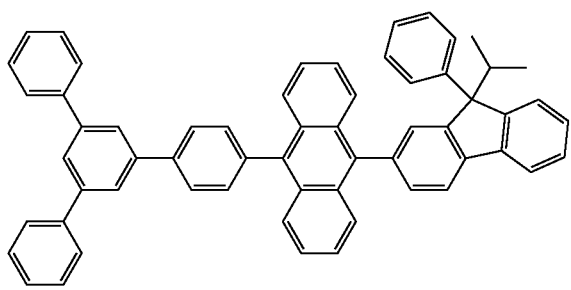
33
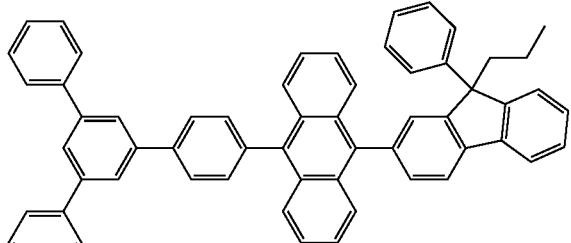
34
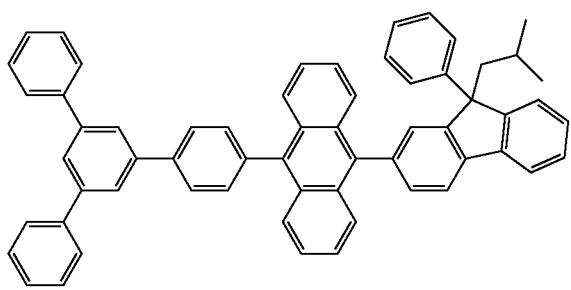
35
36
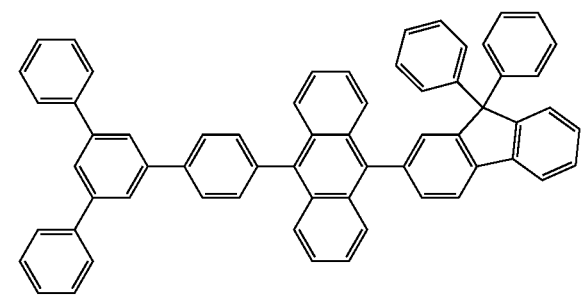
37
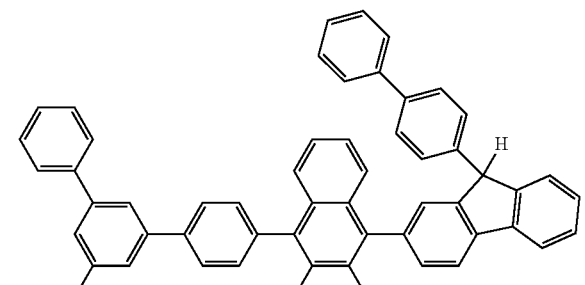
38
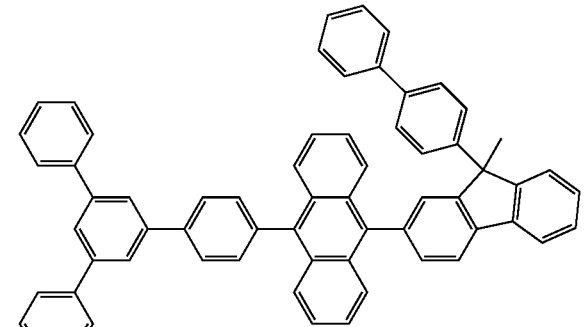
39
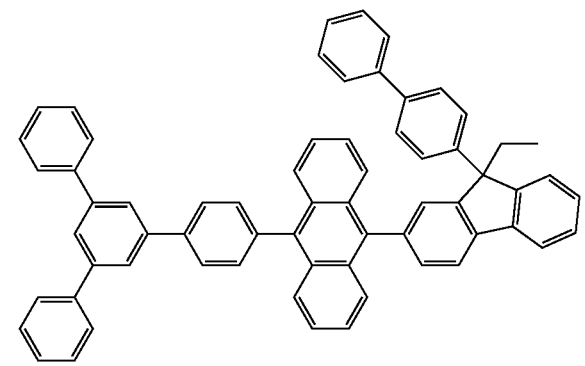

40
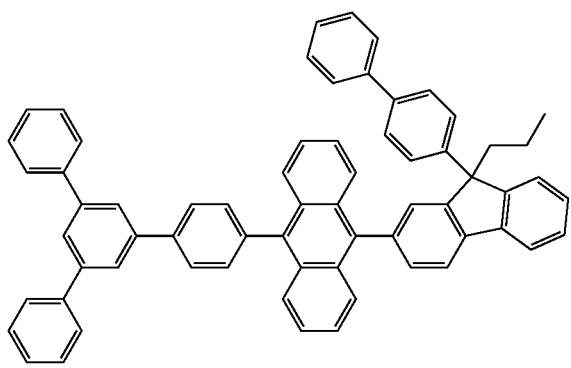
41
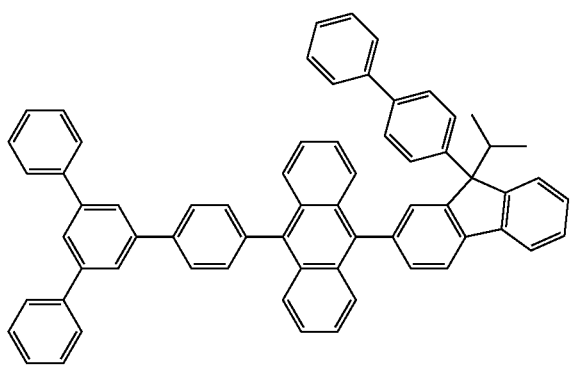
42
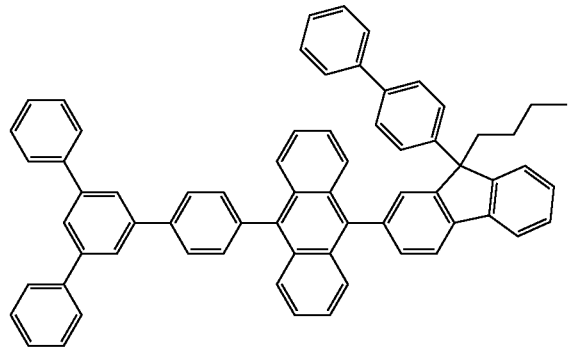
43
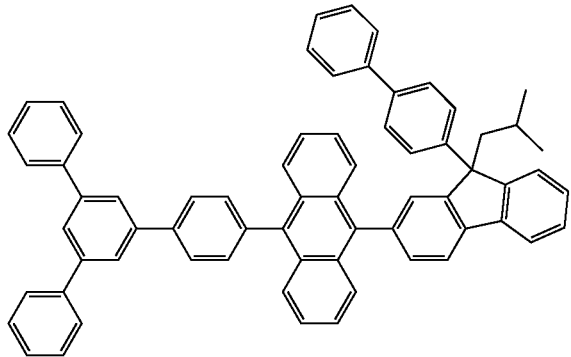
44
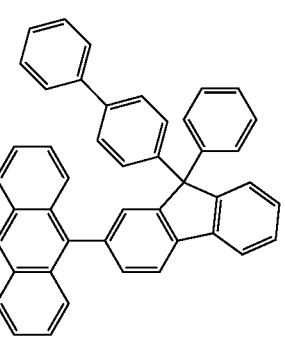
45
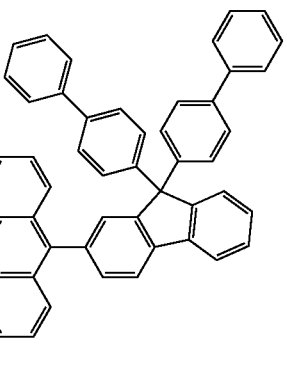
46
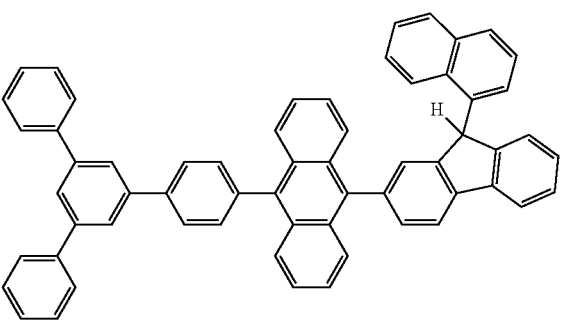
47
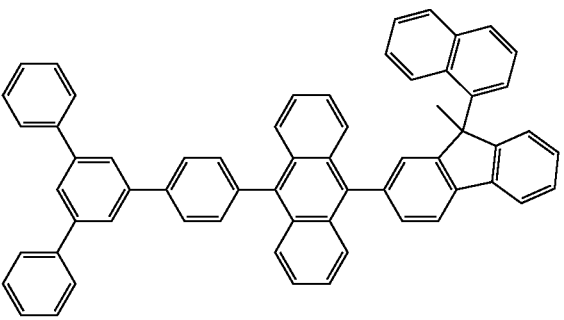

48
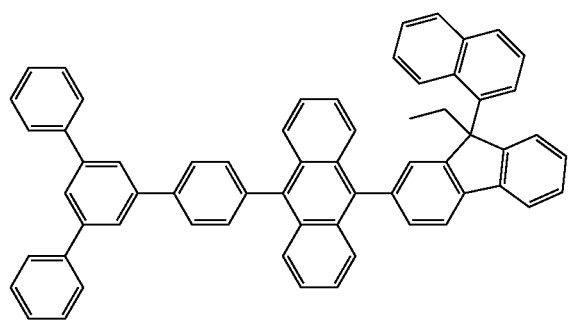
52
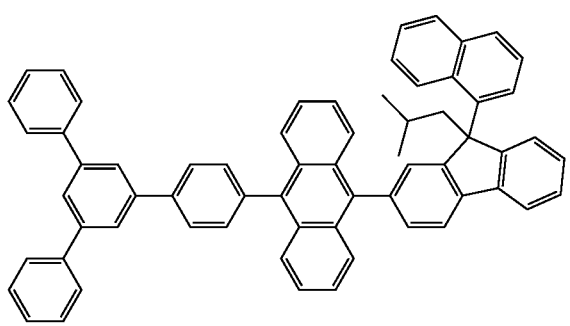
49
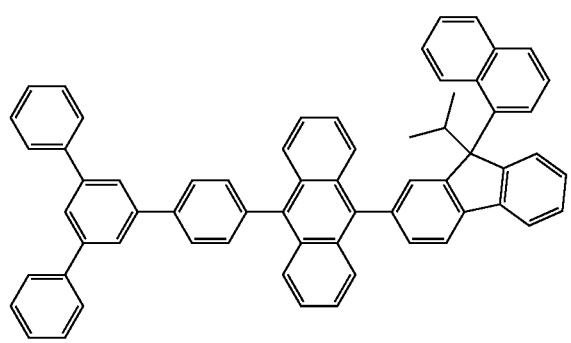
53
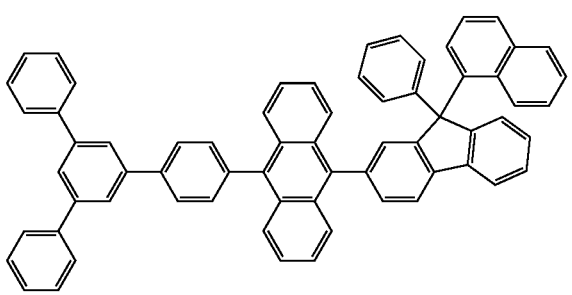
50
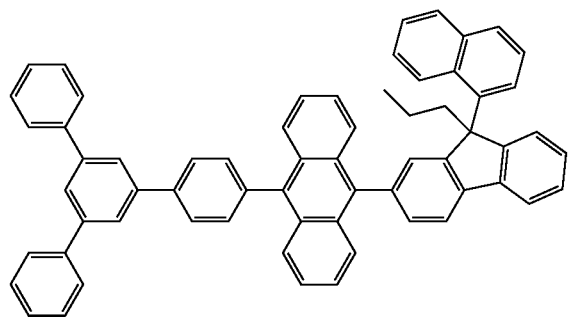
54
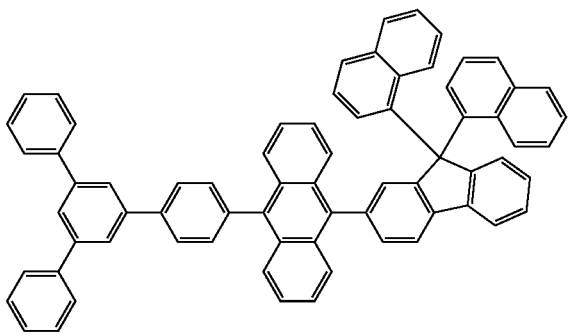
51
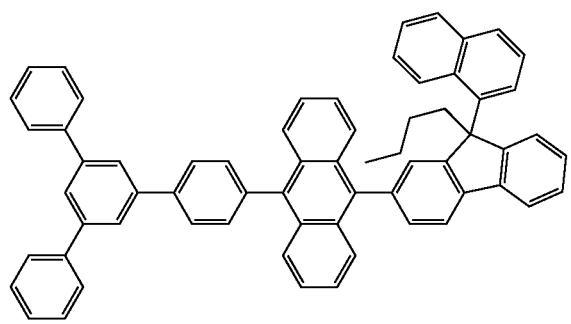
55
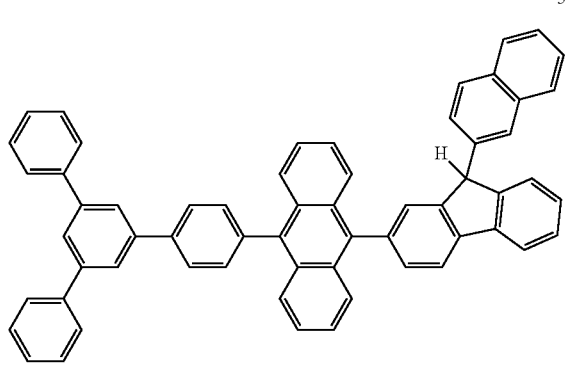

56
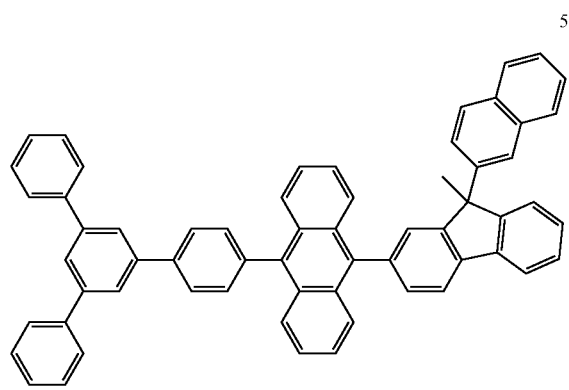
57
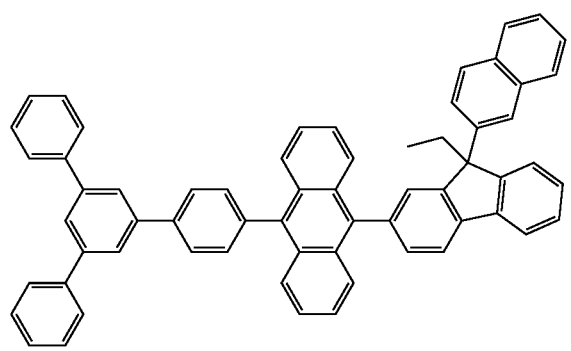
58
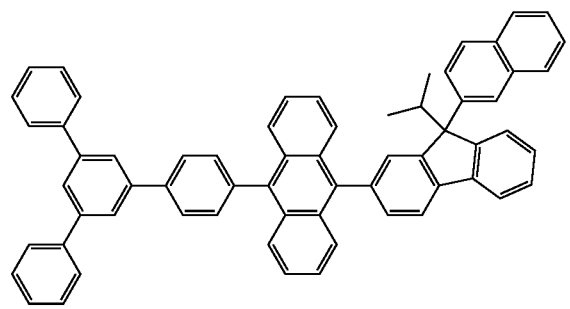
59
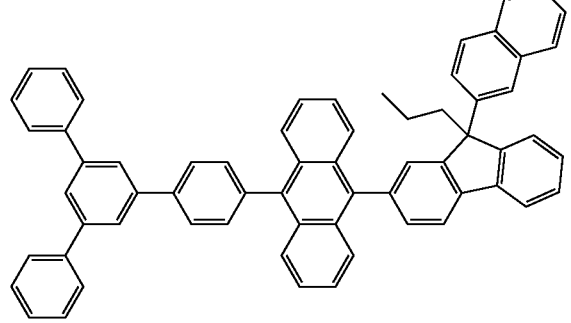
60
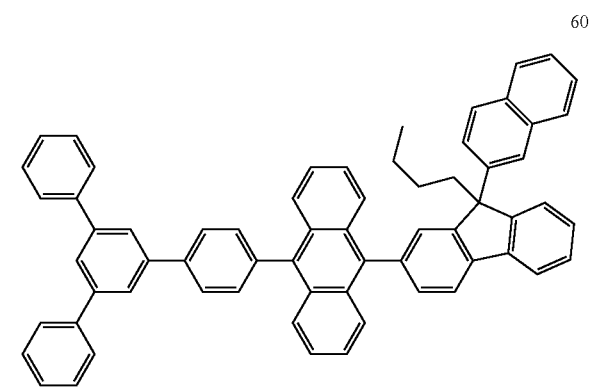
61
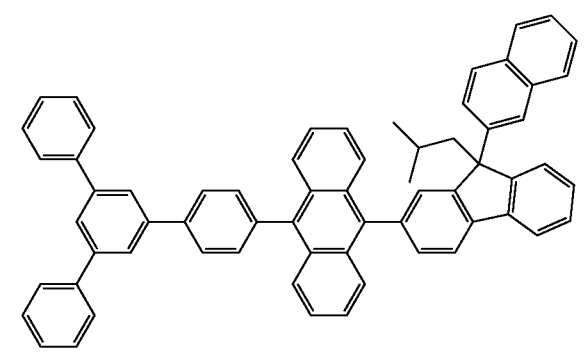
62
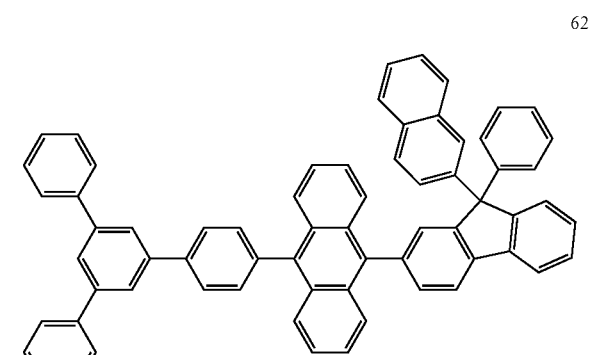
63
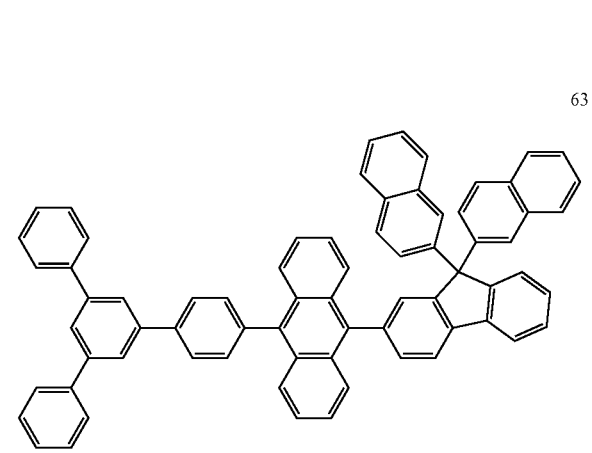

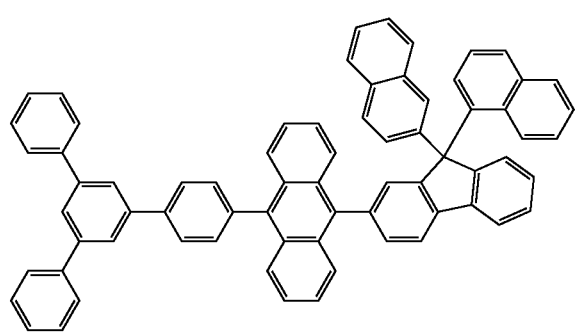
64
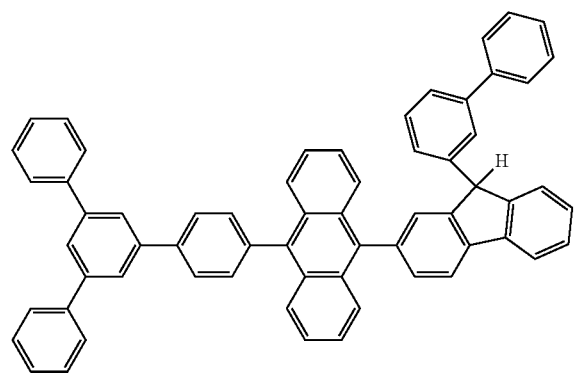
65
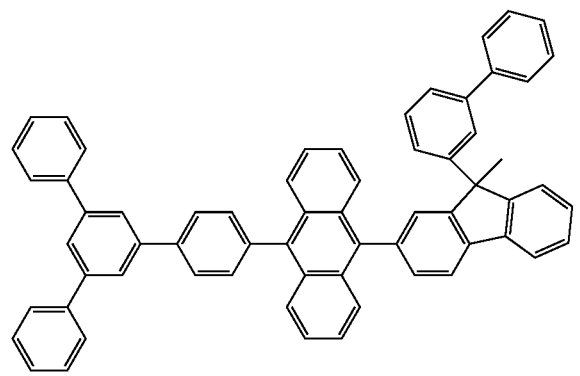
66
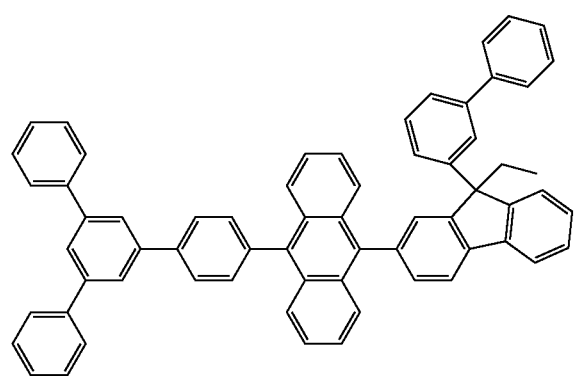
67
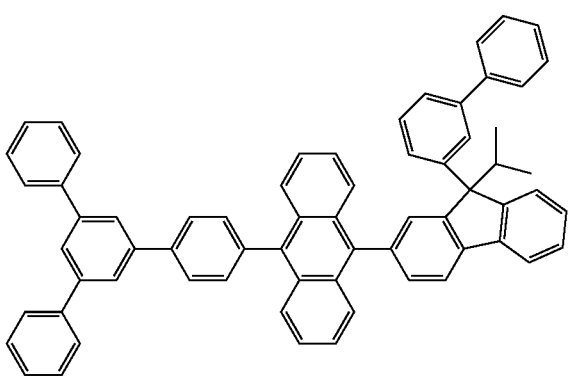
68

72
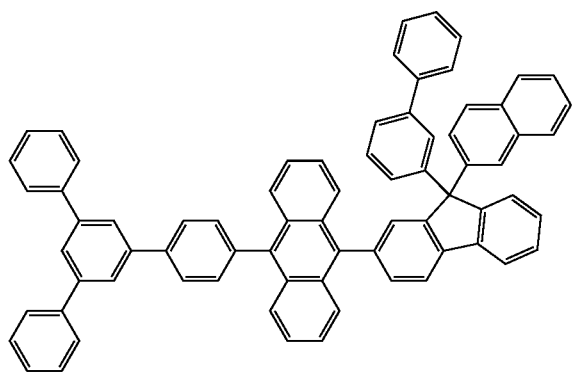
73
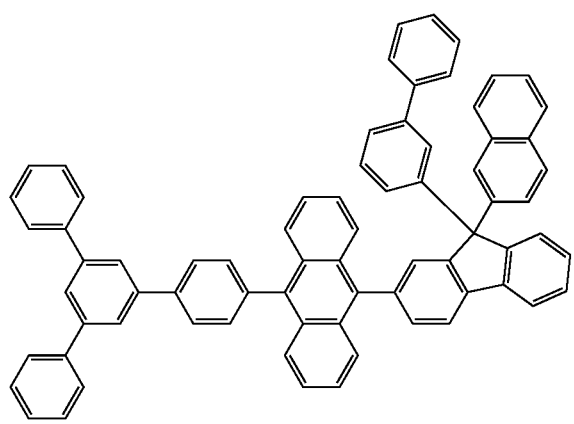
74
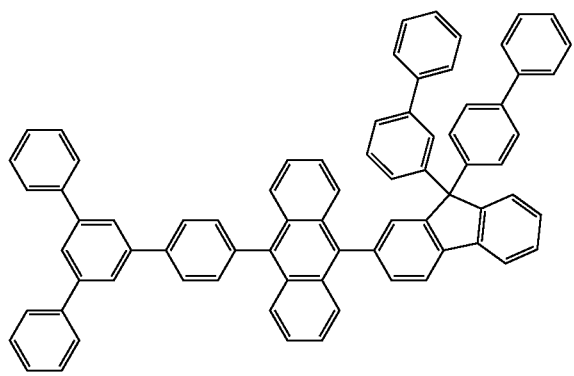
75
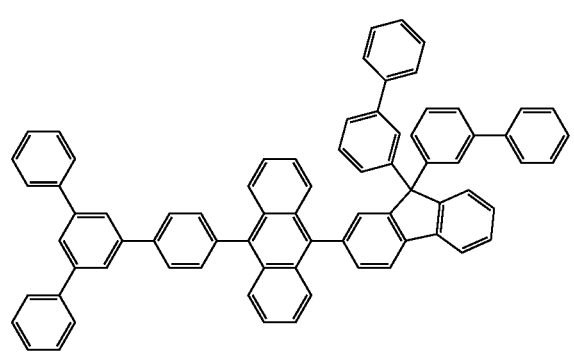
76
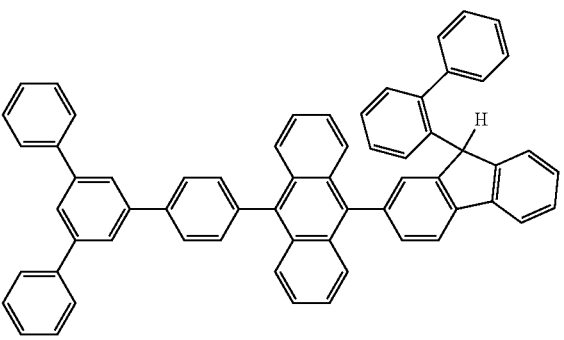
77
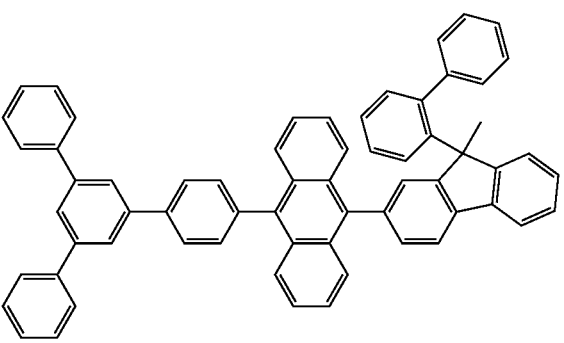
78
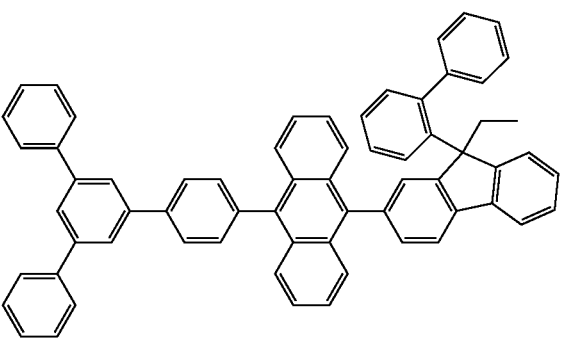
79
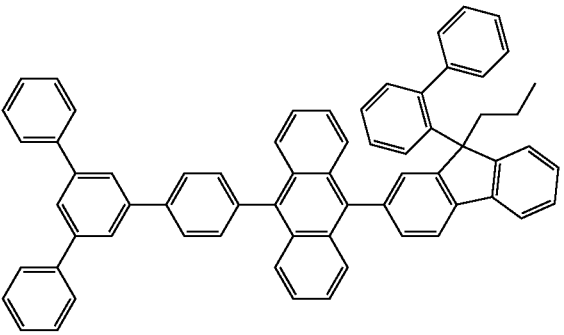

80
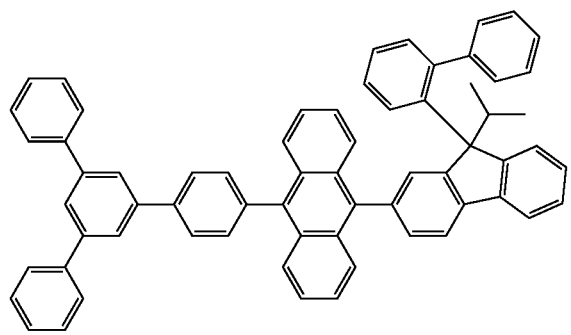
81
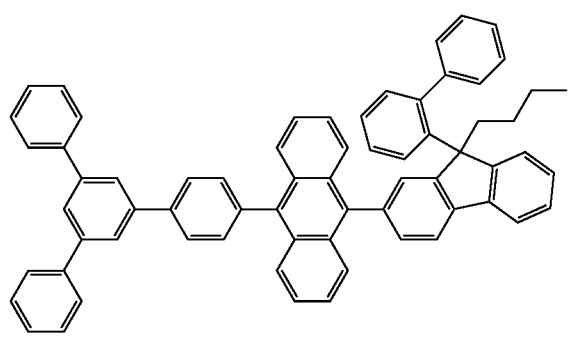
82
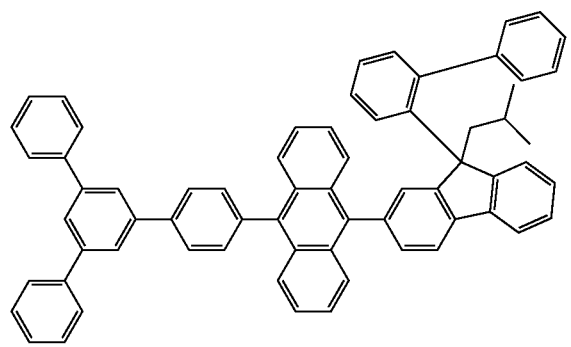
83
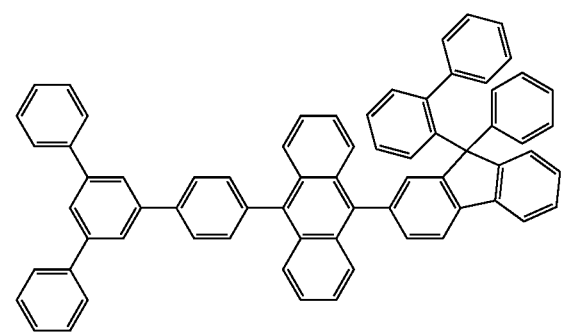
84
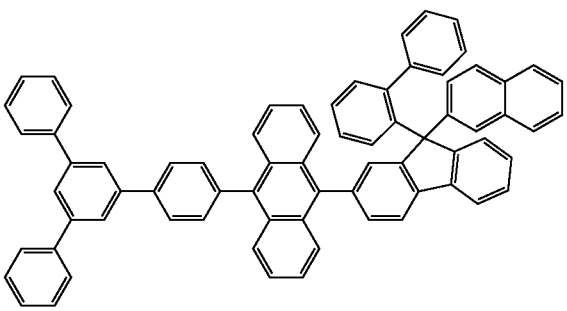
85
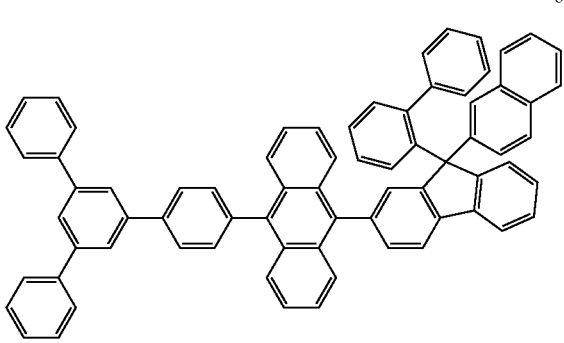
86
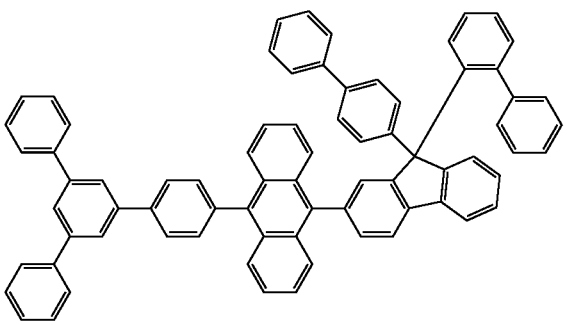
87

88
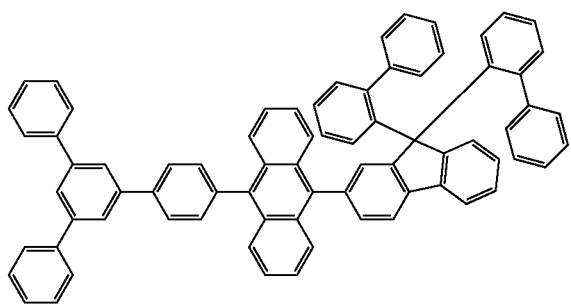
89
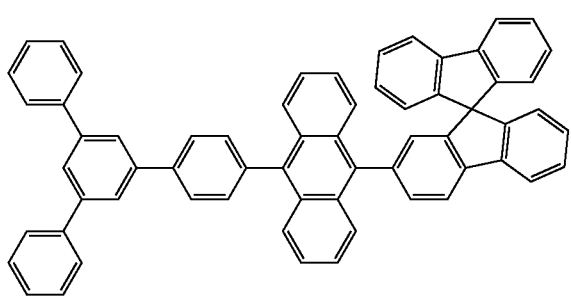
184
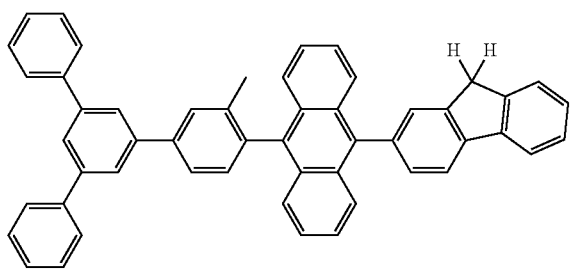
185
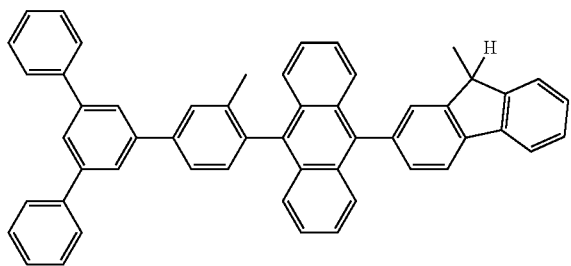
186
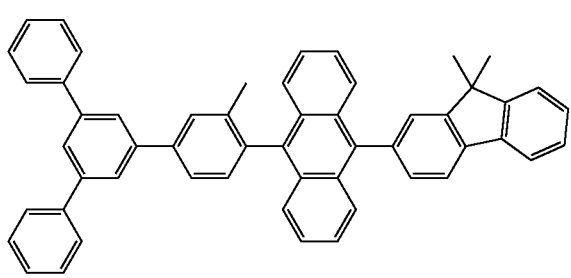
187
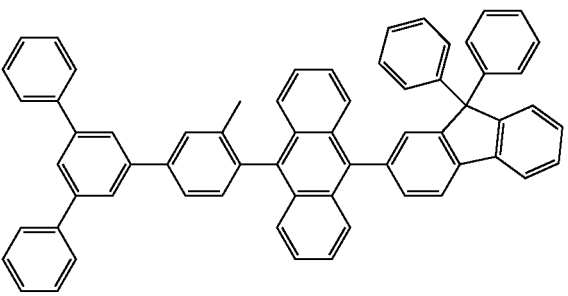
188
189
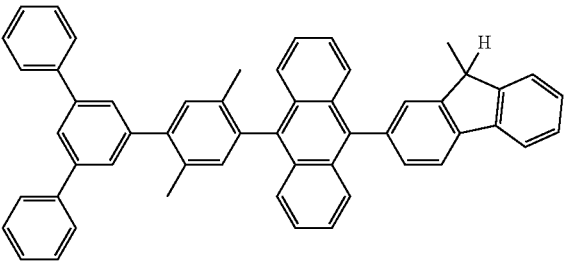
190
191
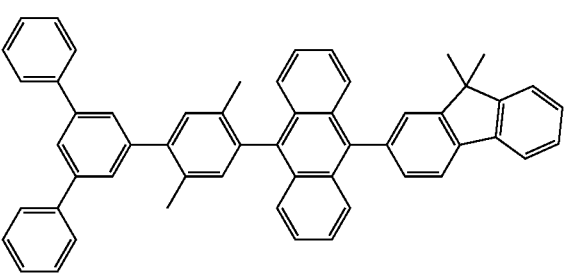

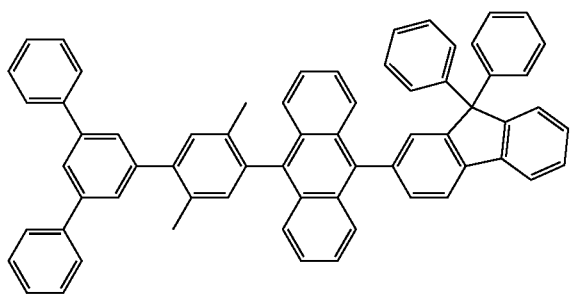
192
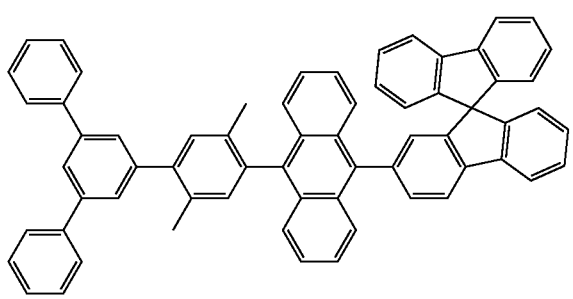
193
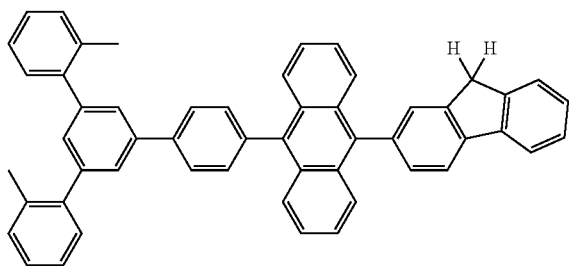
194
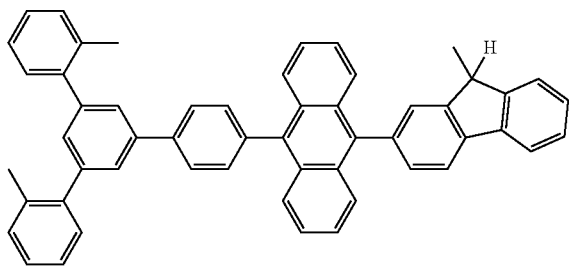
195
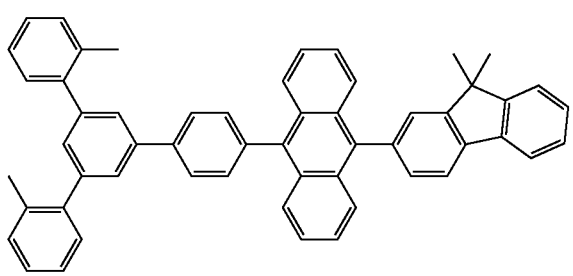
196
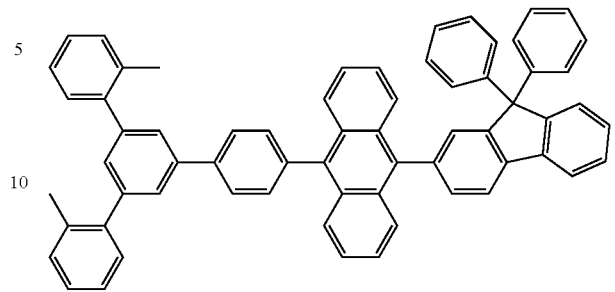
197

202
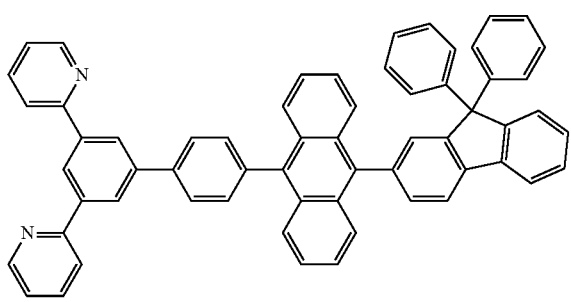
203
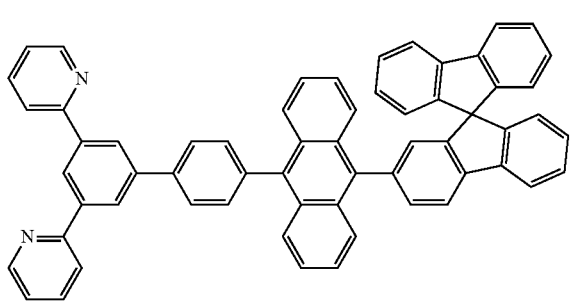
204
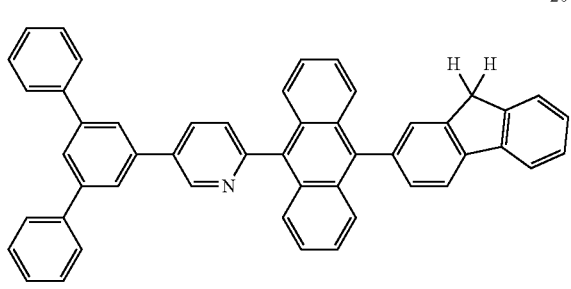
205
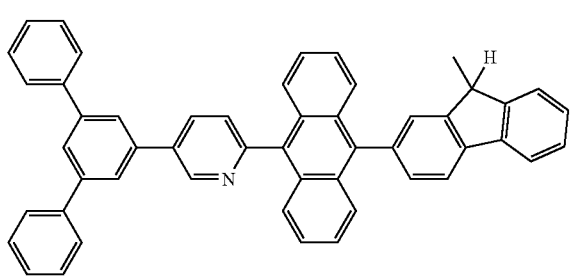
206
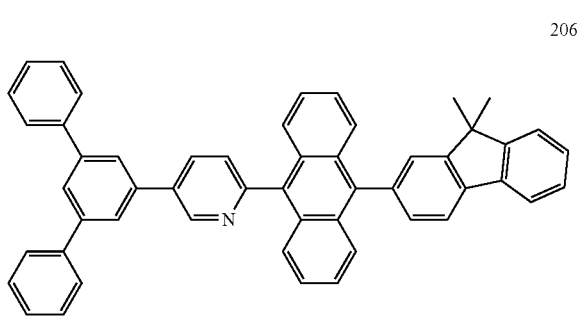
207
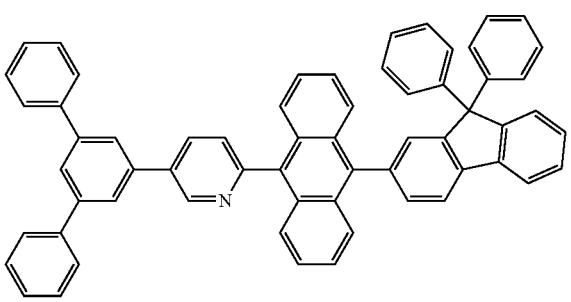
208
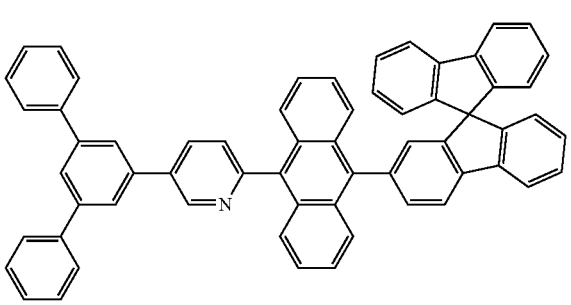
209
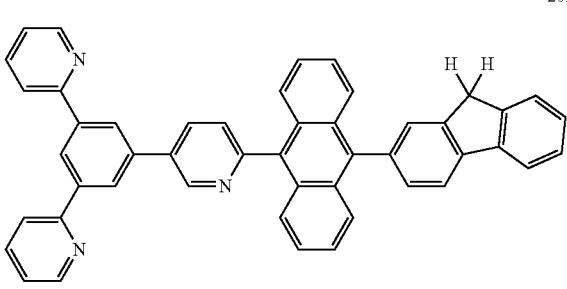
210
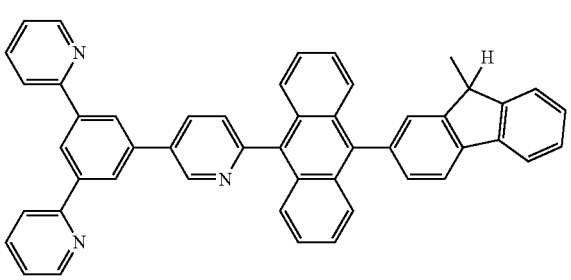
211
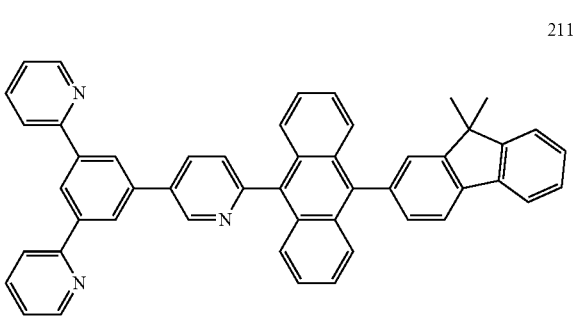

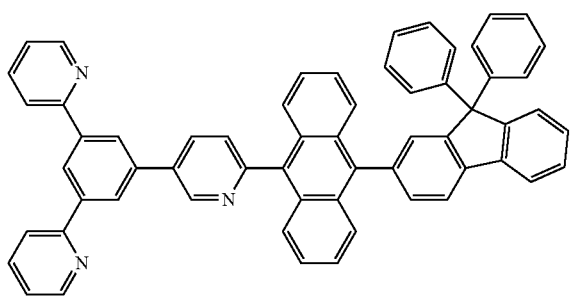
212
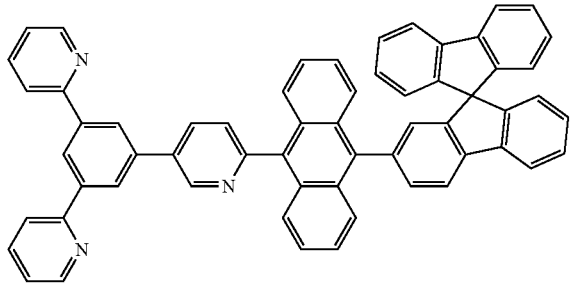
213
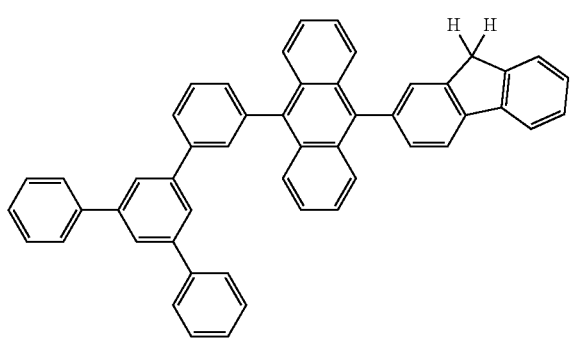
219
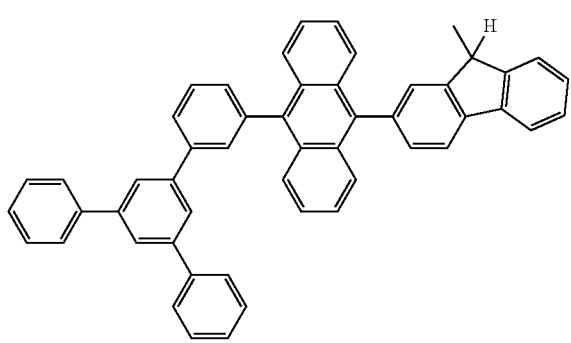
220
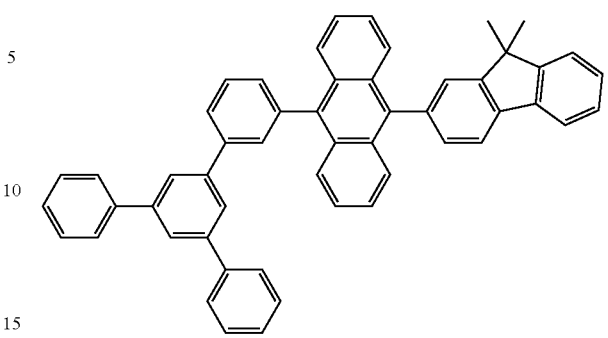
221
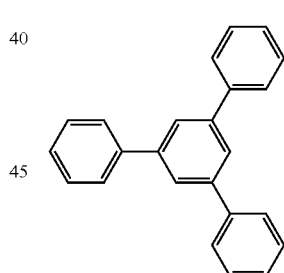
222
or
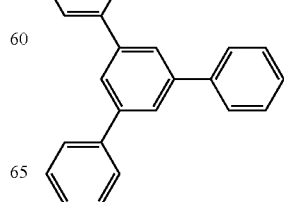
223
6. The OLED according to claim 5, wherein the compound has the following structure:
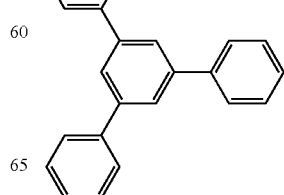
1

-continued

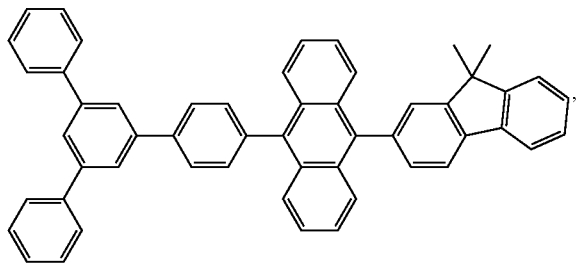

or

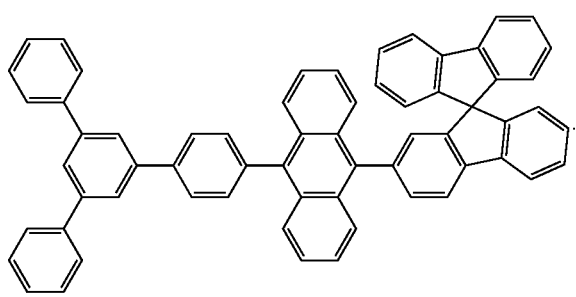

7. The OLED according to claim 1, wherein the concentration of the host material is 20-99.9% of the organic layer by weight, and wherein the concentration of the guest material is 0.01-80% of the organic layer by weight.

8. The OLED according to claim 7, wherein the concentration of the host material is 80-99% of the organic layer by weight, and wherein the concentration of the guest material is 1-20% of the organic layer by weight.

9. The OLED according to claim 8, wherein the host material is the compound with the structure of Formula (I) with a concentration of 90-99% of the organic layer by weight; wherein the concentration of the guest material is 1-10% of the organic layer by weight, and the guest material comprises naphthalene compounds, pyrene compounds, fluorene compounds, phenanthrene compounds, chrysene compounds, fluoranthene compounds, anthracene compounds, dibenzanthracene compounds, perylene compound, bi-aryl vinyl compounds, triphenylamine vinyl compounds, amine compounds, benzimidazole compounds, furan compounds or organic metal chelate compounds.

10. The OLED according to claim 8, wherein the guest material comprises one or more of the following structures:

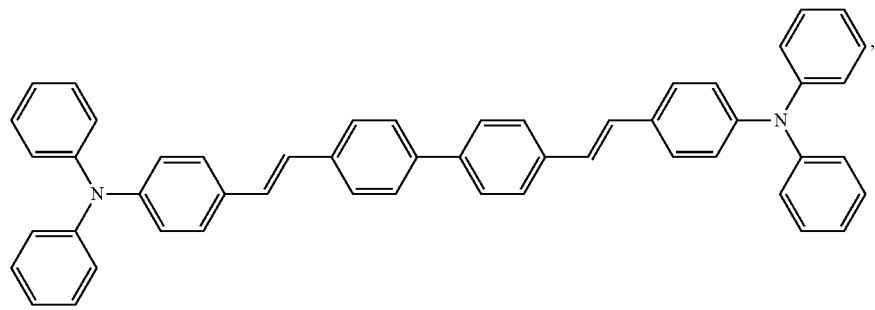

B1

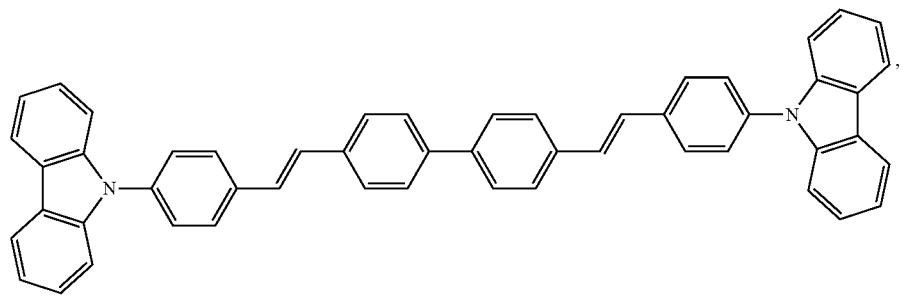

B2 and/or

-continued

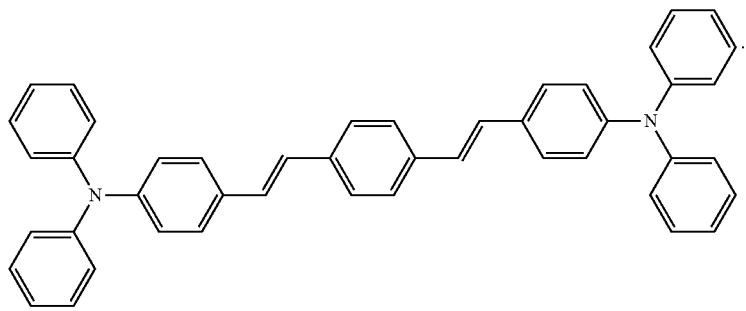

B3

11. The OLED according to claim 8, wherein the compound with structure of Formula (I) is further located in a hole injection layer, a hole transport layer, an electron transport layer, and/or electron injection layer.

12. The OLED according to claim 2, wherein the concentration of the host material is 20-99.9% of the organic layer by weight, and wherein the concentration of the guest material is 0.01-80% of the organic layer by weight.

13. The OLED according to claim 3, wherein the concentration of the host material is 20-99.9% of the organic layer by weight, and wherein the concentration of the guest material is 0.01-80% of the organic layer by weight.

14. The OLED according to claim 4, wherein the concentration of the host material is 20-99.9% of the organic layer by weight, and wherein the concentration of the guest material is 0.01-80% of the organic layer by weight.

15. The OLED according to claim 5, wherein the concentration of the host material is 20-99.9% of the organic layer by weight, and wherein the concentration of the guest material is 0.01-80% of the organic layer by weight.

16. The OLED according to claim 6, wherein the concentration of the host material is 20-99.9% of the organic layer by weight, and wherein the concentration of the guest material is 0.01-80% of the organic layer by weight.

* * * * *